(12) United States Patent
Marnfeldt et al.

(10) Patent No.: US 6,285,731 B1
(45) Date of Patent: Sep. 4, 2001

(54) COUNTING DEVICE AND INHALER INCLUDING A COUNTING DEVICE

(75) Inventors: Göran Marnfeldt, Blentarp (SE); Stephen Theobald, Harboöre (DK)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/297,866

(22) PCT Filed: Mar. 30, 1999

(86) PCT No.: PCT/SE99/00533

§ 371 Date: May 10, 1990

§ 102(e) Date: May 10, 1990

(87) PCT Pub. No.: WO99/50793

PCT Pub. Date: Oct. 7, 1999

(30) Foreign Application Priority Data

Mar. 30, 1998 (SE) .................................................. 9801115

(51) Int. Cl.[7] ...................................................... G06M 3/12

(52) U.S. Cl. ................................. 377/15; 377/16; 377/30; 128/200.14

(58) Field of Search ................................... 377/15, 16, 30, 377/32, 33; 128/200.14, 200.19, 200.23, 205.23

(56) References Cited

U.S. PATENT DOCUMENTS

| | | | |
|---|---|---|---|
| 4,878,136 | 10/1989 | Sarraf et al. | 360/78.04 |
| 5,593,390 | * 1/1997 | Castellano et al. | 604/187 |
| 6,142,146 | * 11/2000 | Abrams et al. | 128/203.15 |

* cited by examiner

Primary Examiner—Tuan T. Lam
(74) Attorney, Agent, or Firm—Fish & Richardson P.C.

(57) ABSTRACT

A counting device, comprising: an input 105, 107 for receiving an input signal having at least three distinct input states; memory means 810 for storing a count; and means 620 responsive to a predetermined sequence of input states of said input signal to vary said count, wherein said predetermined sequence includes the at least three input states.

21 Claims, 85 Drawing Sheets

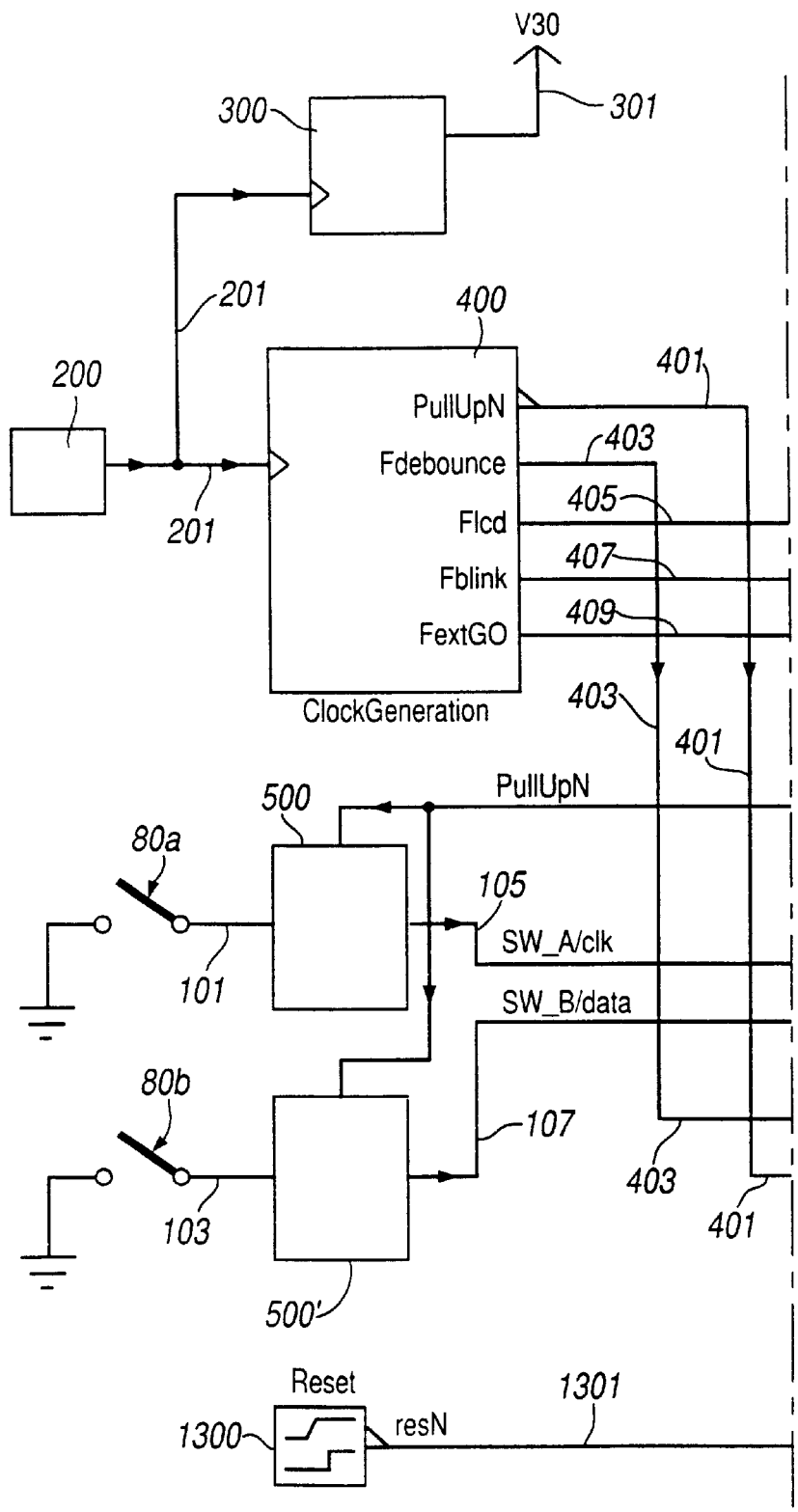
Fig.3 (Part I)

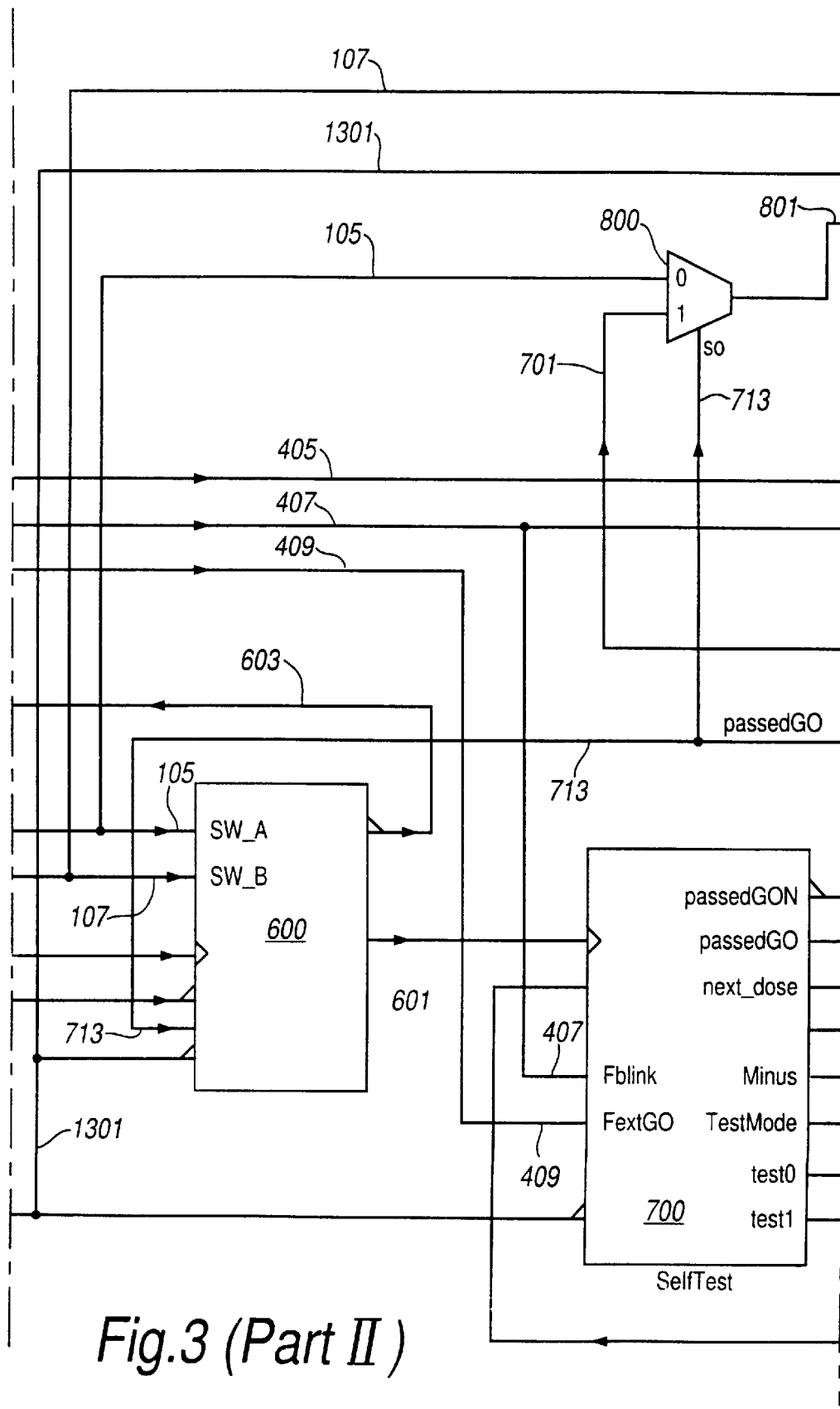
Fig.3 (Part II)

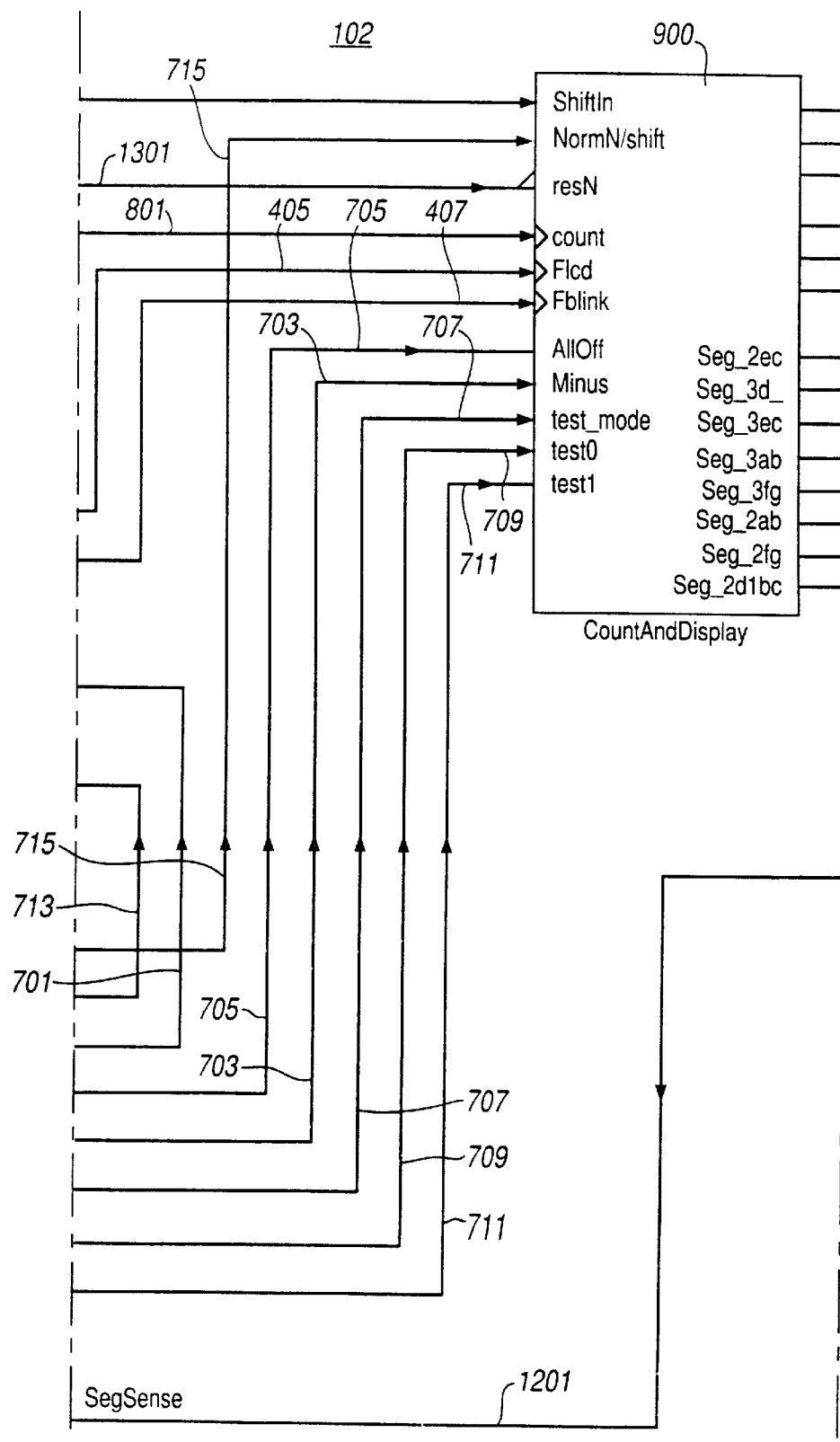
Fig.3 (Part III)

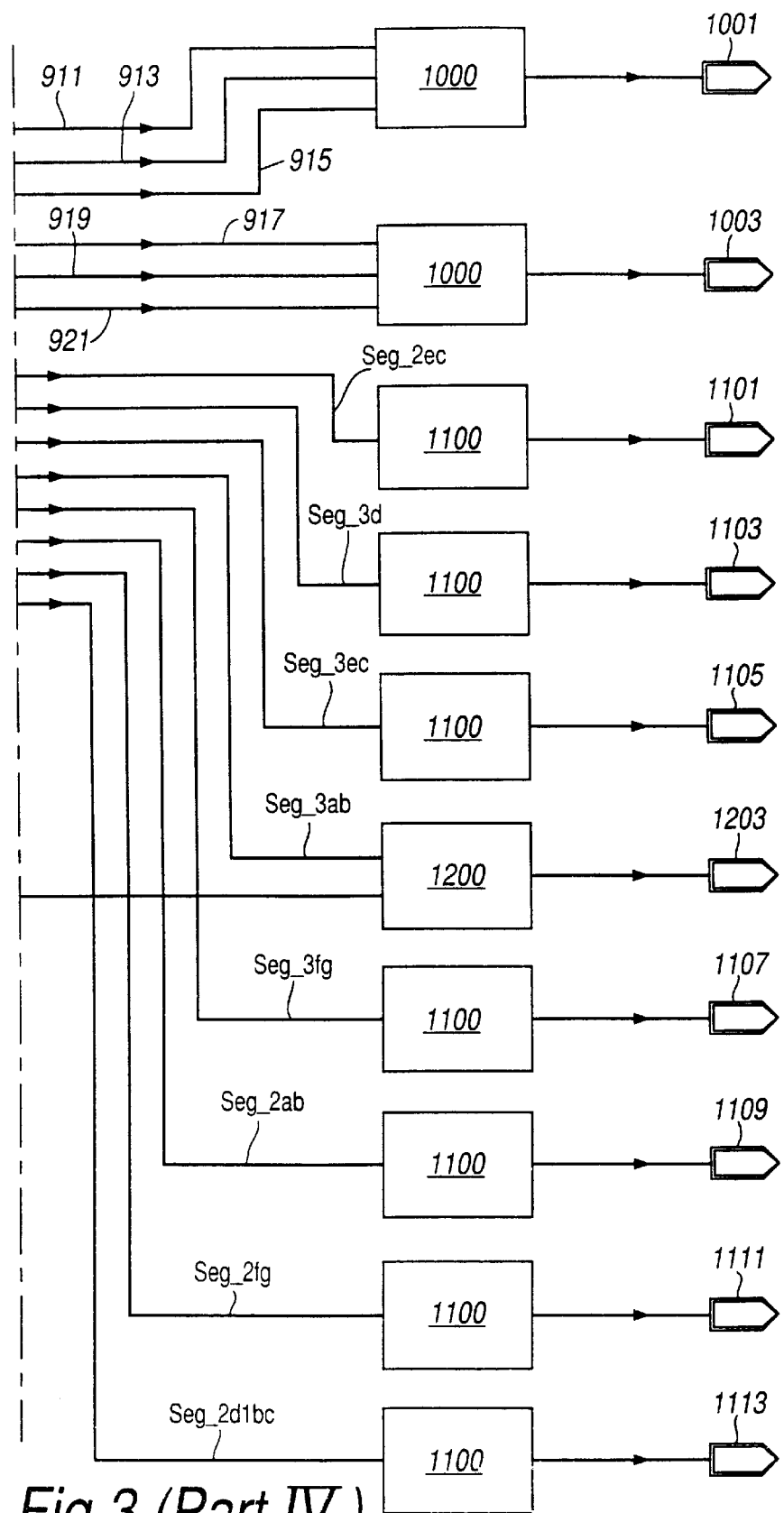
Fig.3 (Part IV)

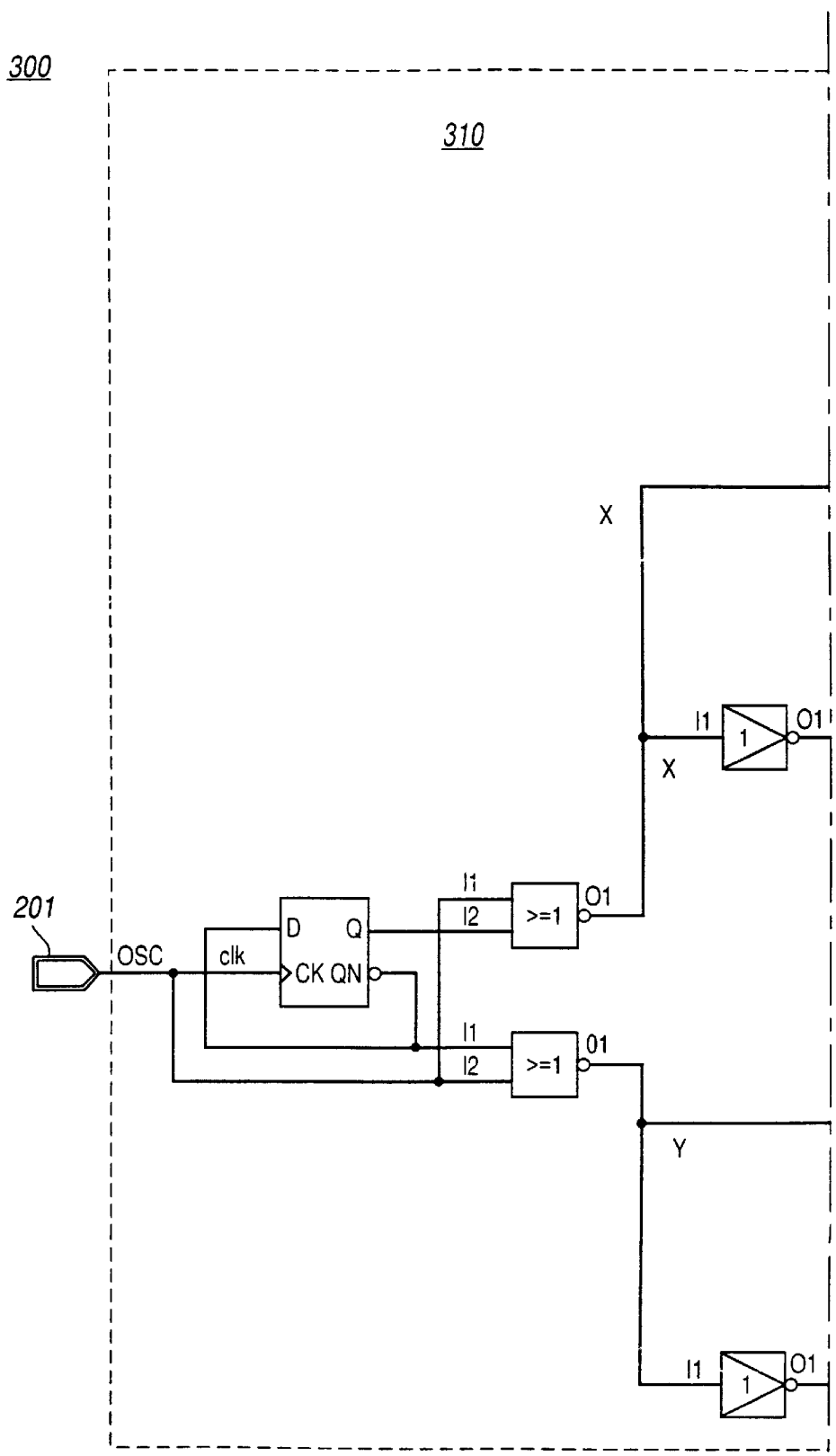
Fig.7 (Part I)

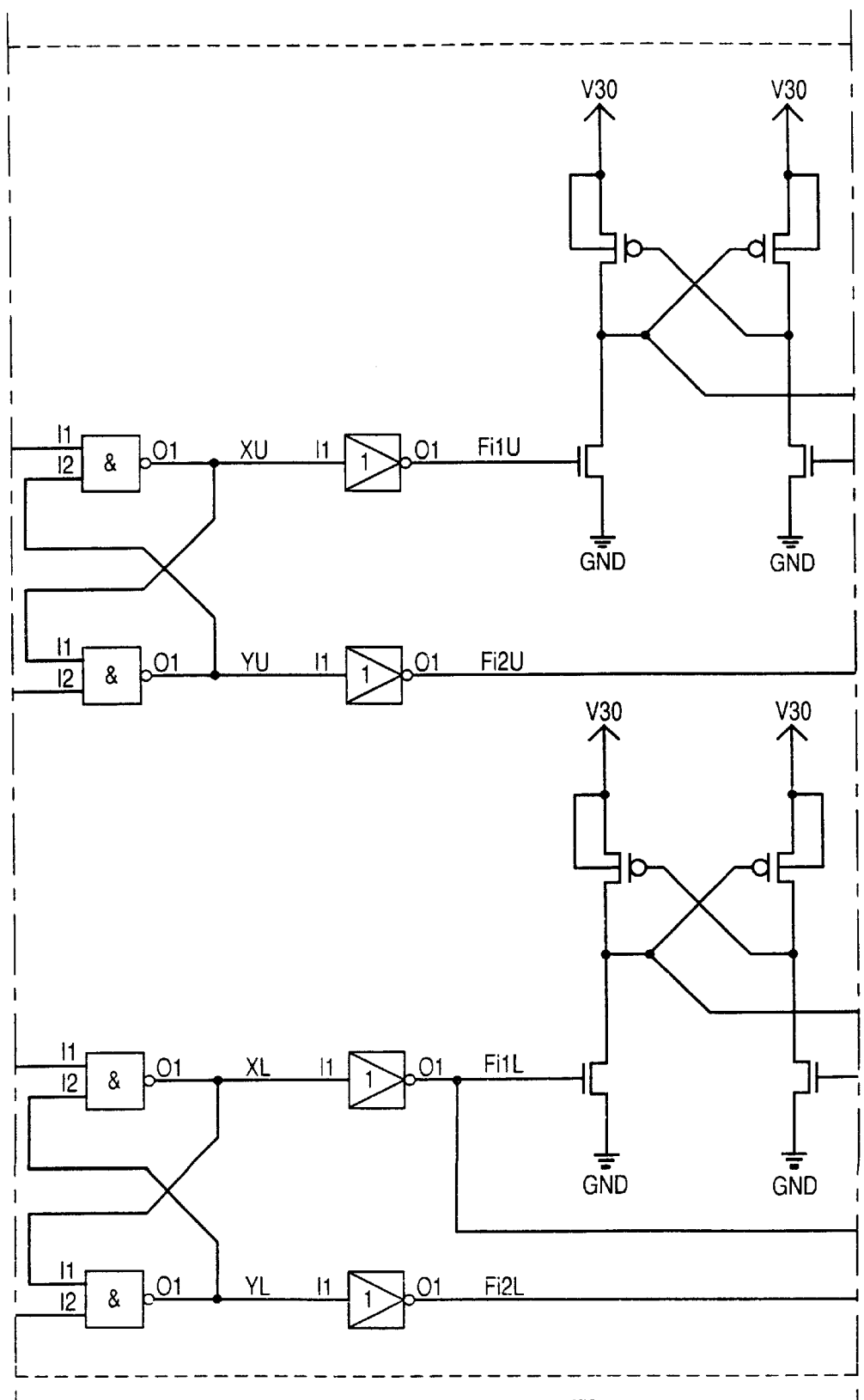
Fig.7 (Part II)

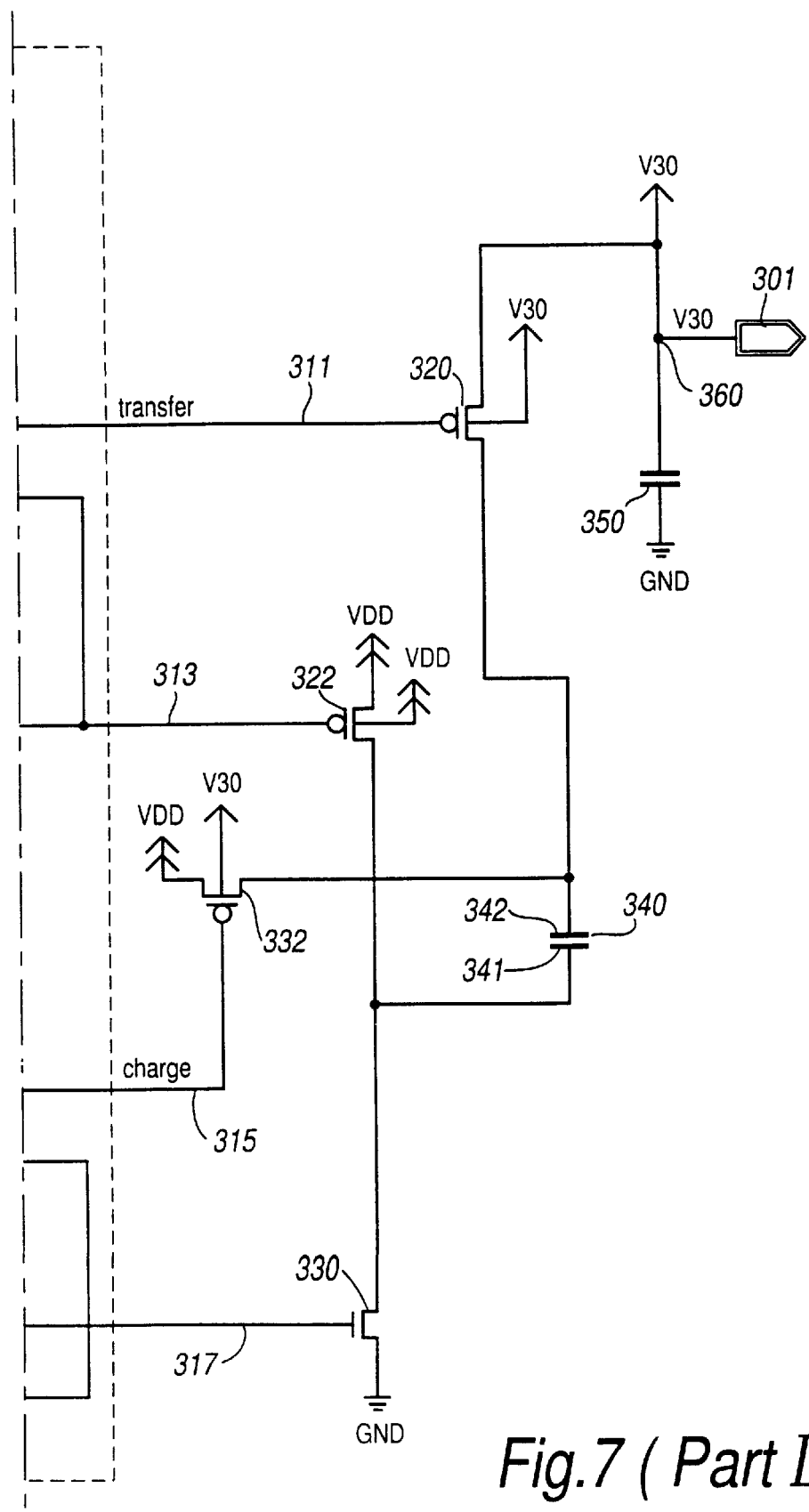
Fig.7 (Part III)

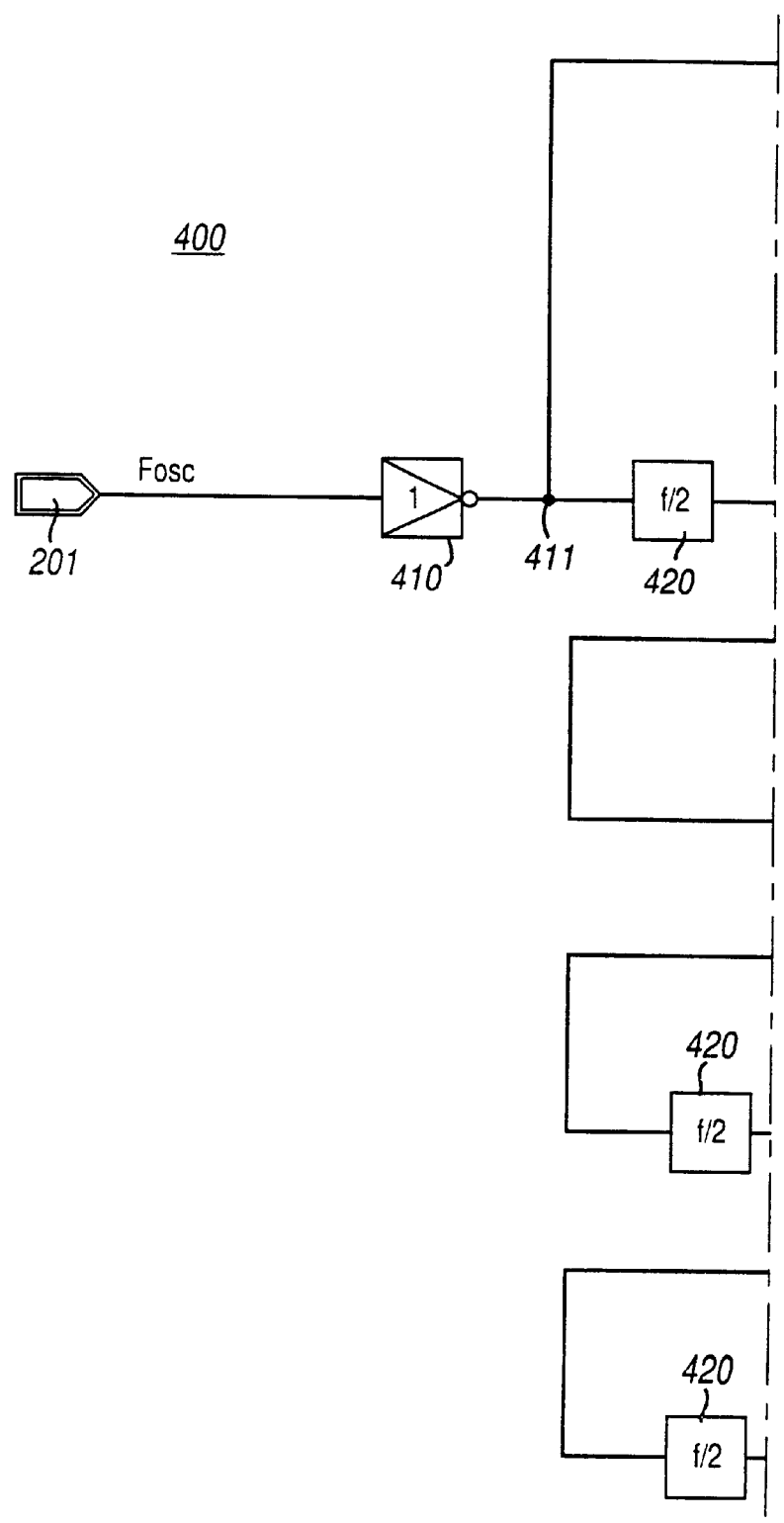
Fig.8 (Part I)

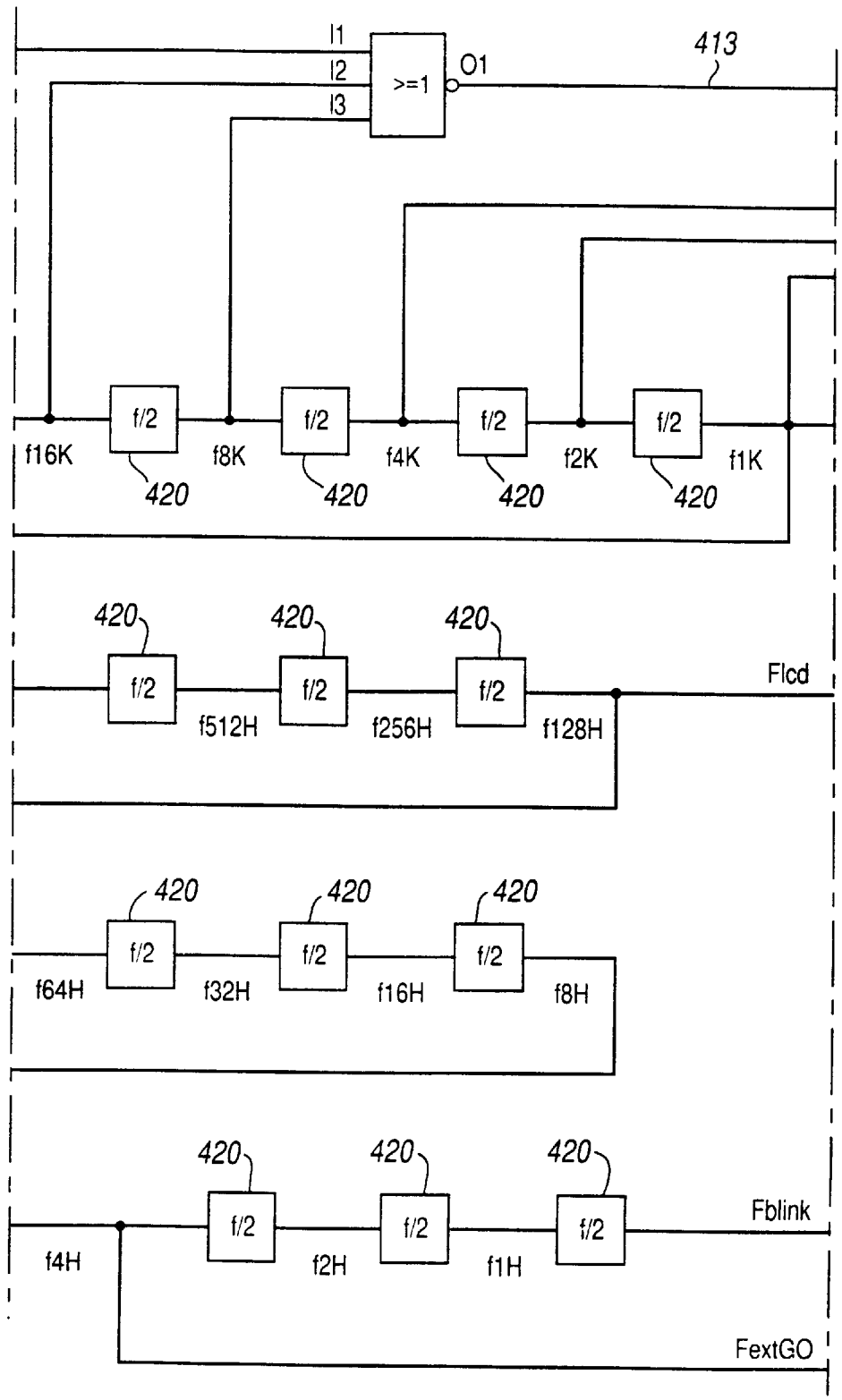
Fig.8 (Part II)

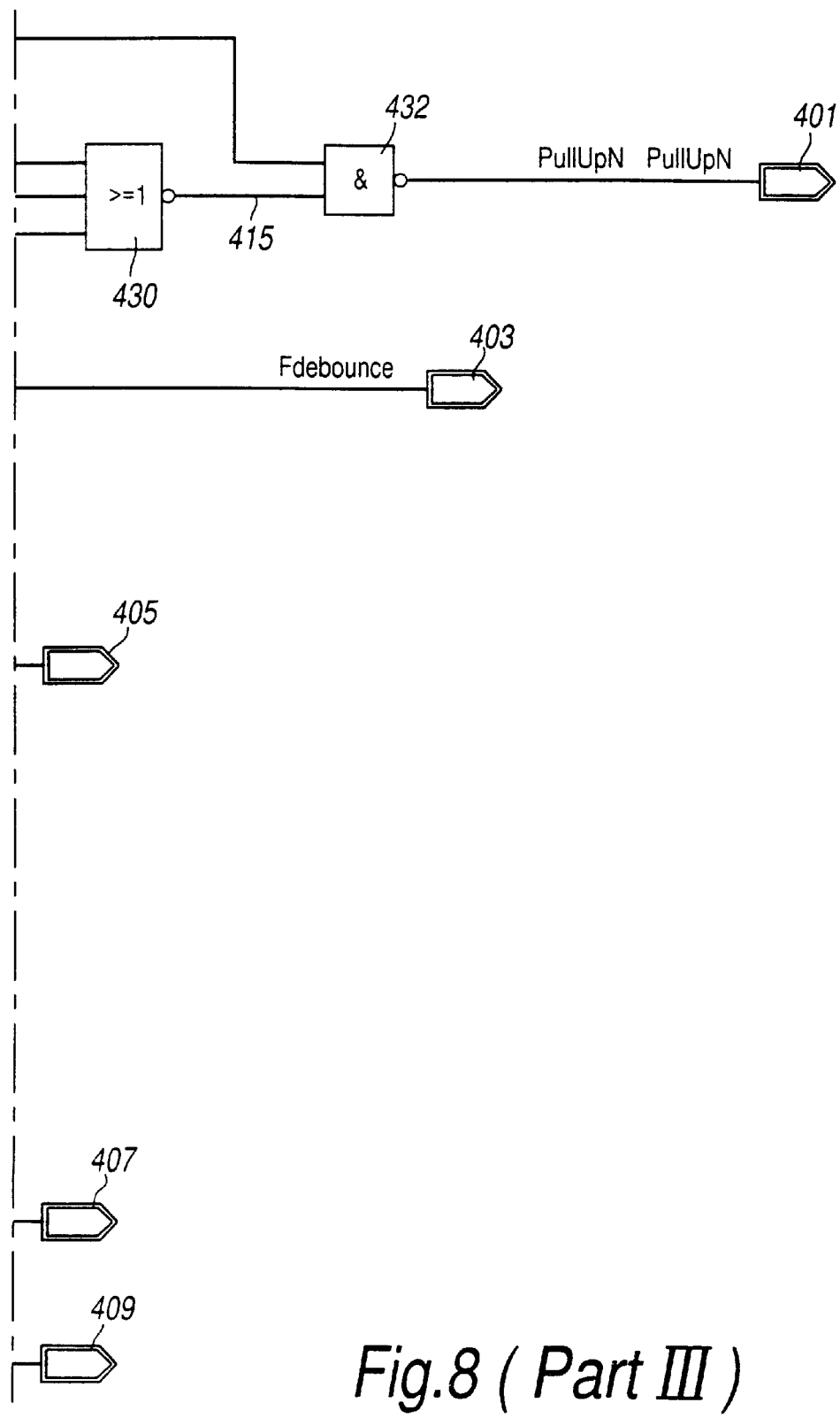
Fig.8 ( Part III )

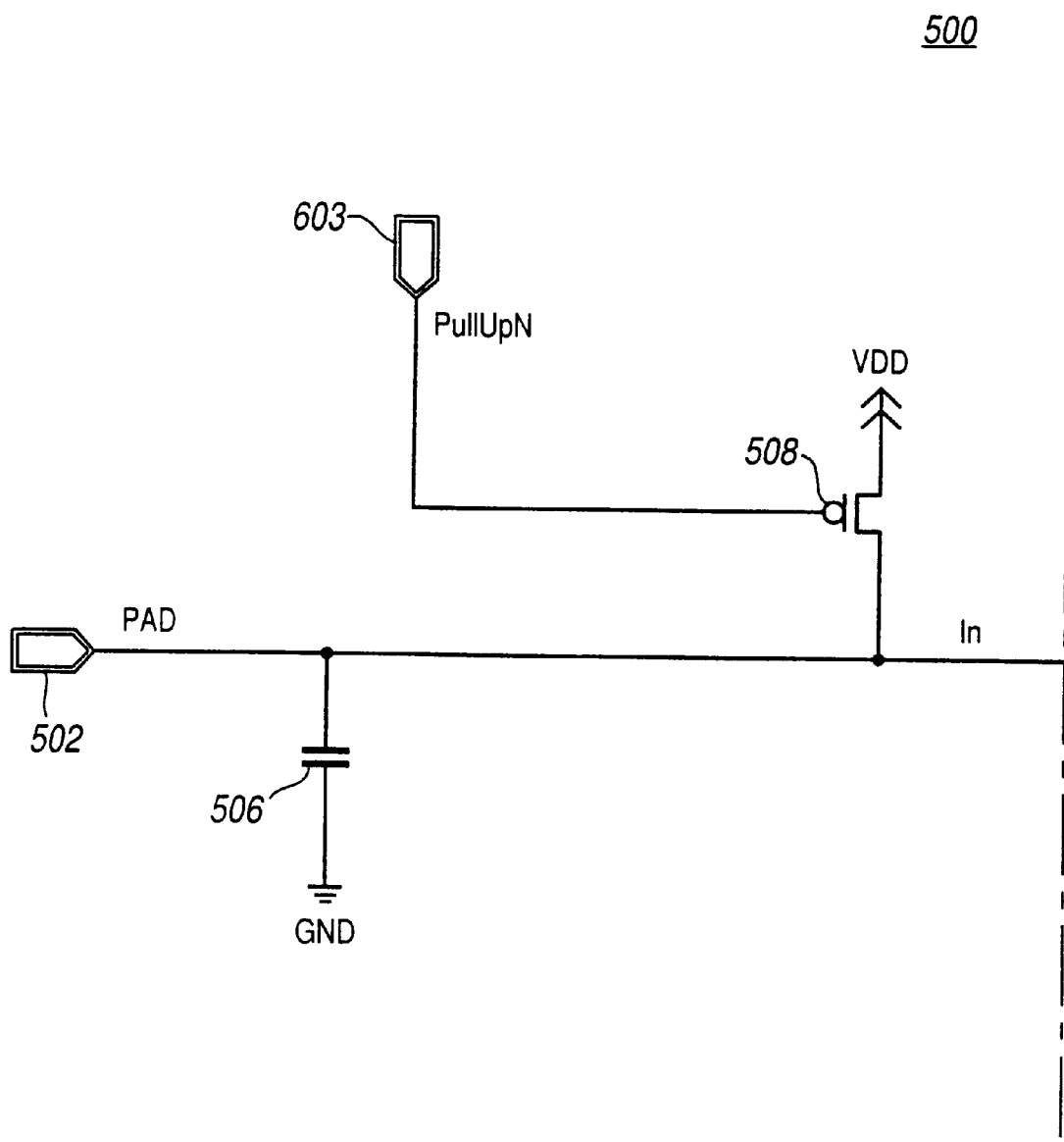
Fig.9 ( Part I )

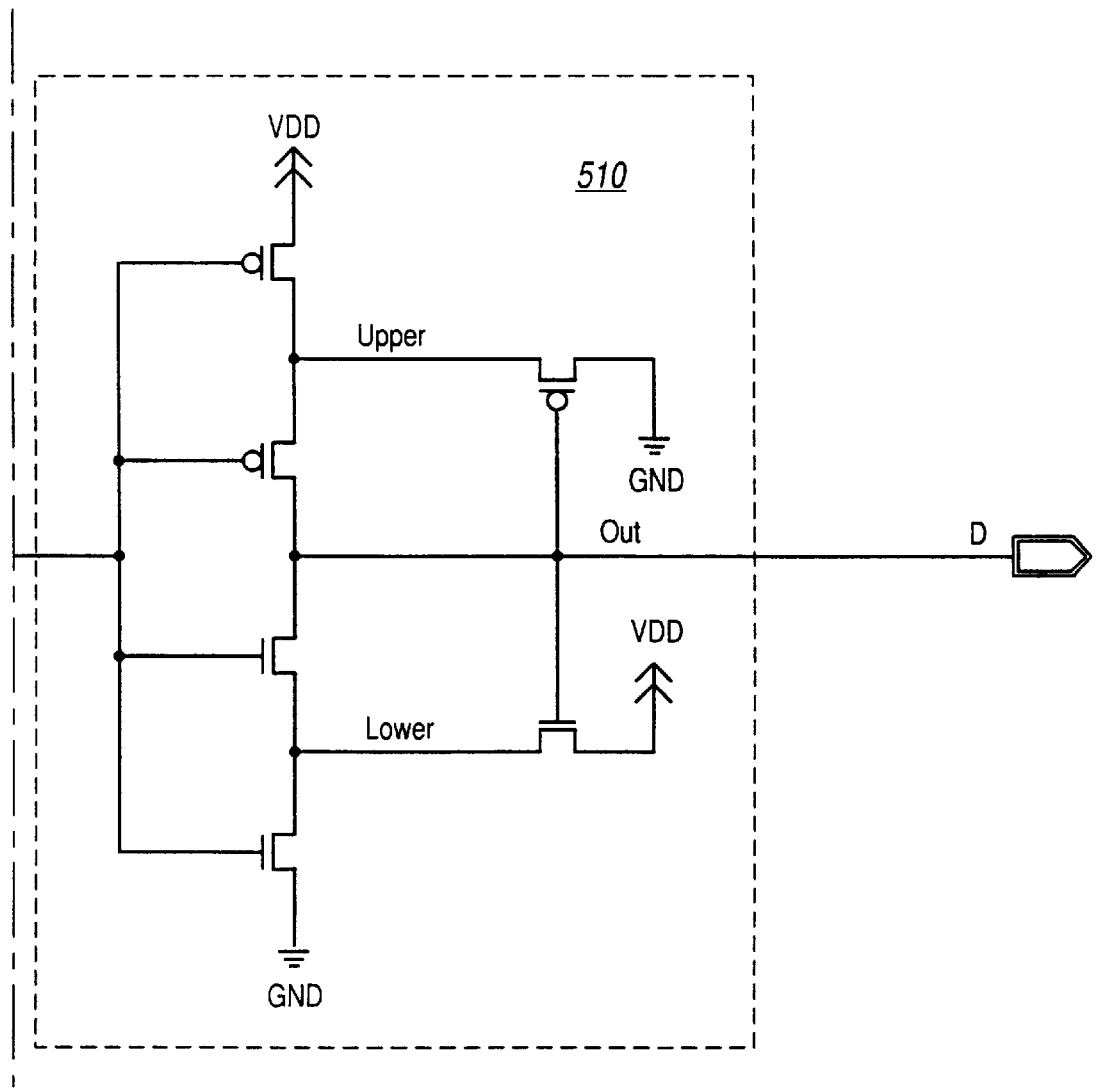
Fig.9 (Part II)

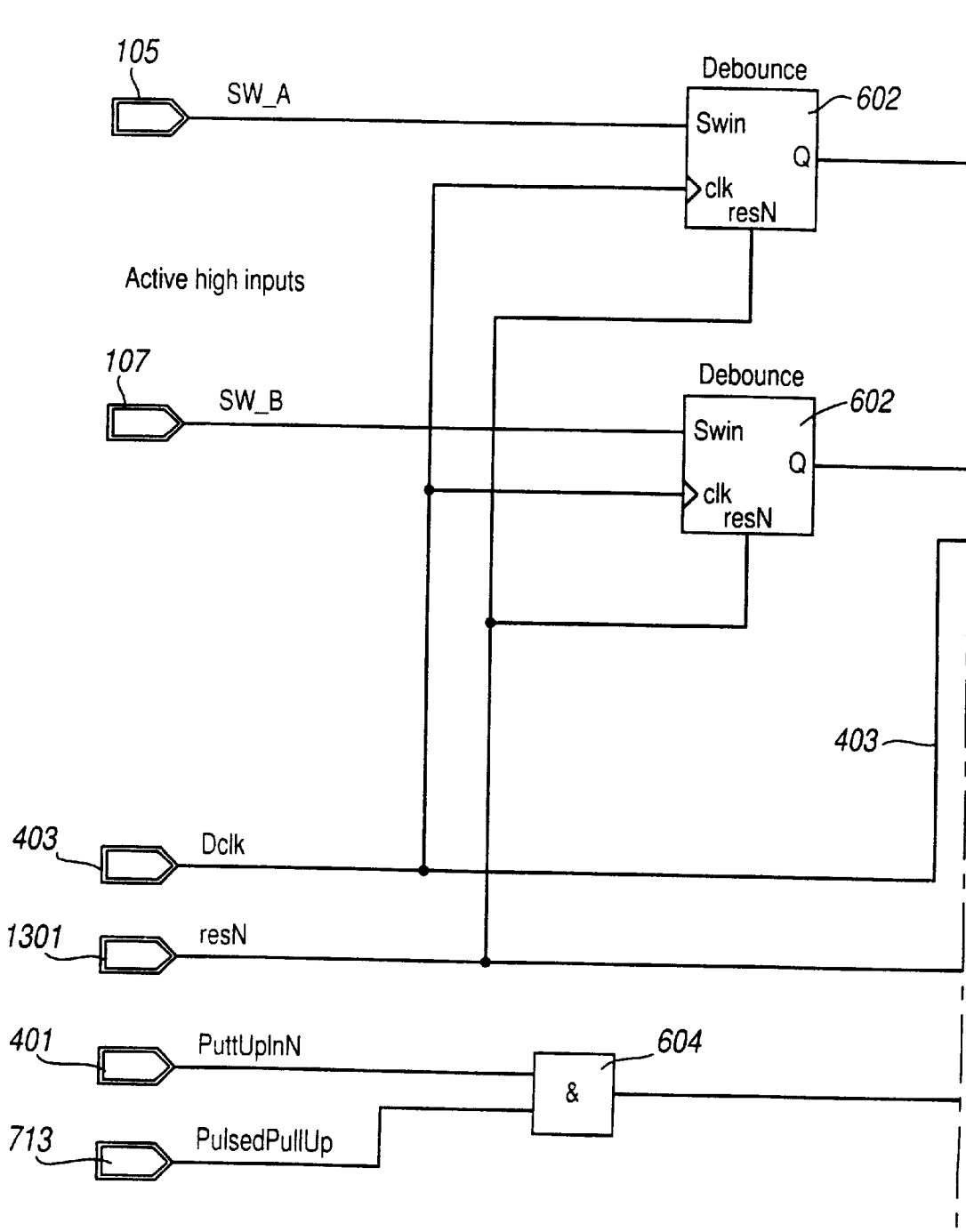
Fig. 10 (Part I)

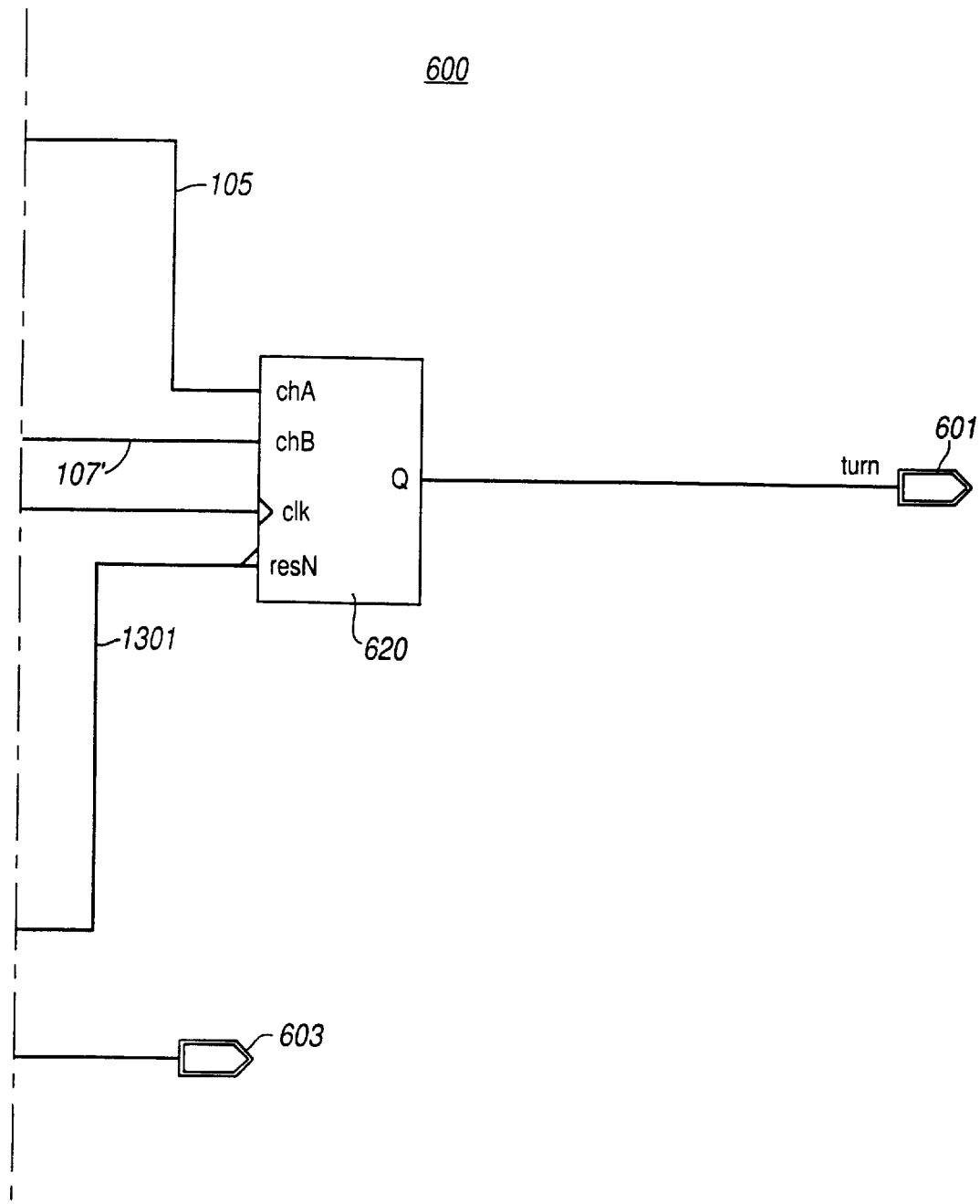
Fig.10 (Part II)

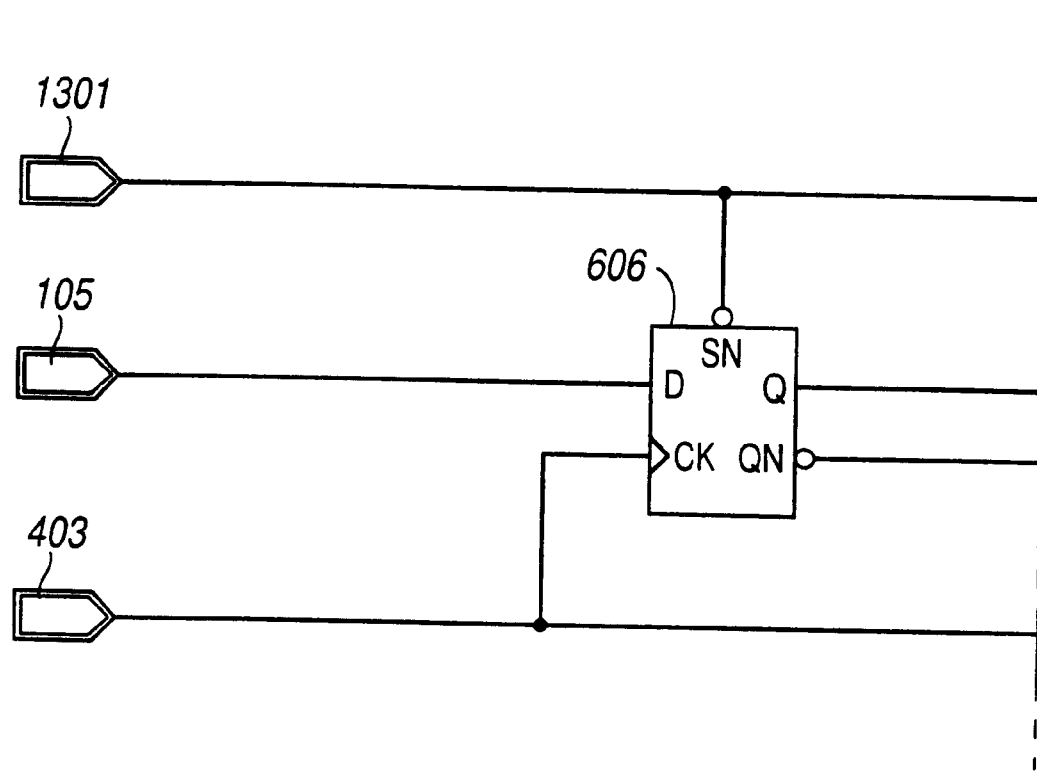
Fig.11 (Part I)

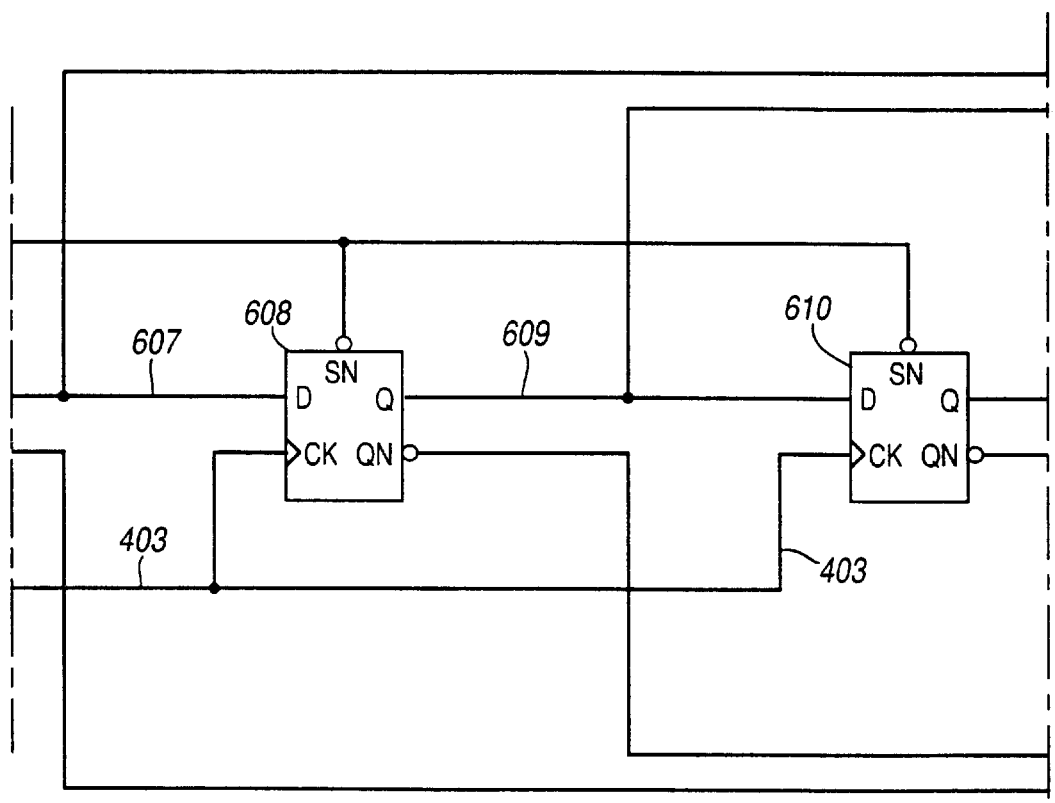
Fig.11 ( Part II )

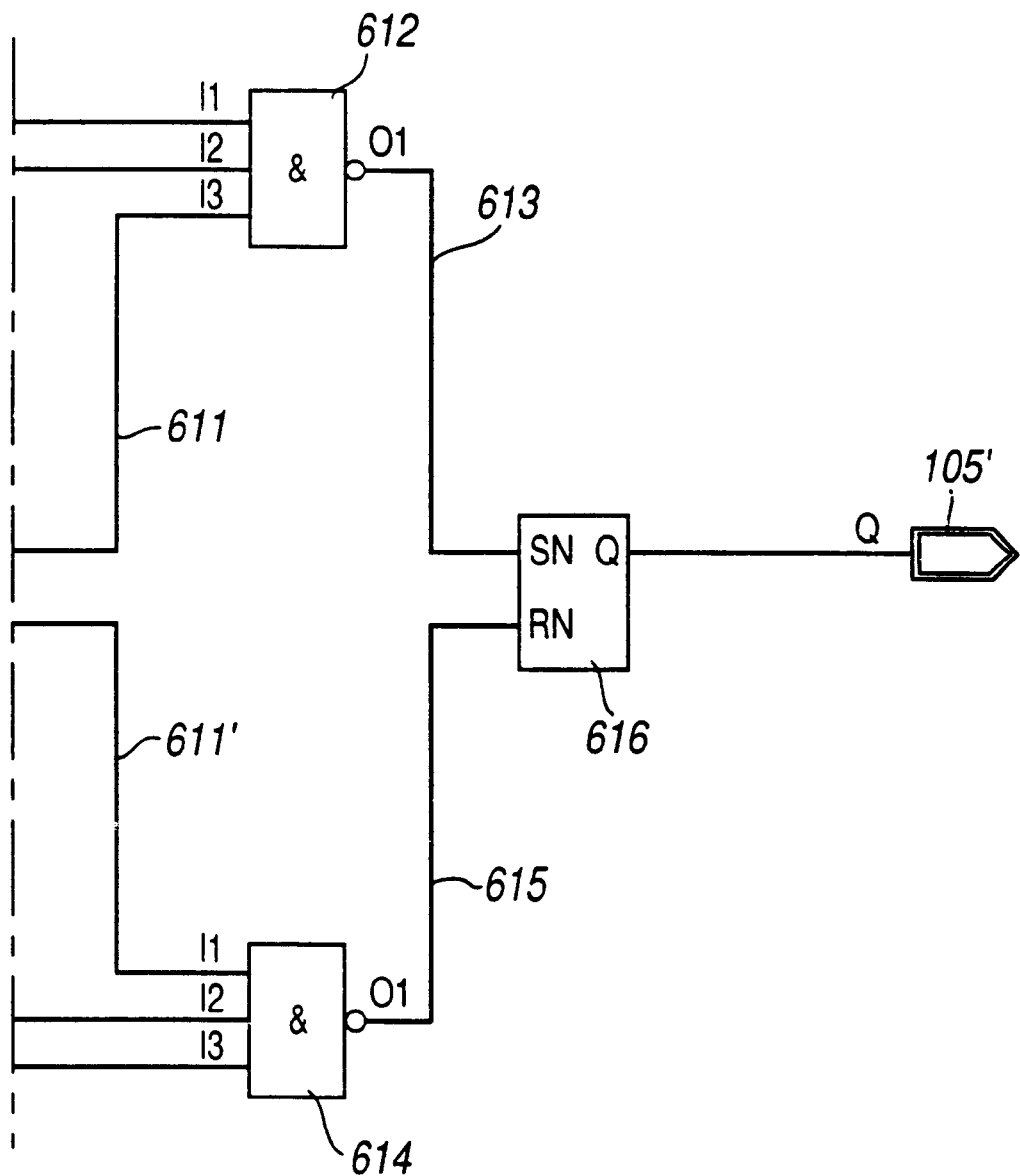
Fig.11 (Part III)

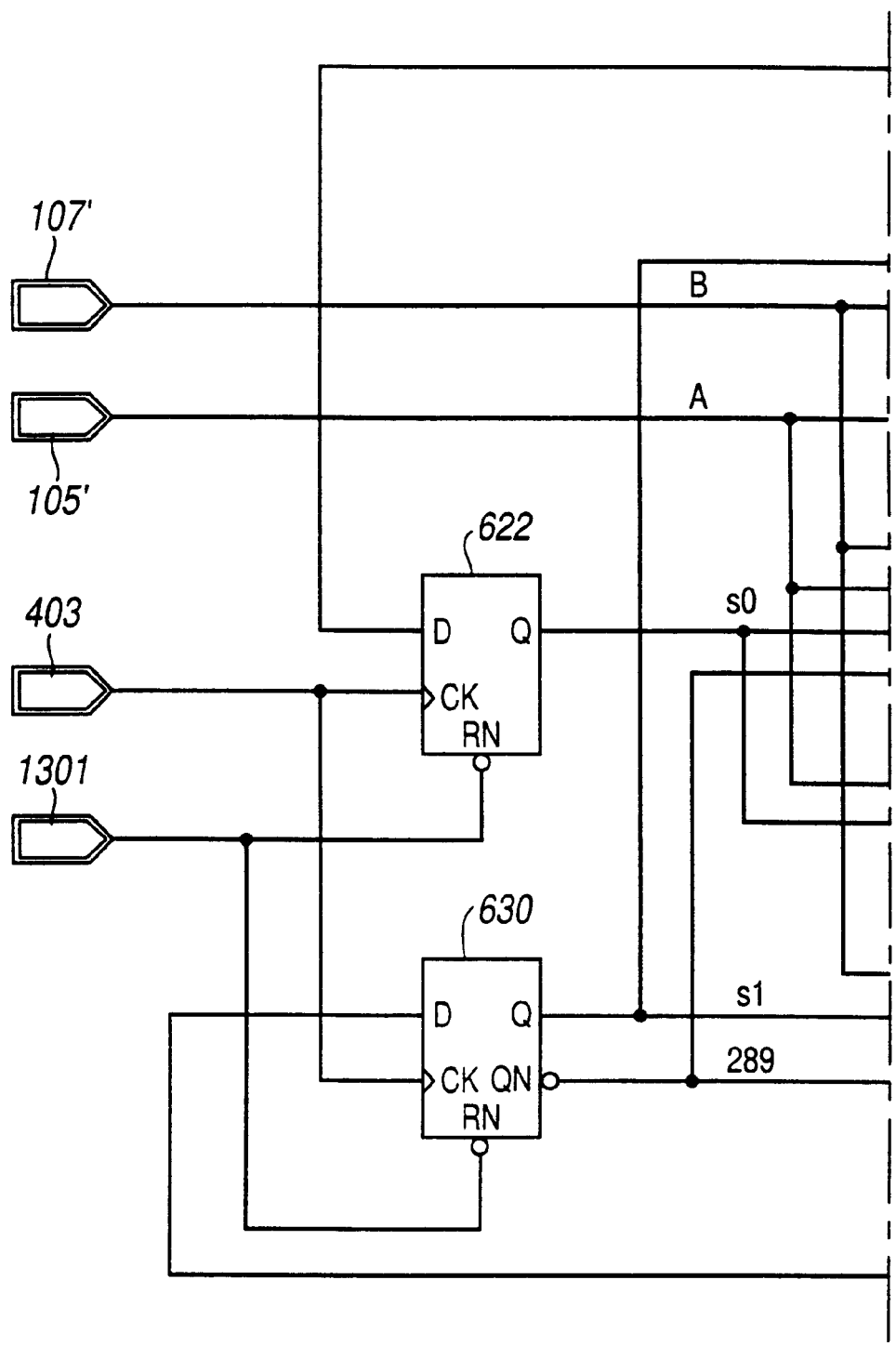
Fig.12 (Part I)

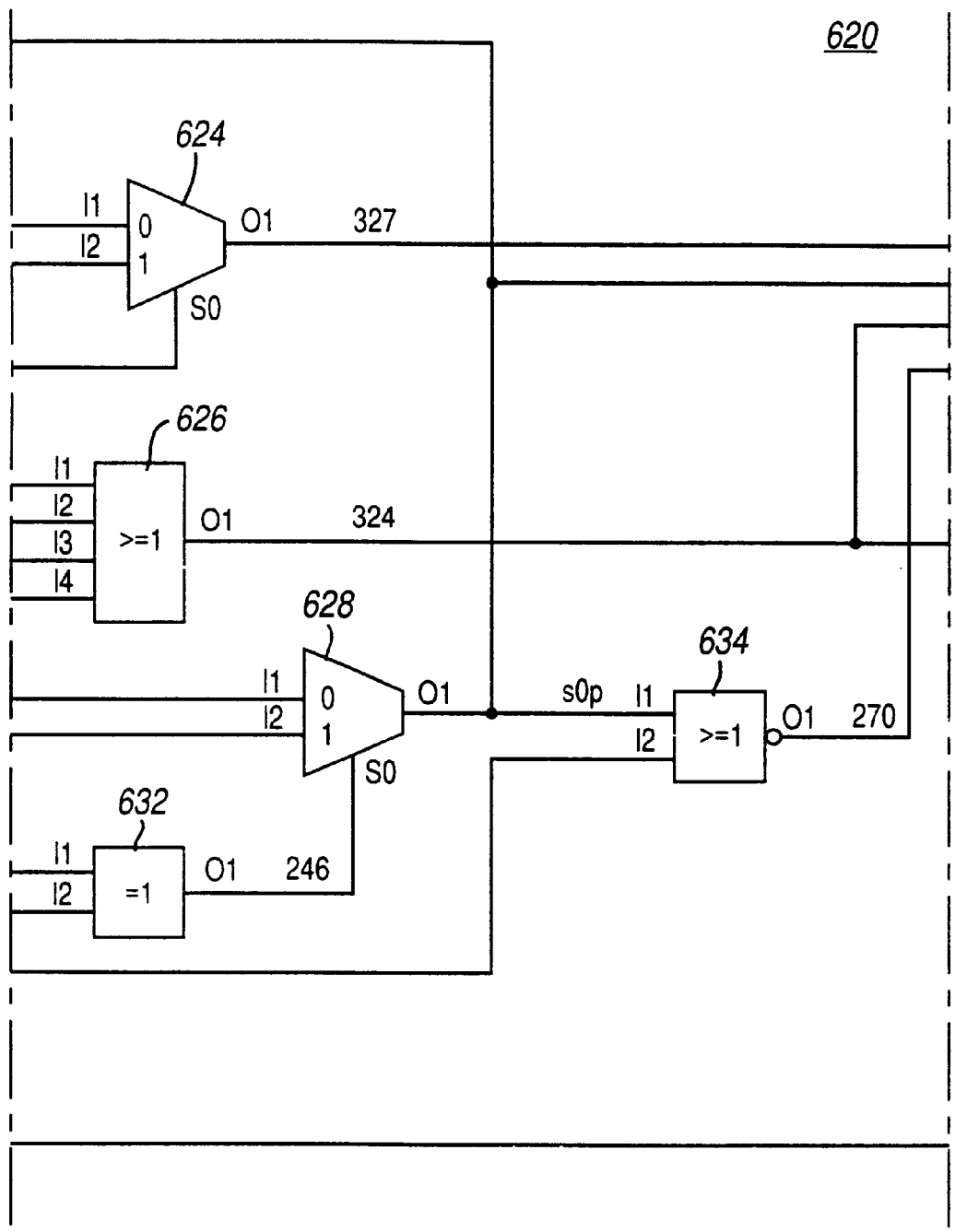
Fig. 12 (Part II)

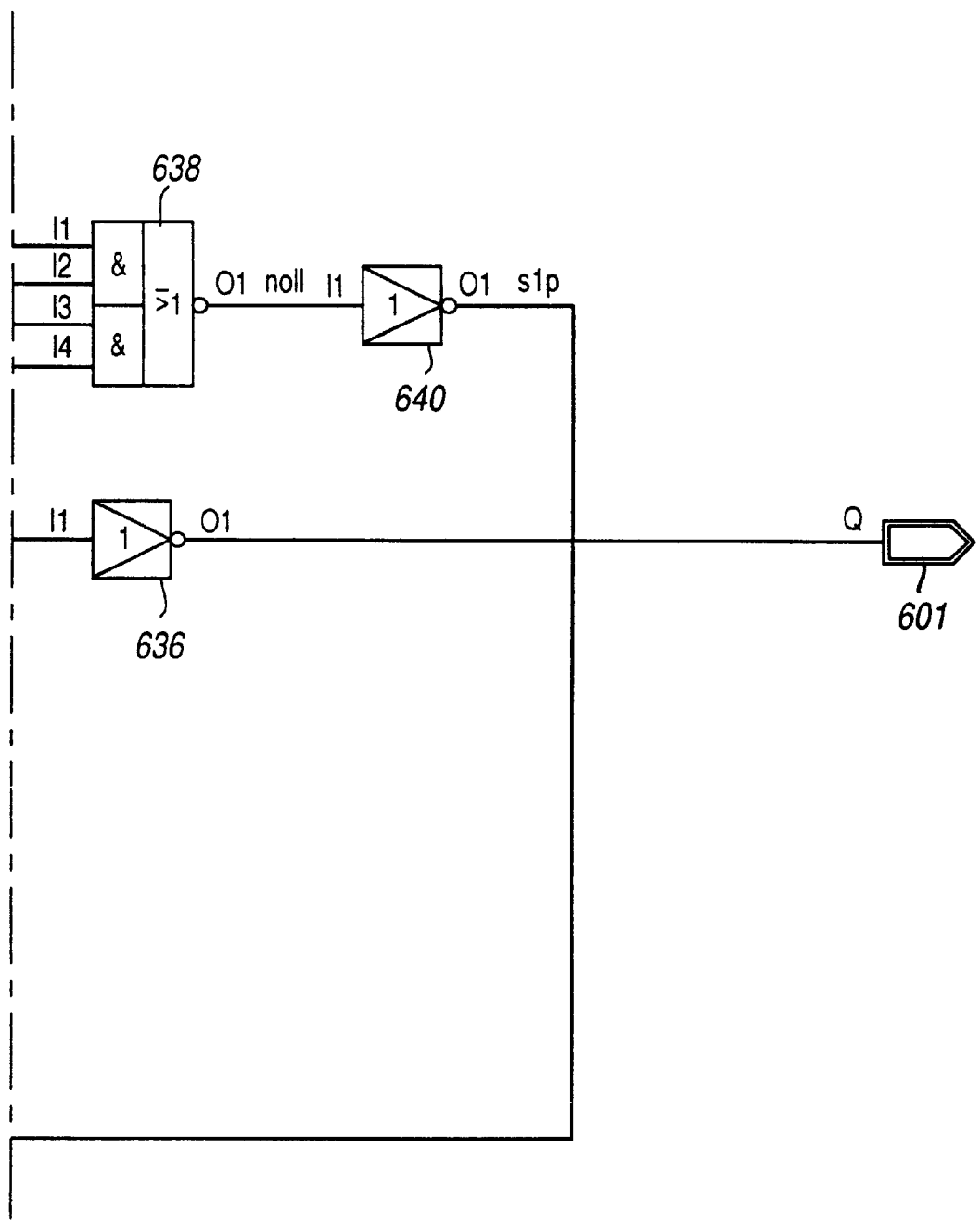
Fig.12 (Part III)

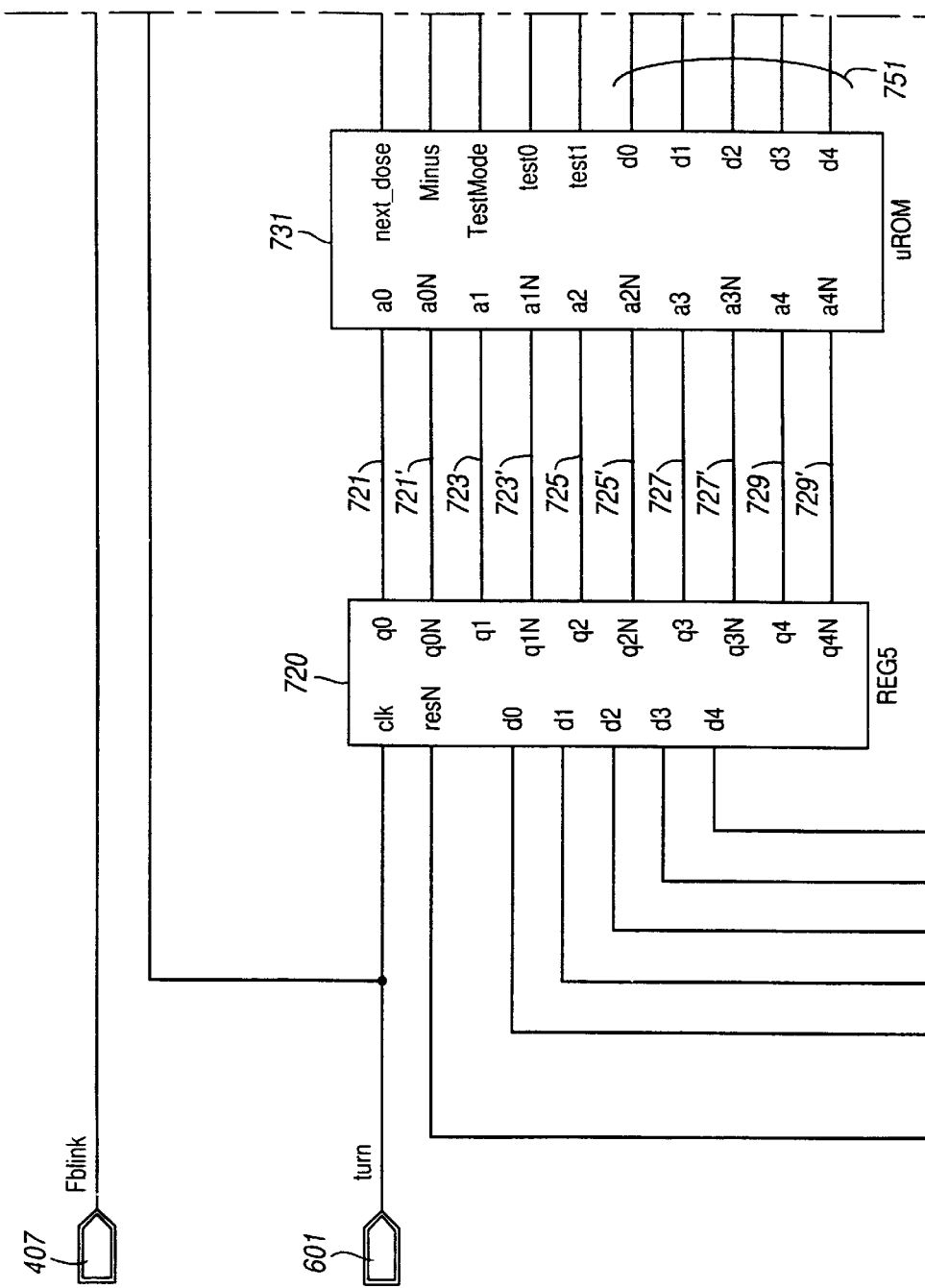
Fig. 13 (Part I)

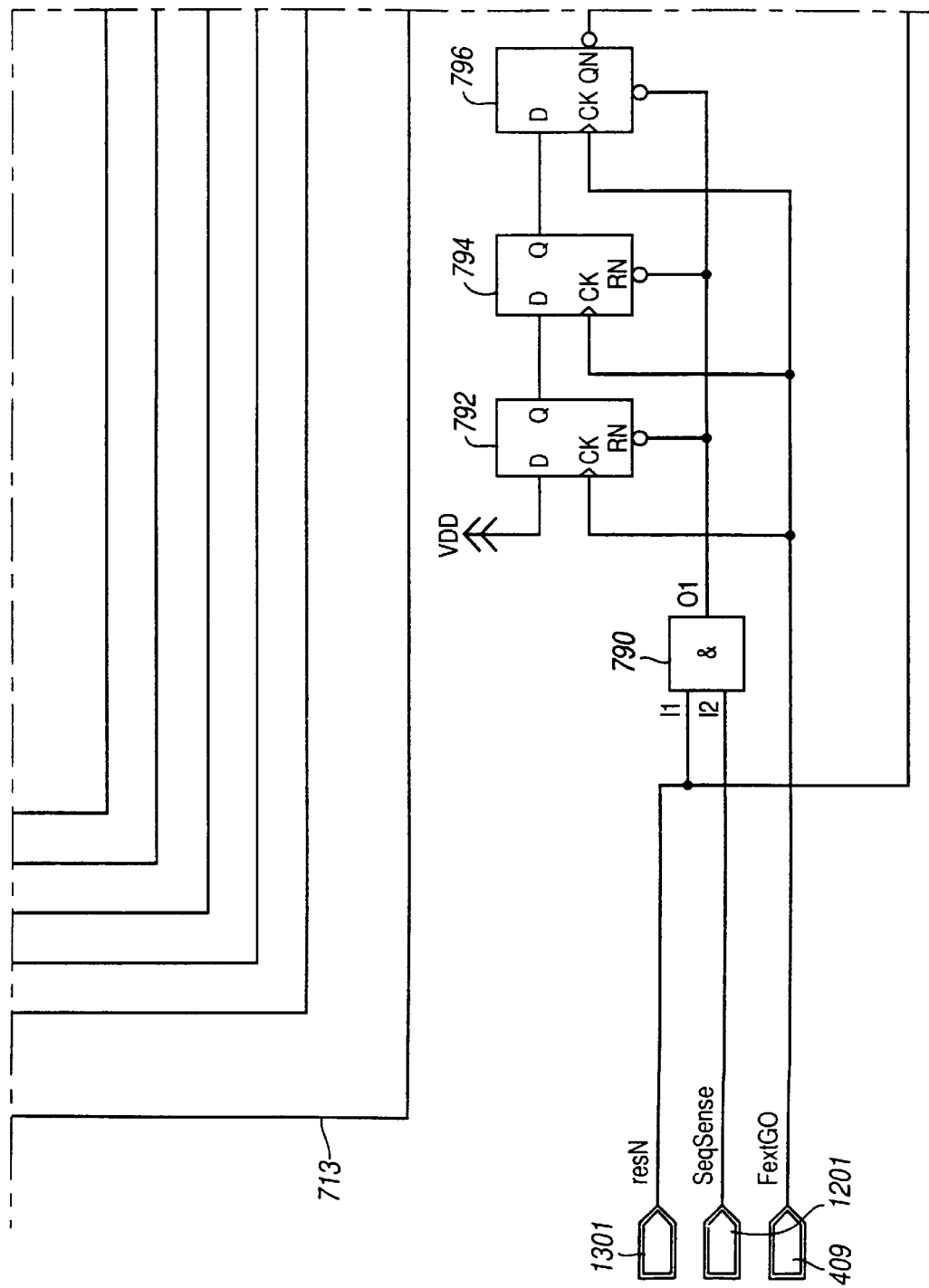
Fig.13 (Part II)

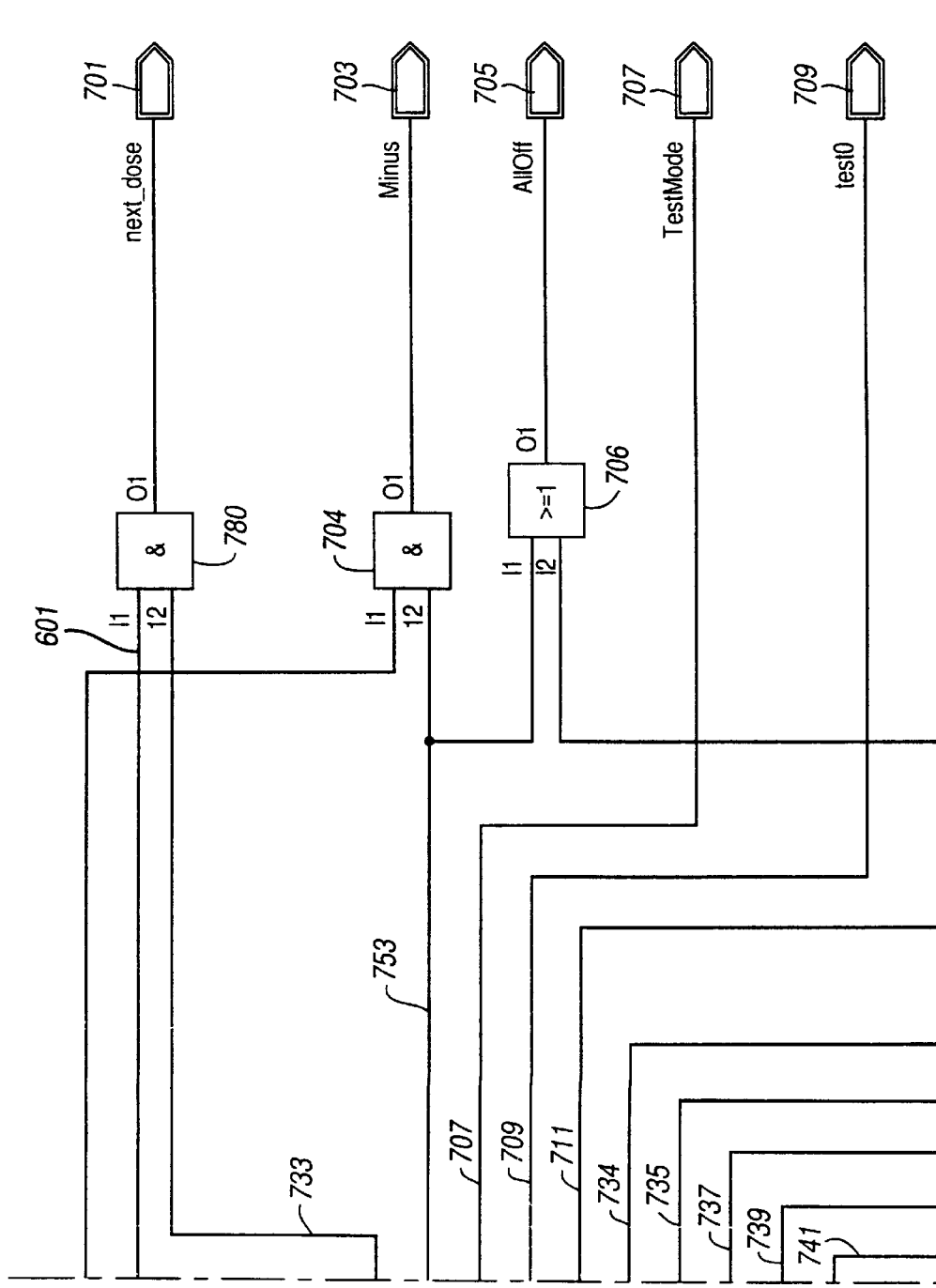
Fig.13 (Part III)

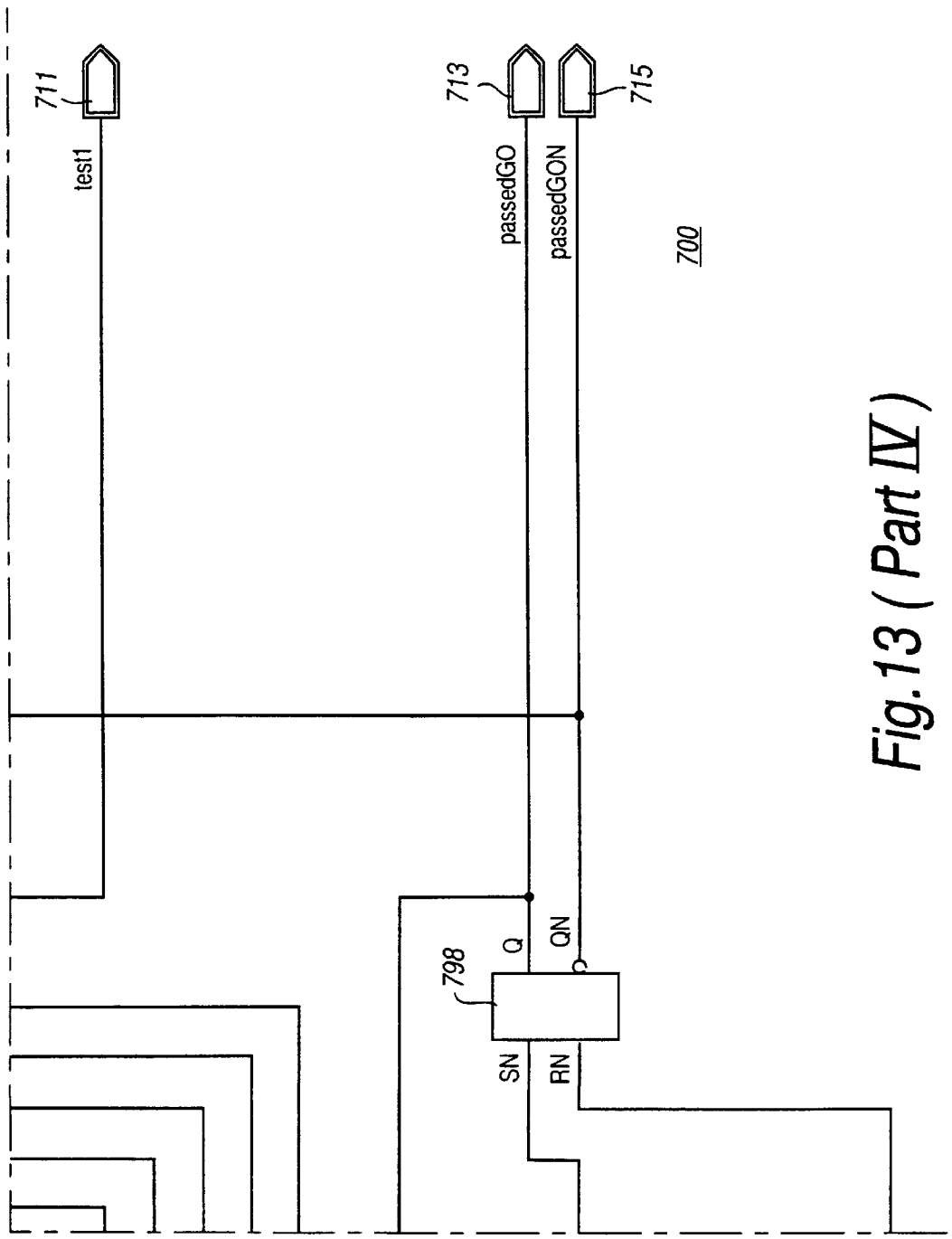
Fig. 13 (Part IV)

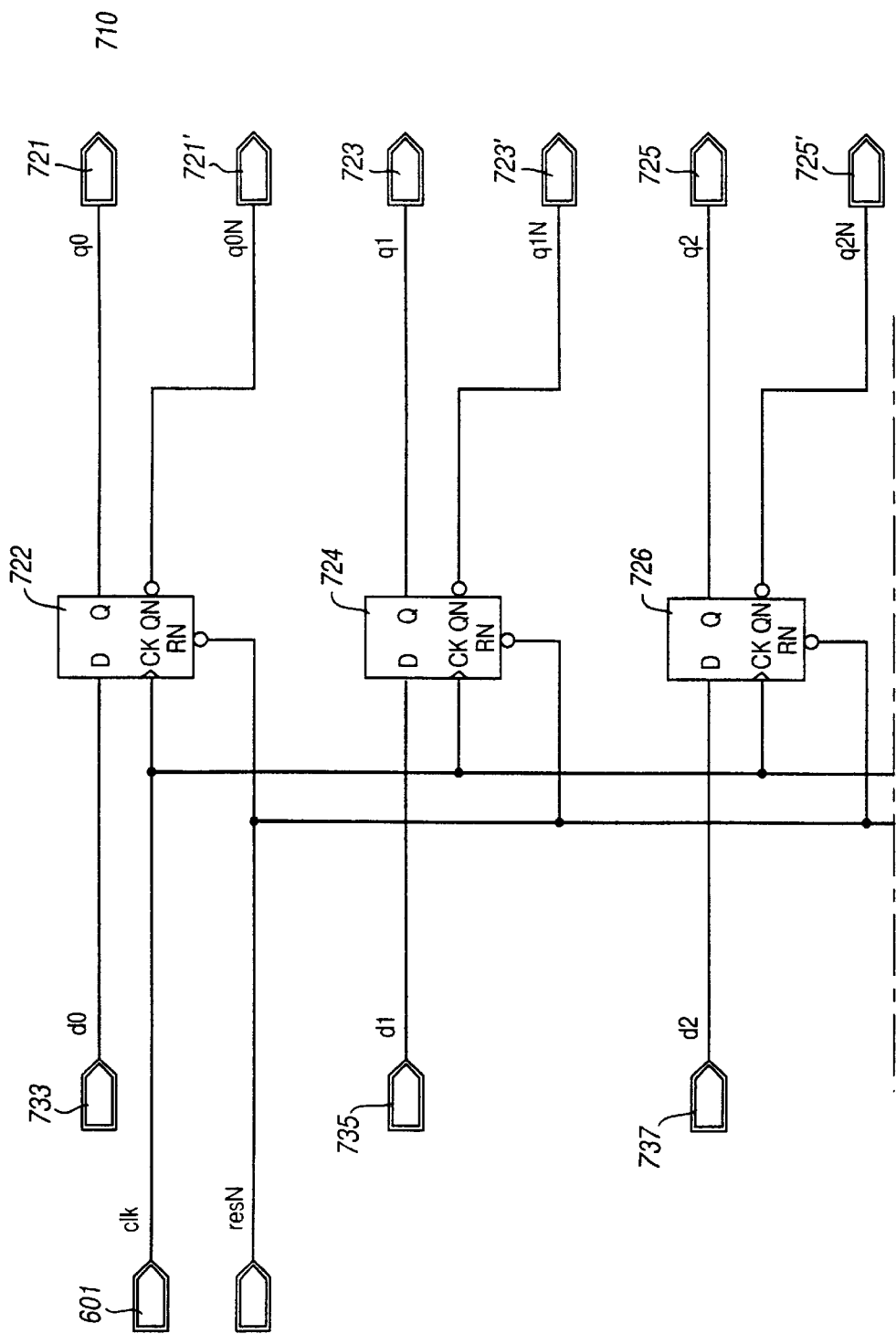
Fig. 14 (Part I)

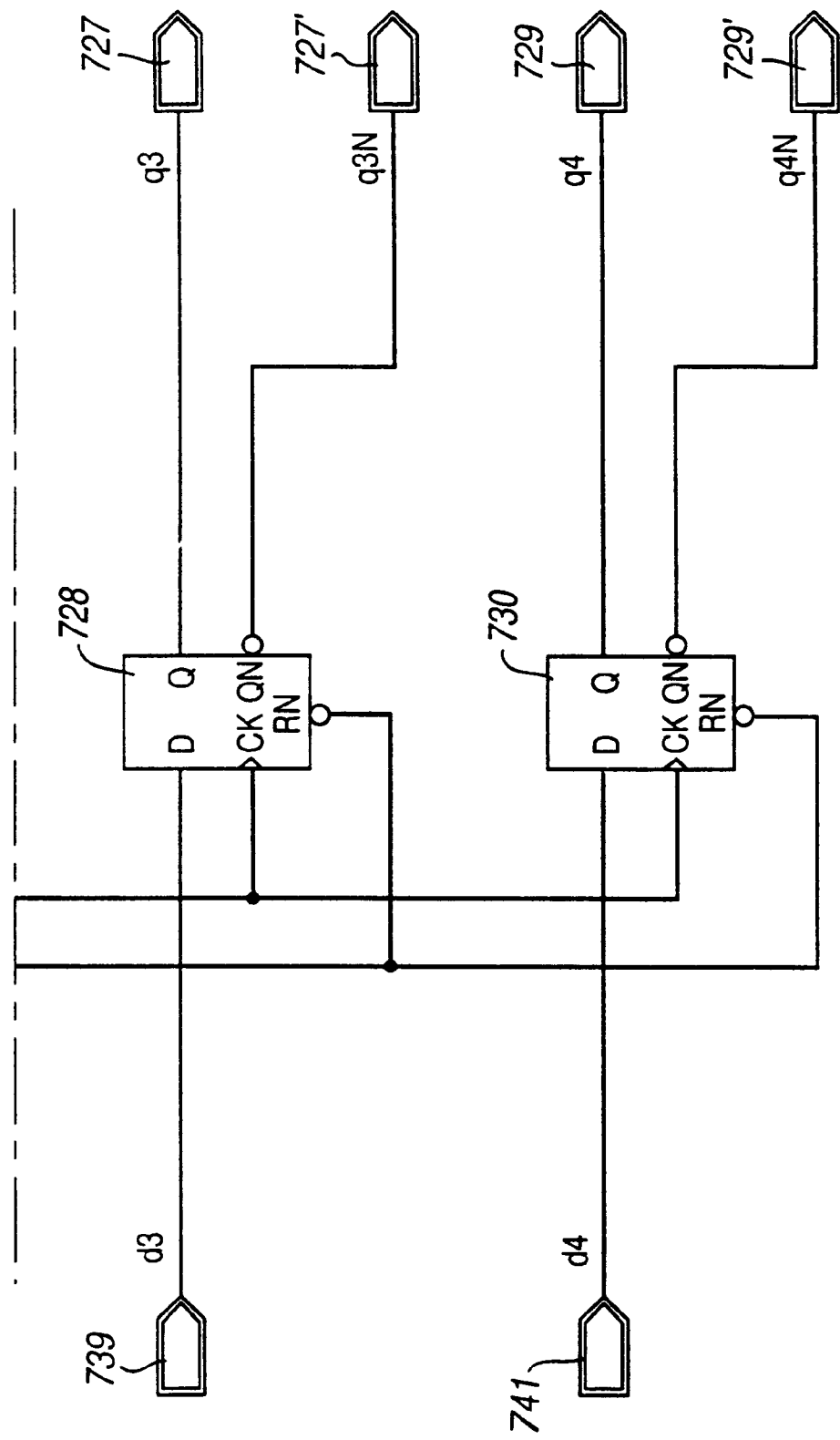
Fig.14 (Part II)

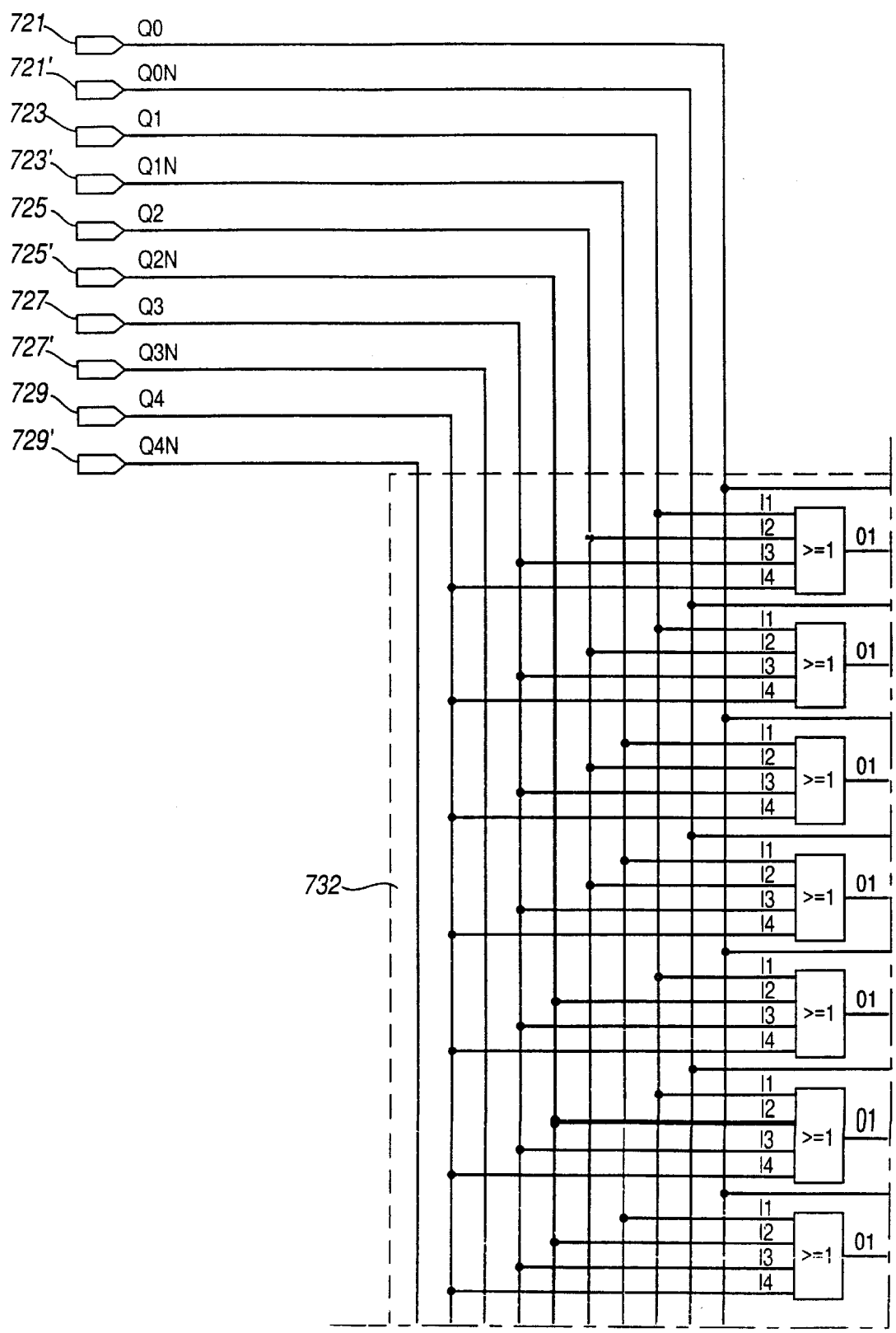
Fig.15 (Part I)

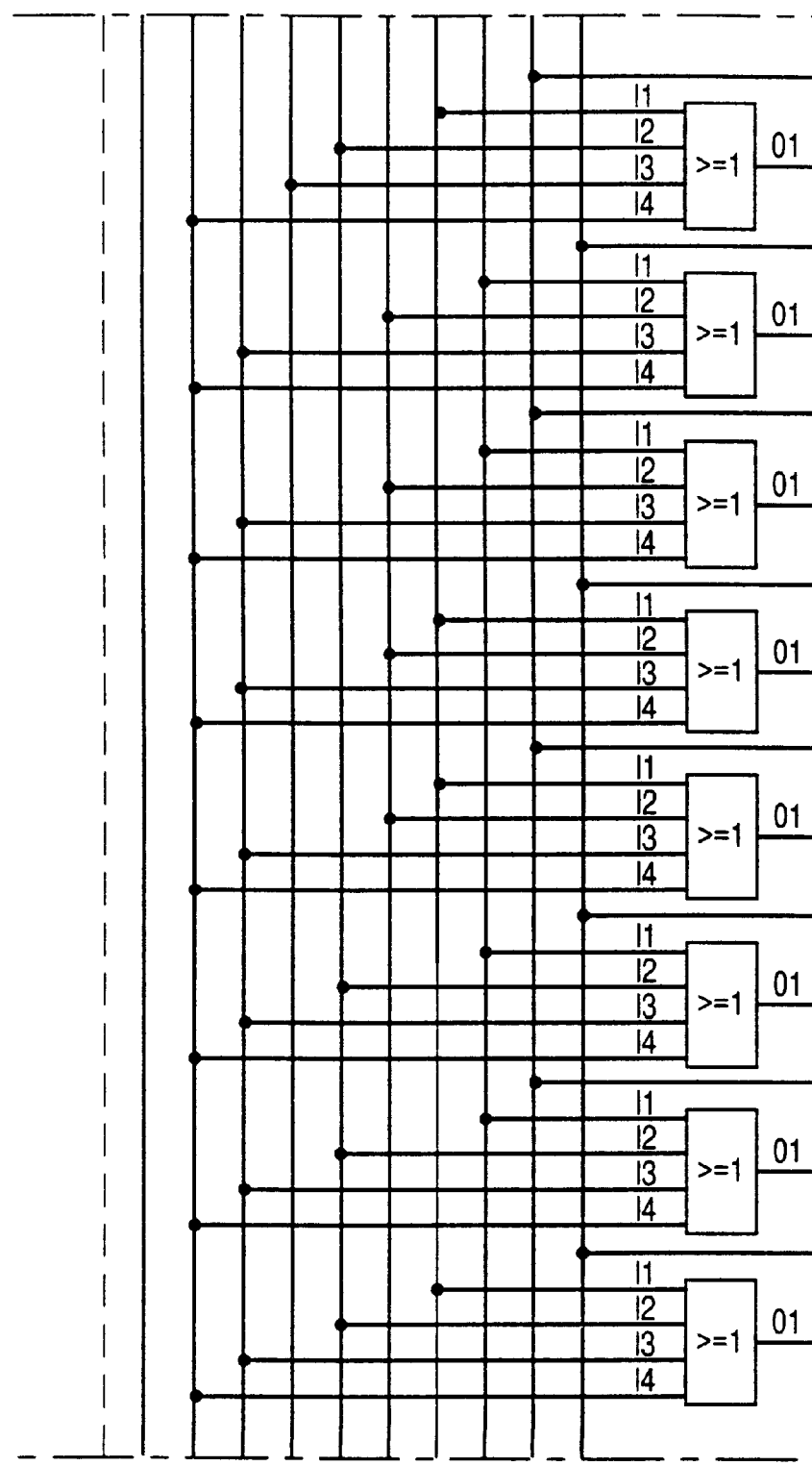
Fig.15 (Part II)

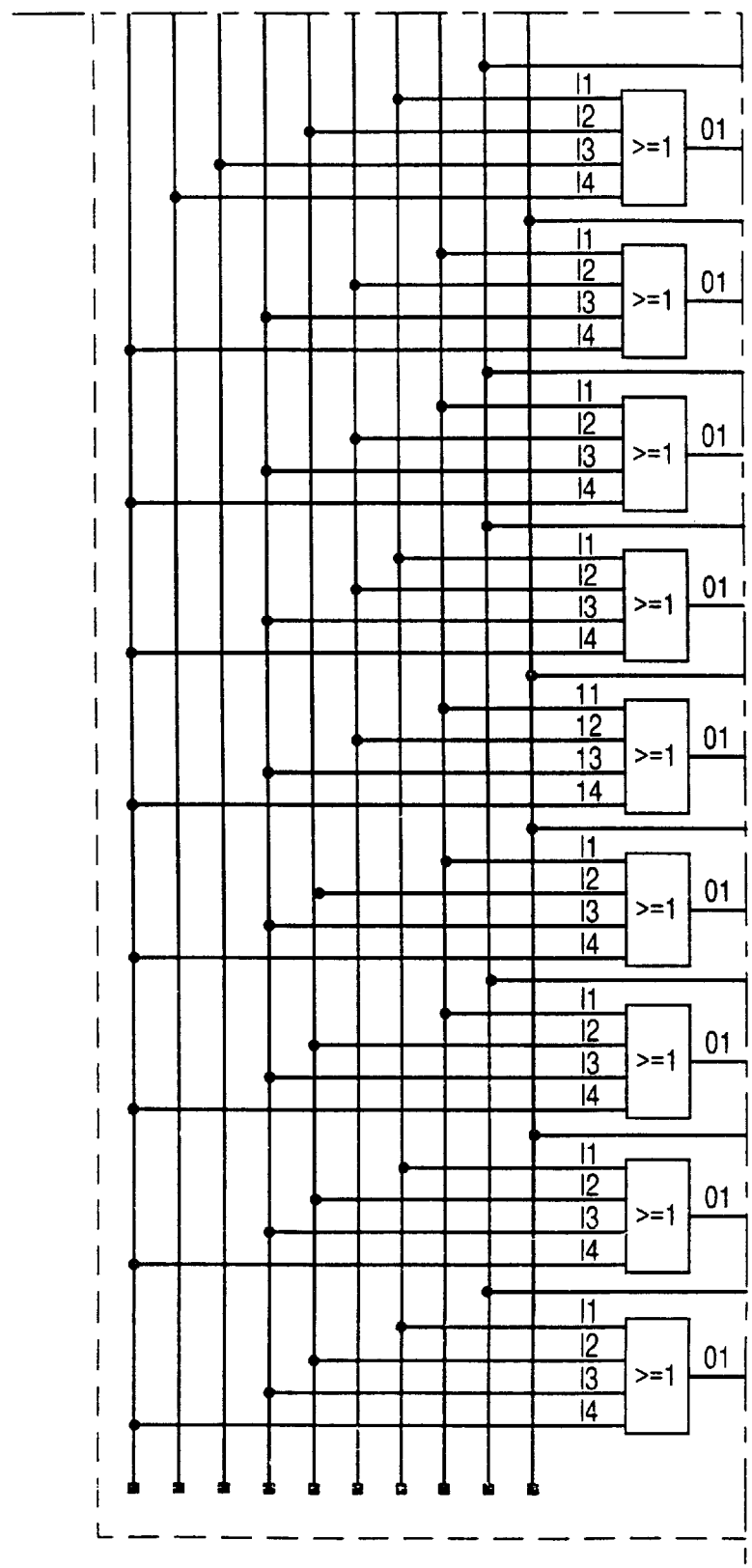
*Fig.15 (Part III)*

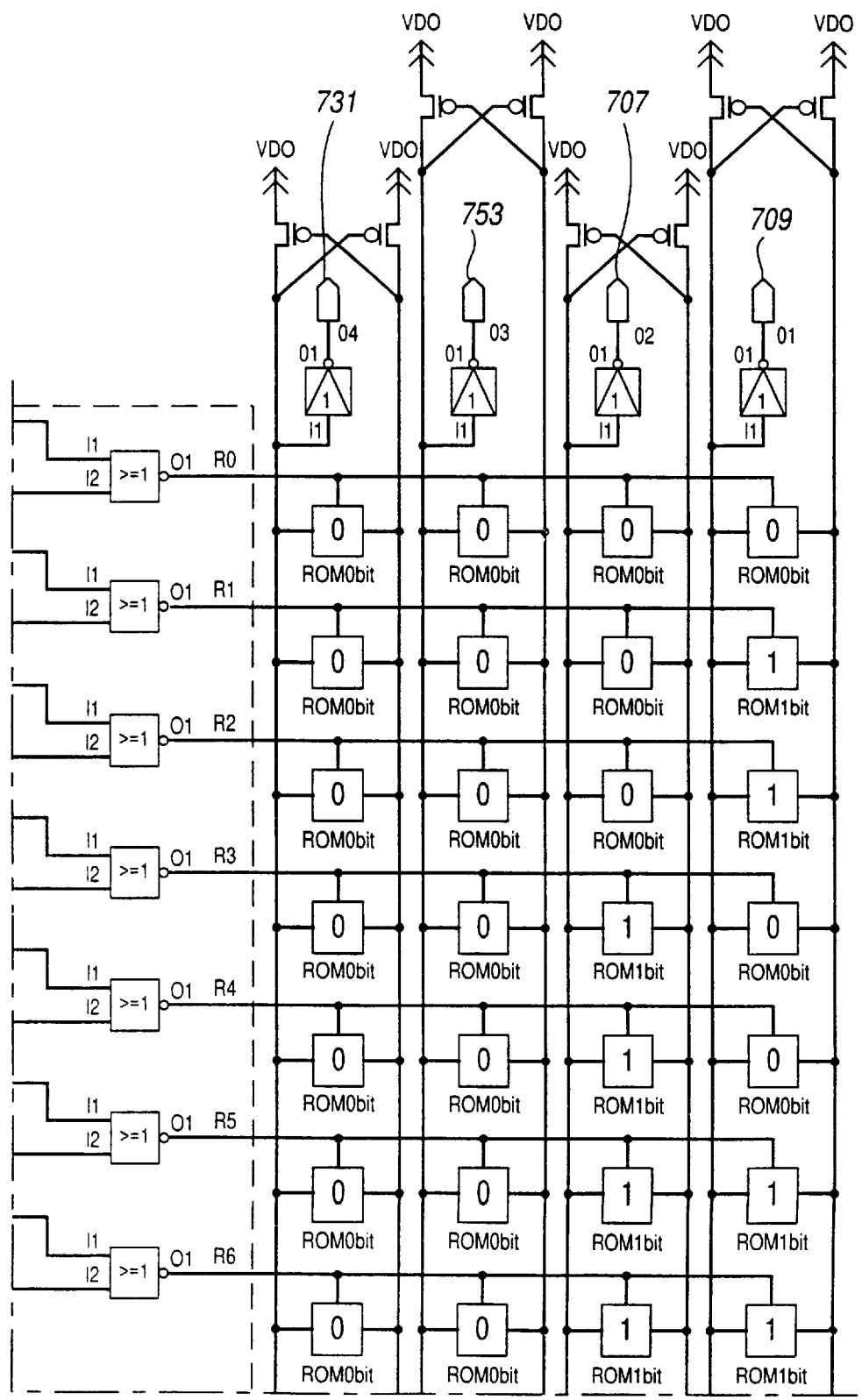
Fig.15 (Part IV)

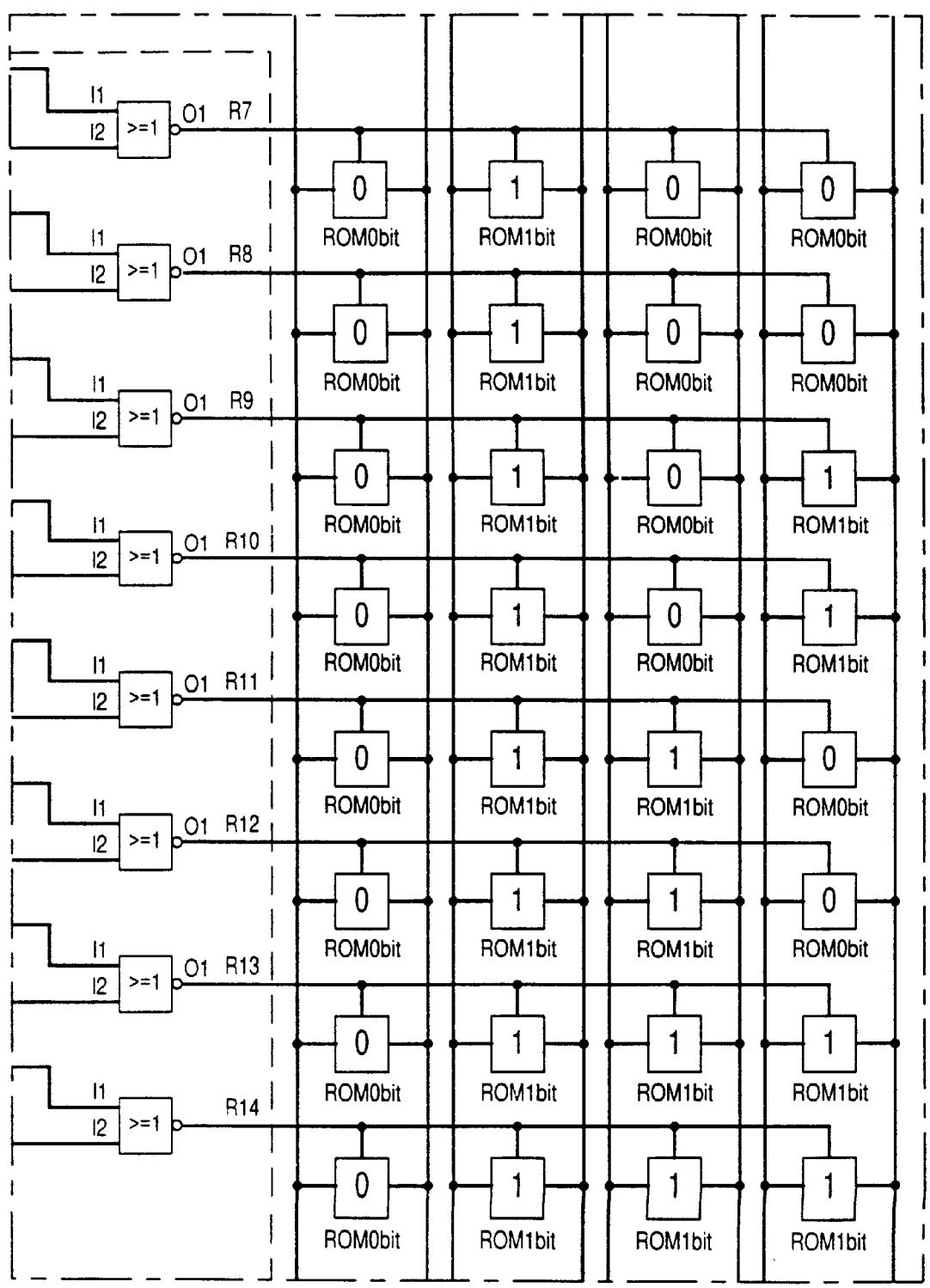
Fig.15 (Part V)

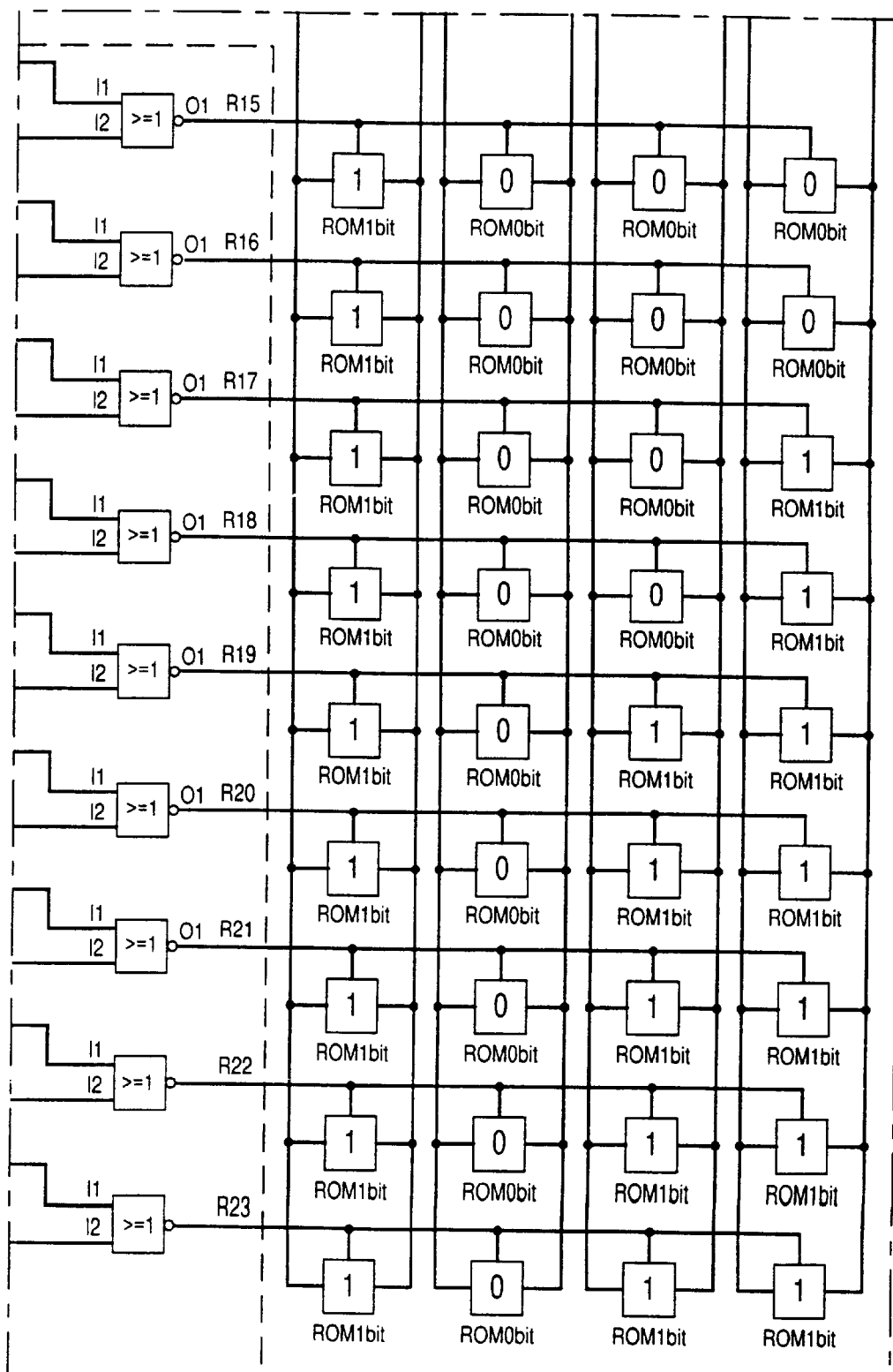
Fig.15 (Part VI)

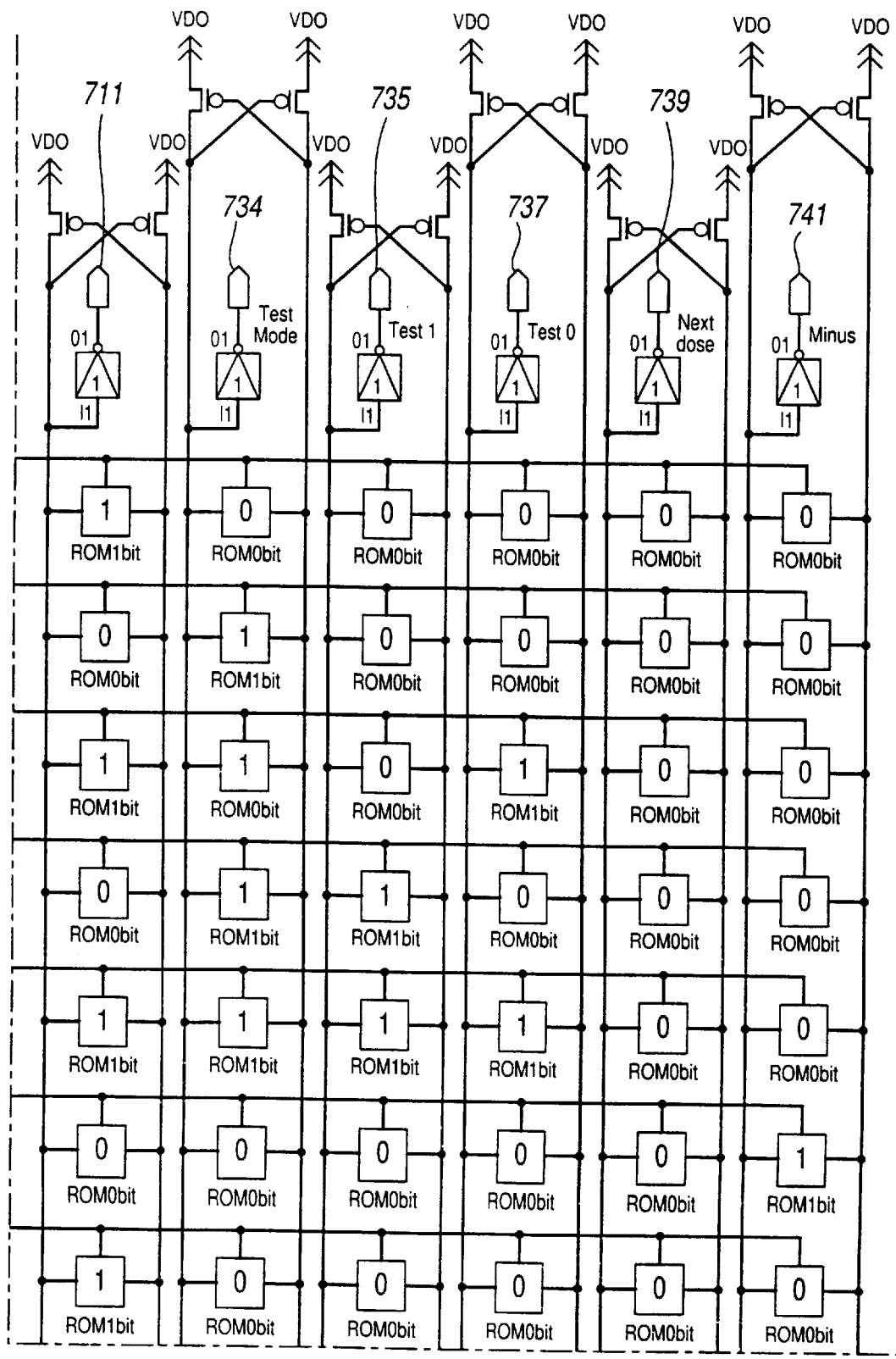
Fig.15 (Part VII)

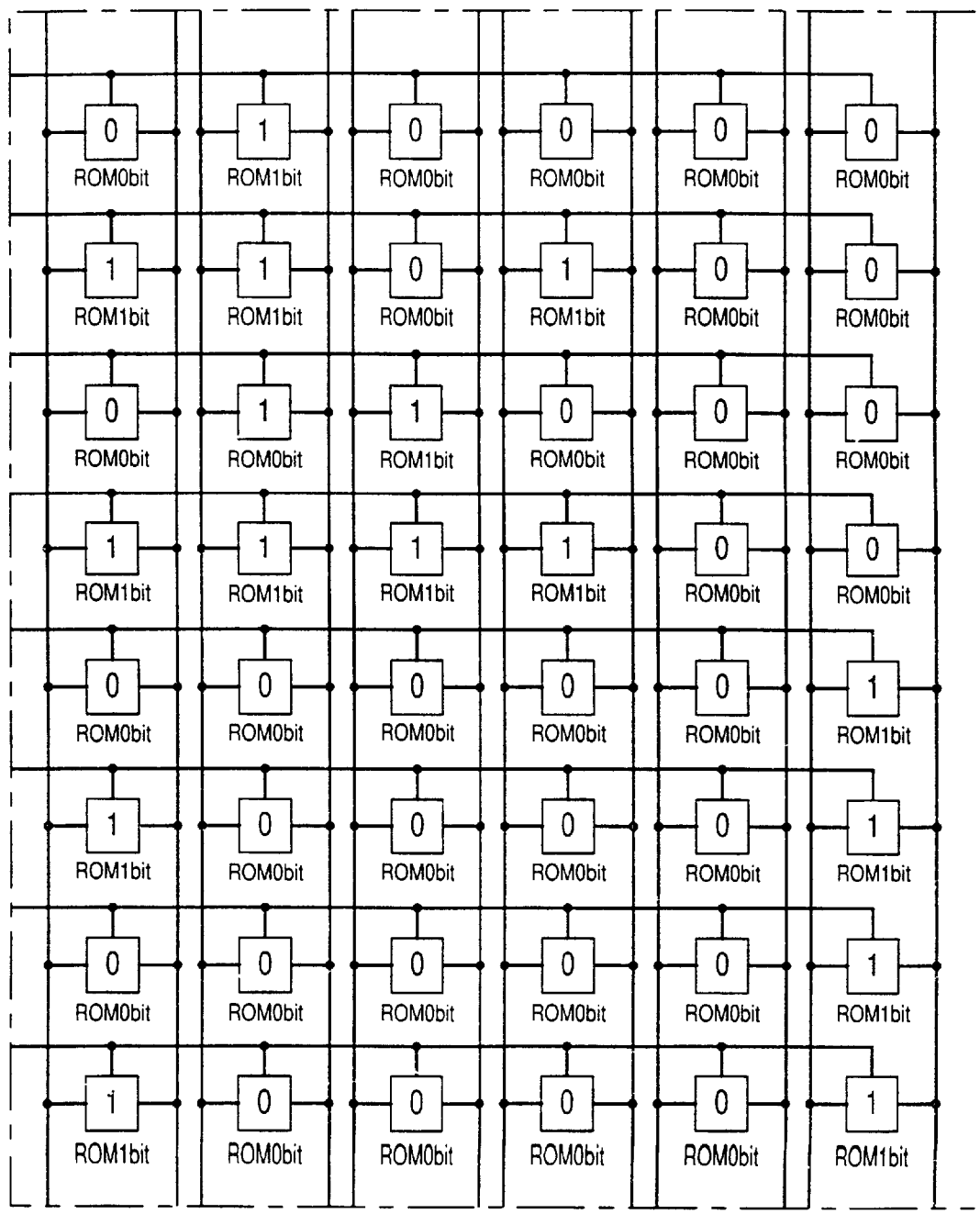
Fig.15 (Part VIII)

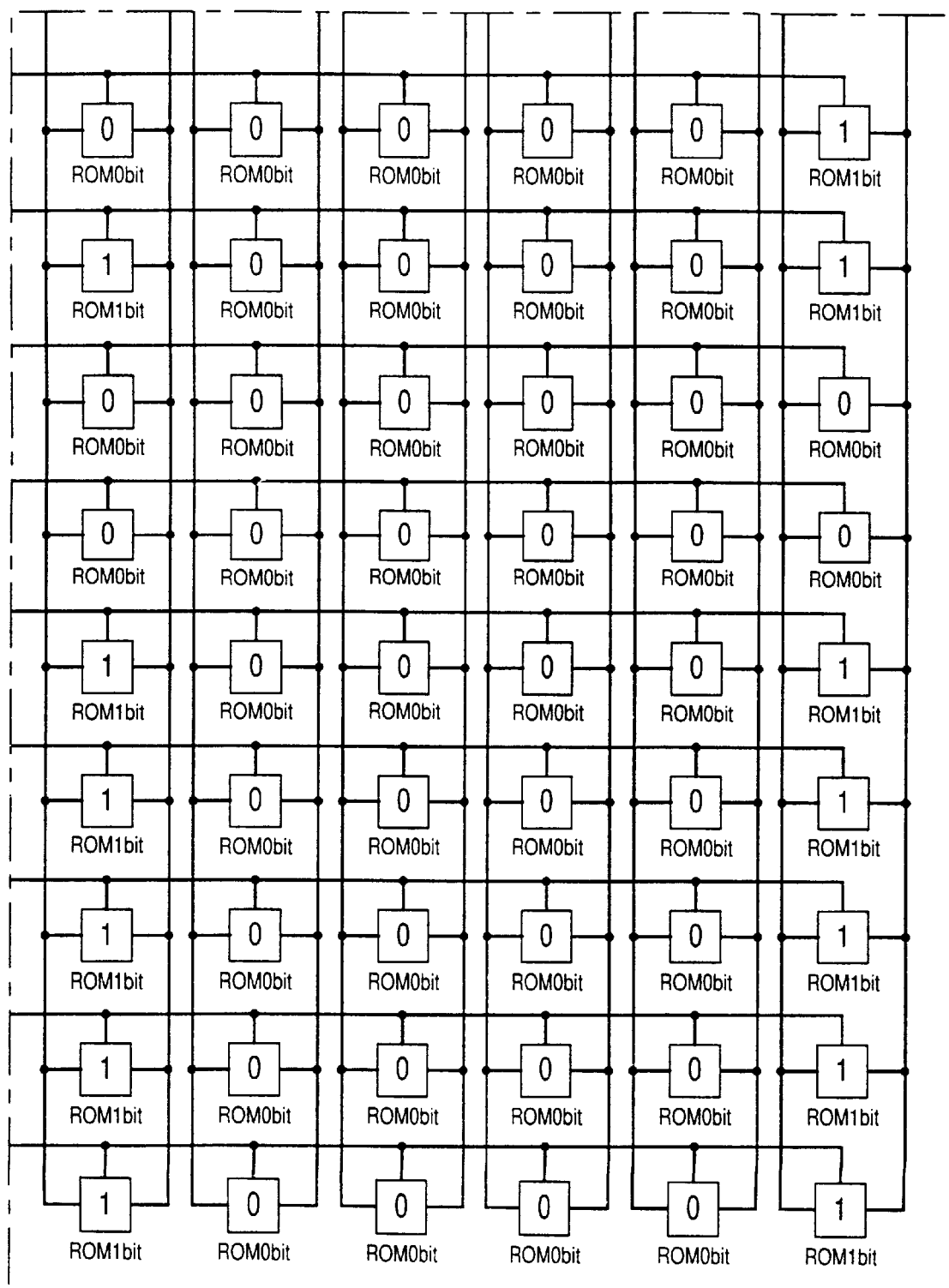
Fig.15 (Part IX)

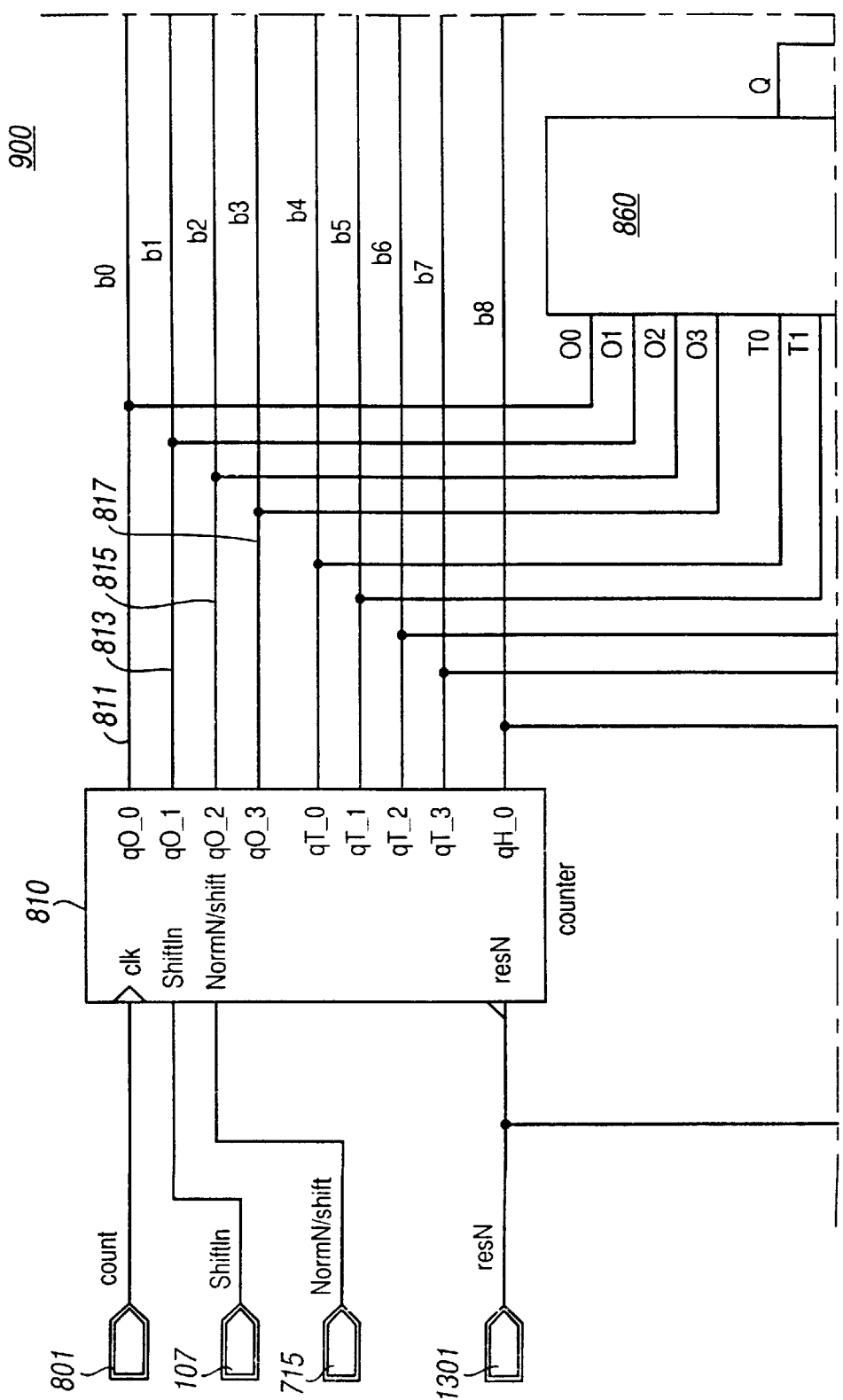
Fig. 18 (Part I)

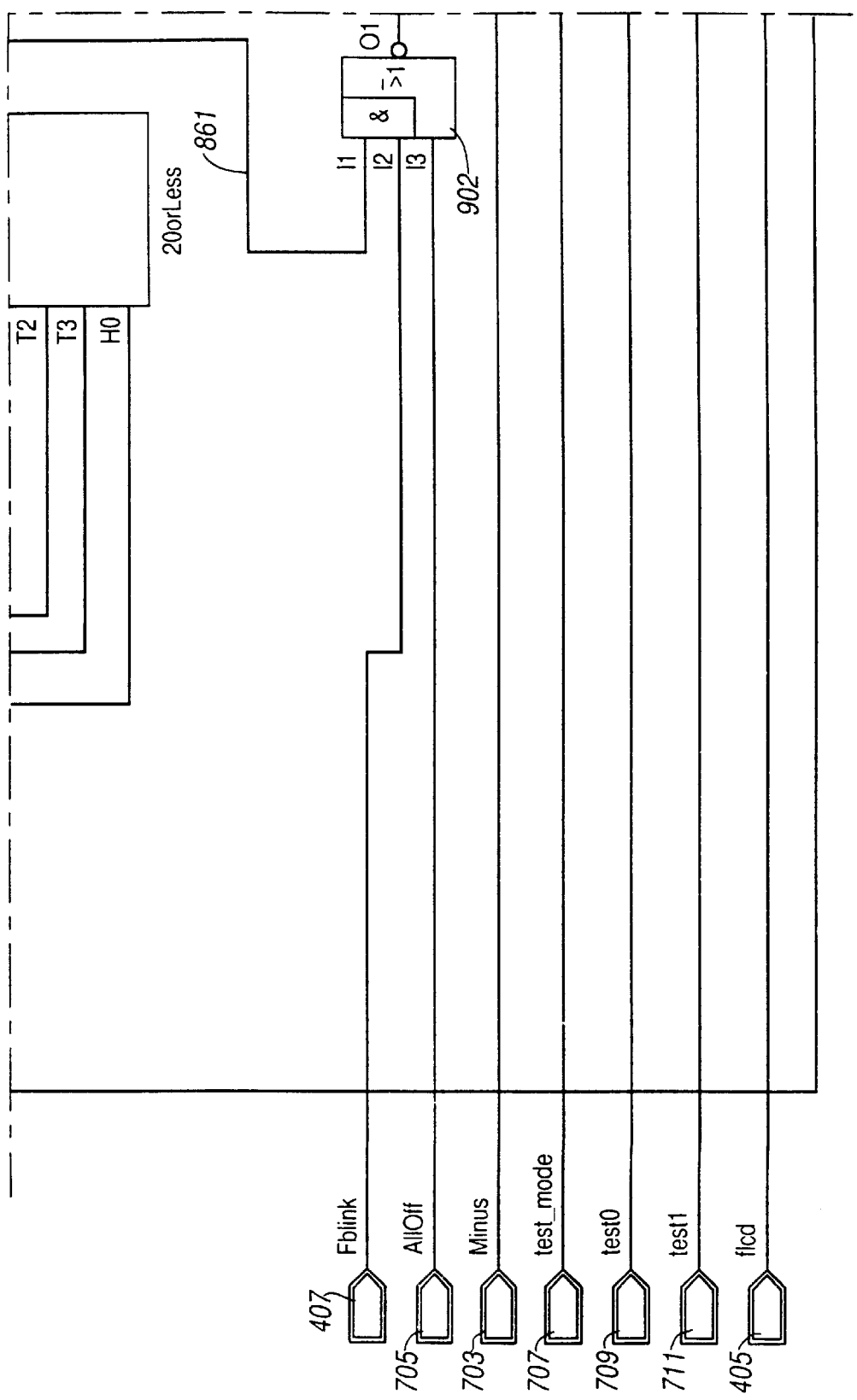
Fig.18 (Part II)

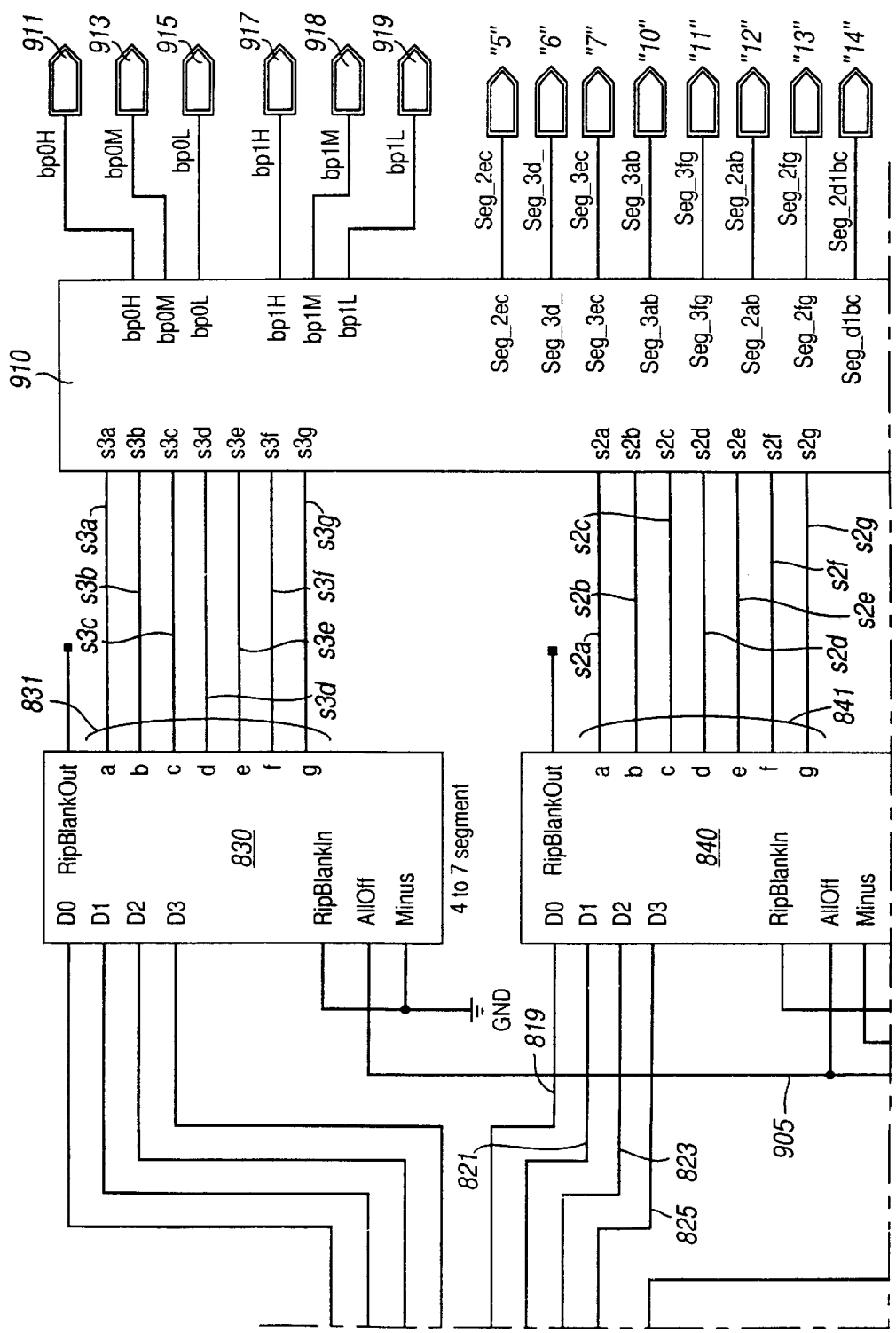
Fig. 18 (Part III)

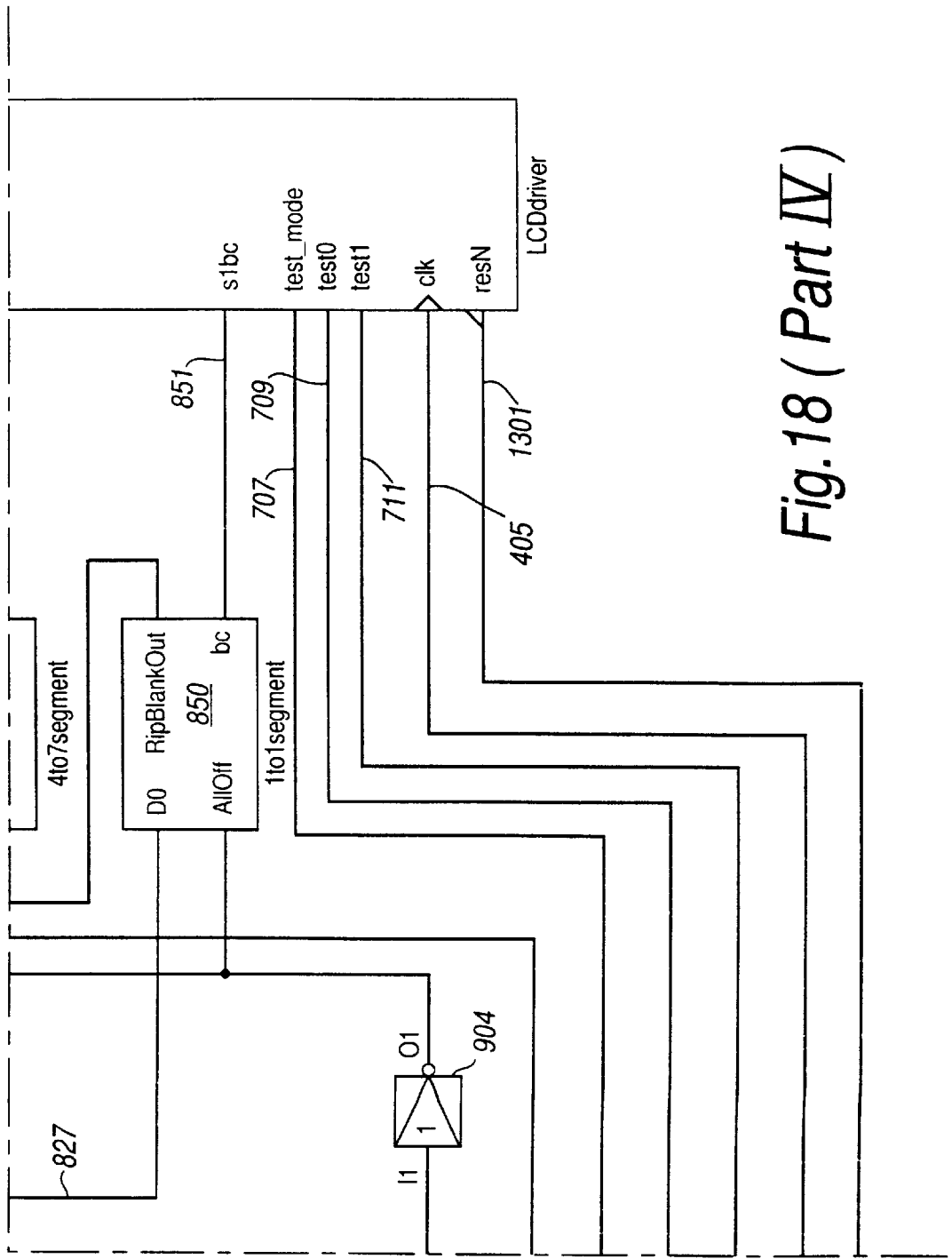
Fig.18 (Part IV)

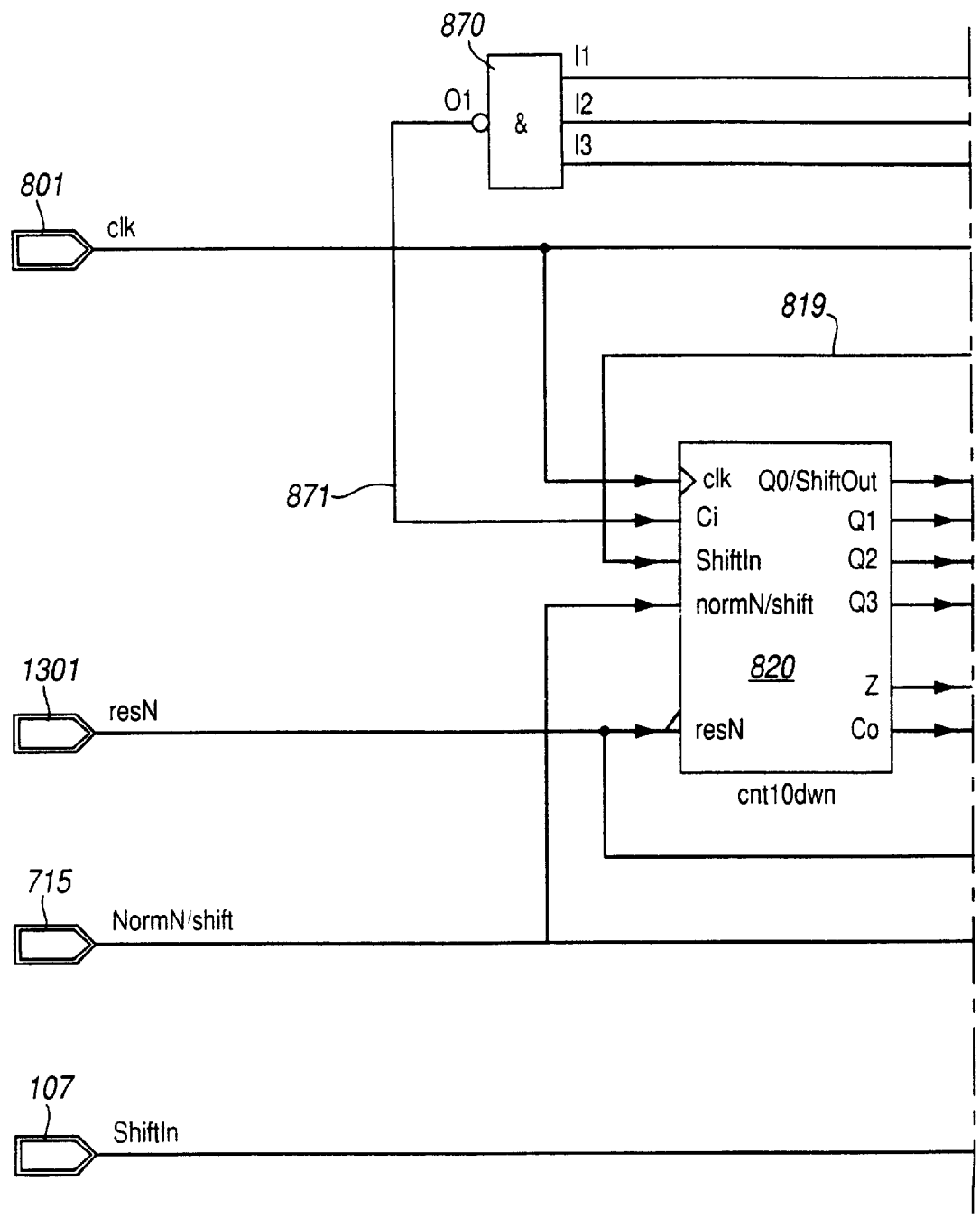
Fig.19 (Part I)

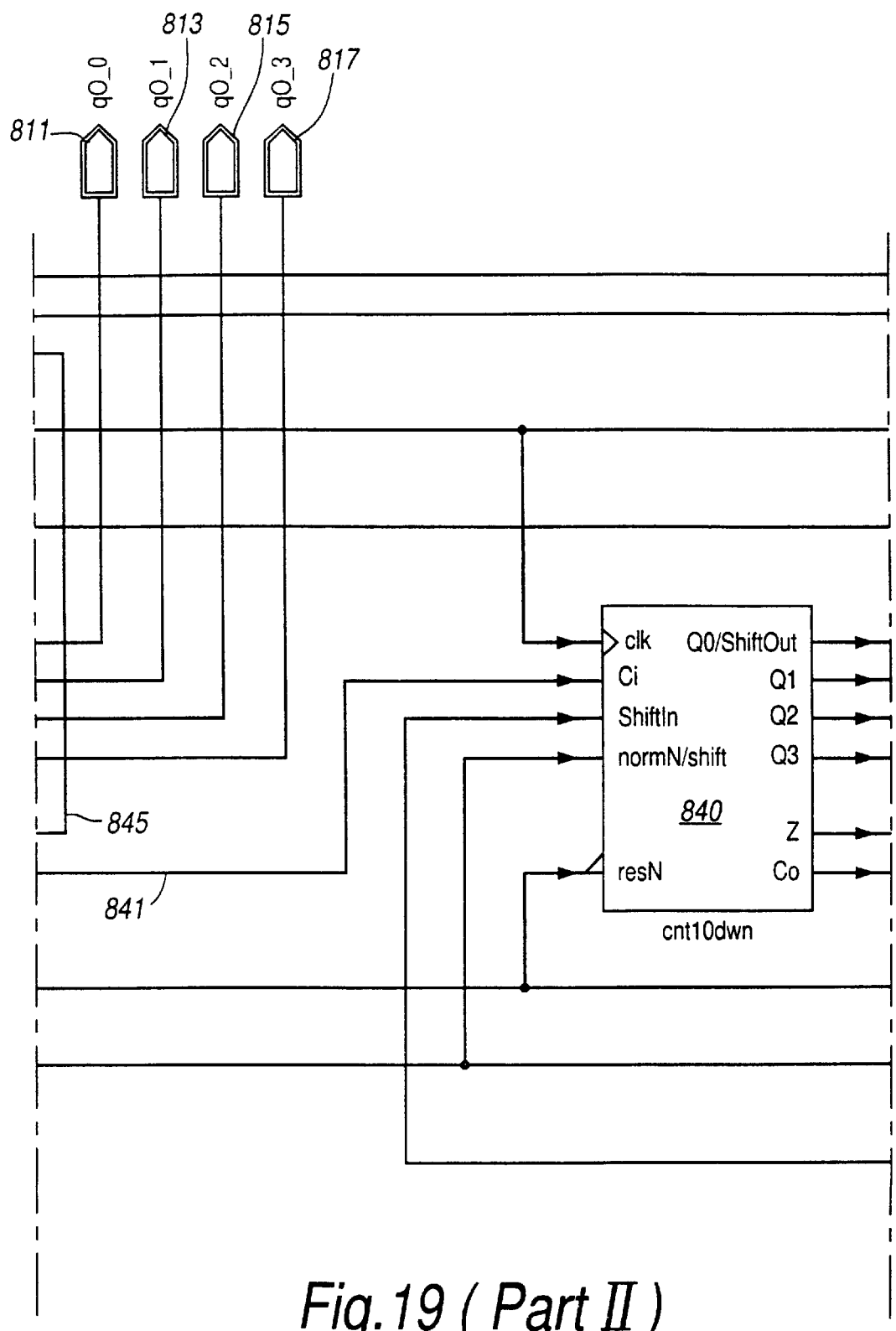
Fig. 19 (Part II)

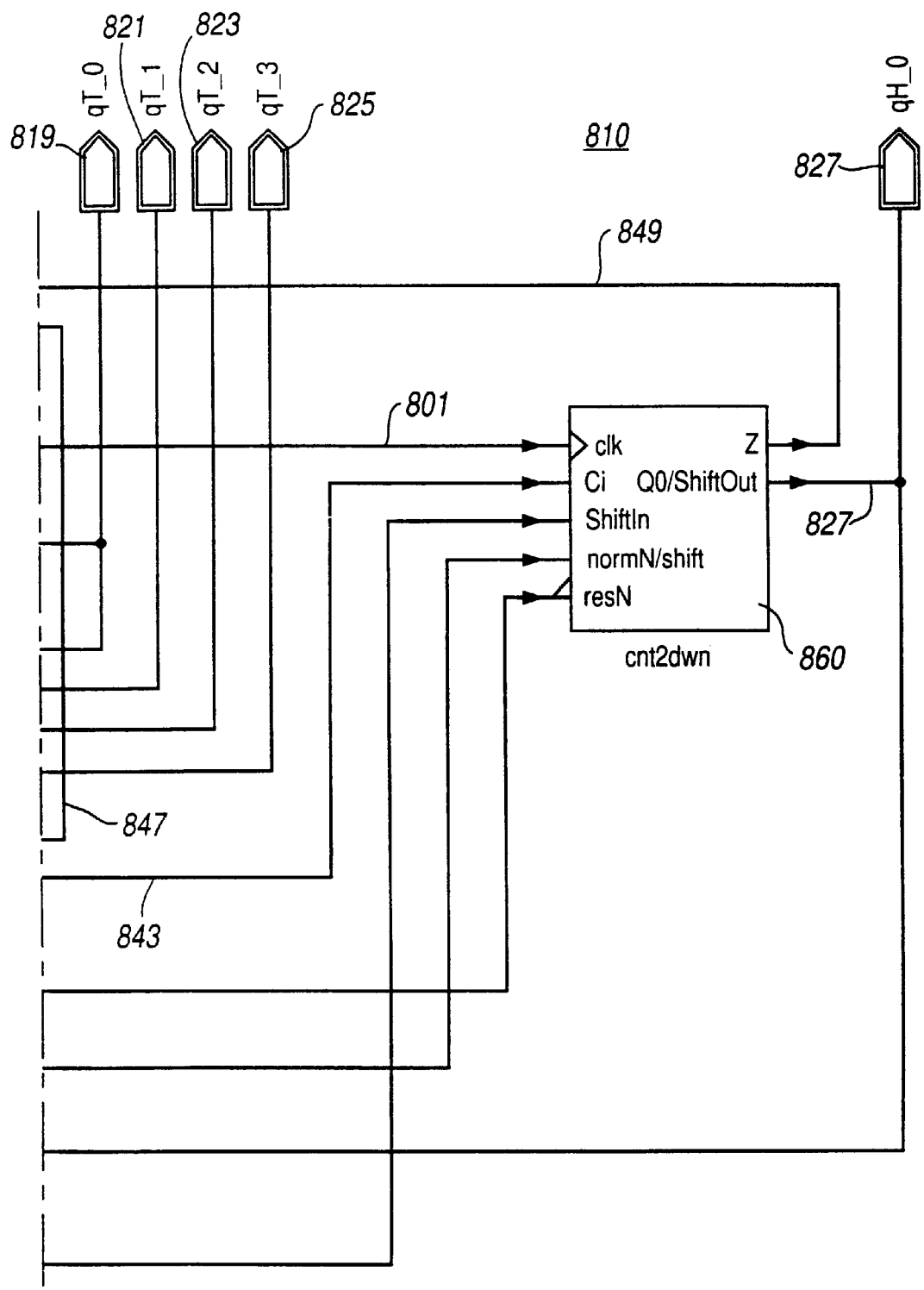
Fig.19 (Part III)

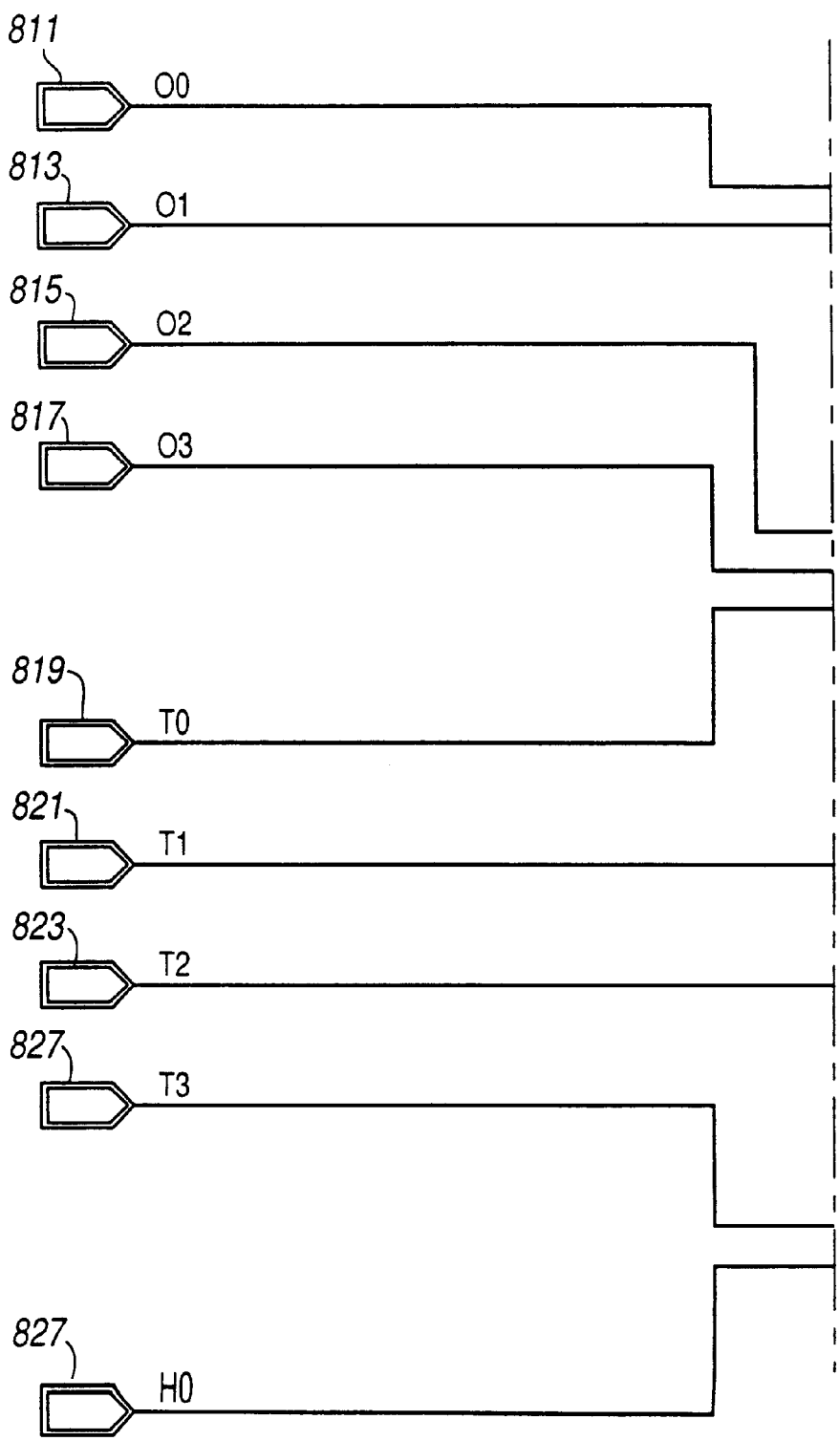
Fig.20 (Part I)

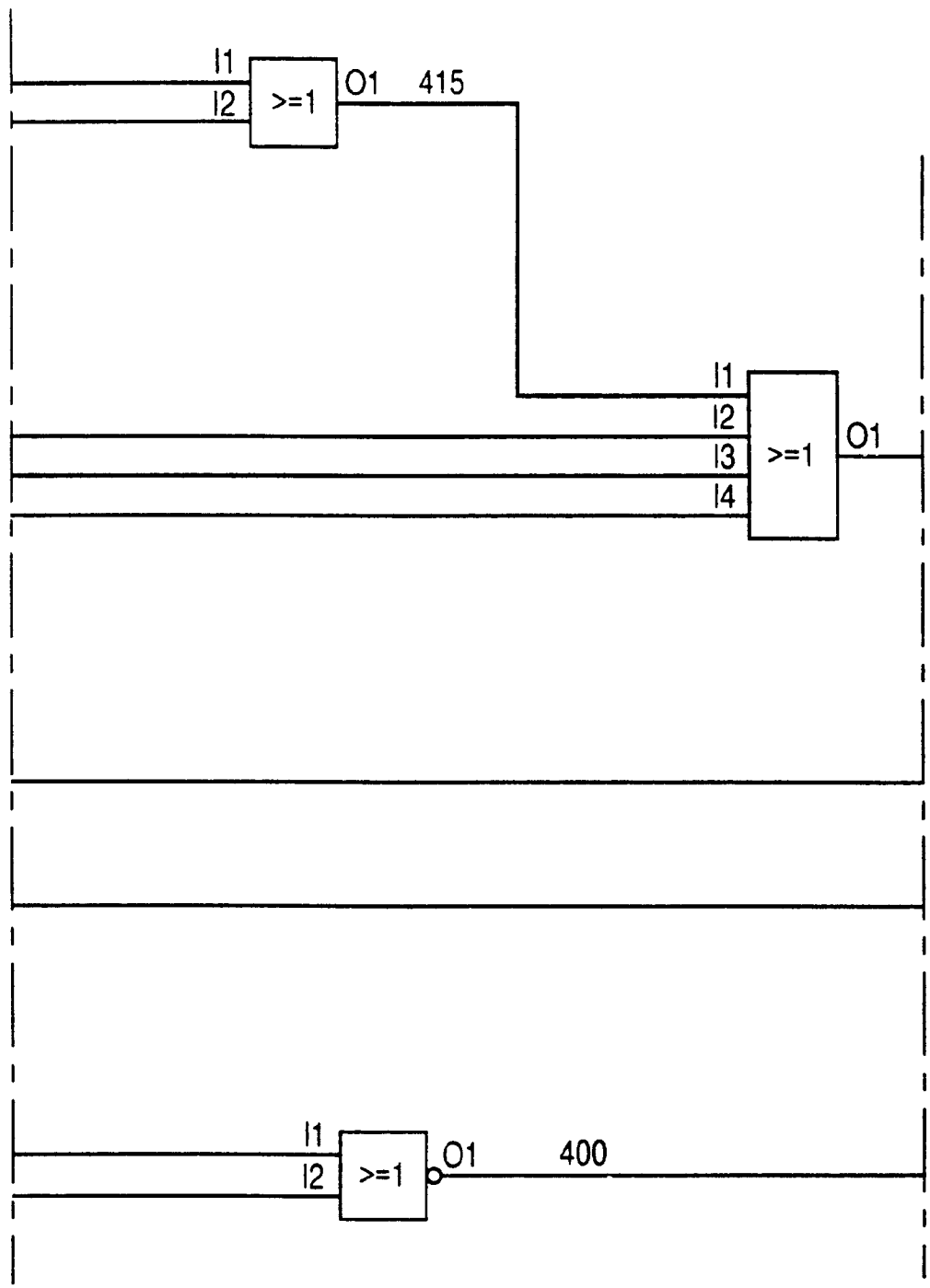
*Fig.20 ( Part II )*

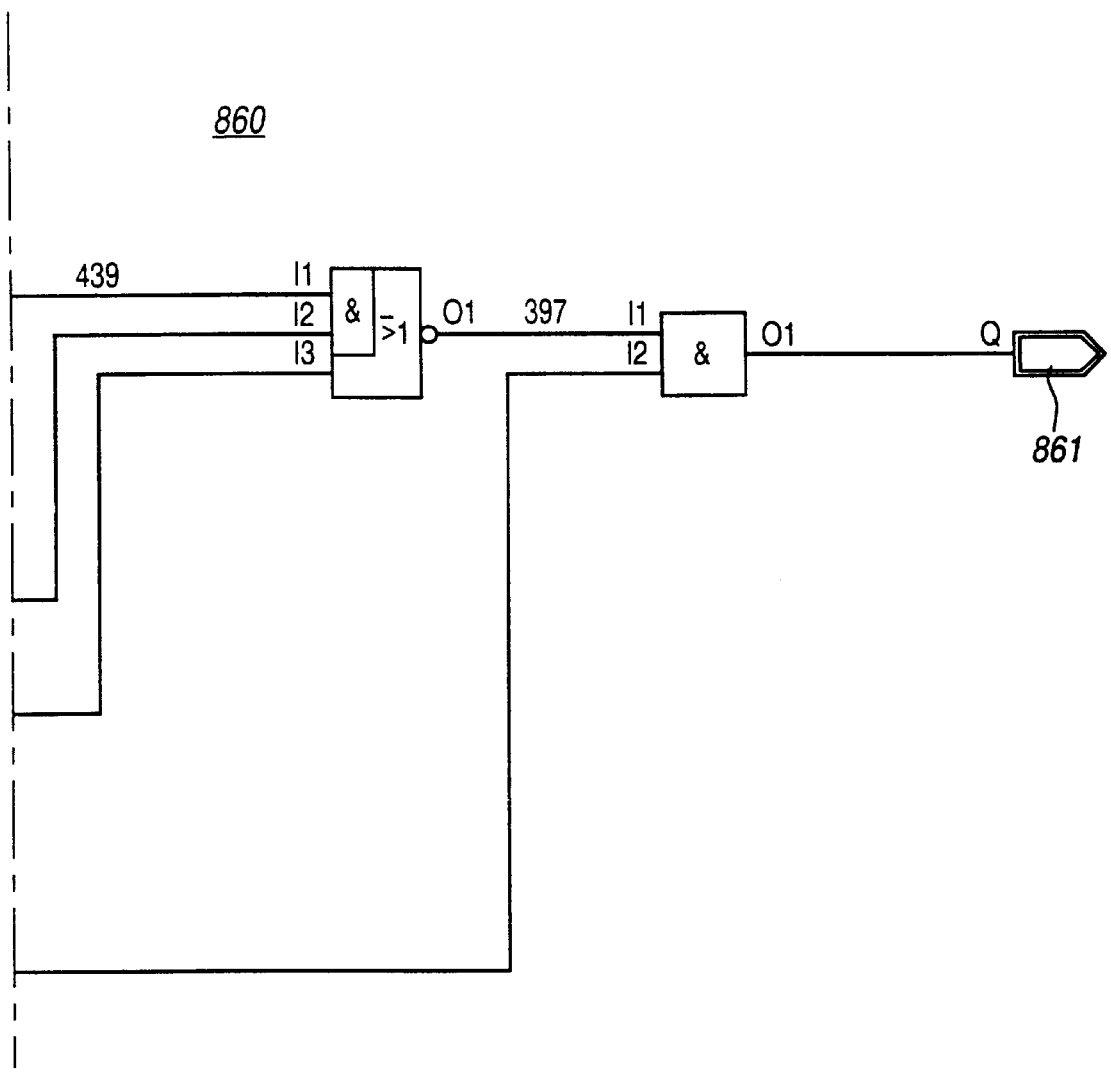
Fig.20 ( Part III )

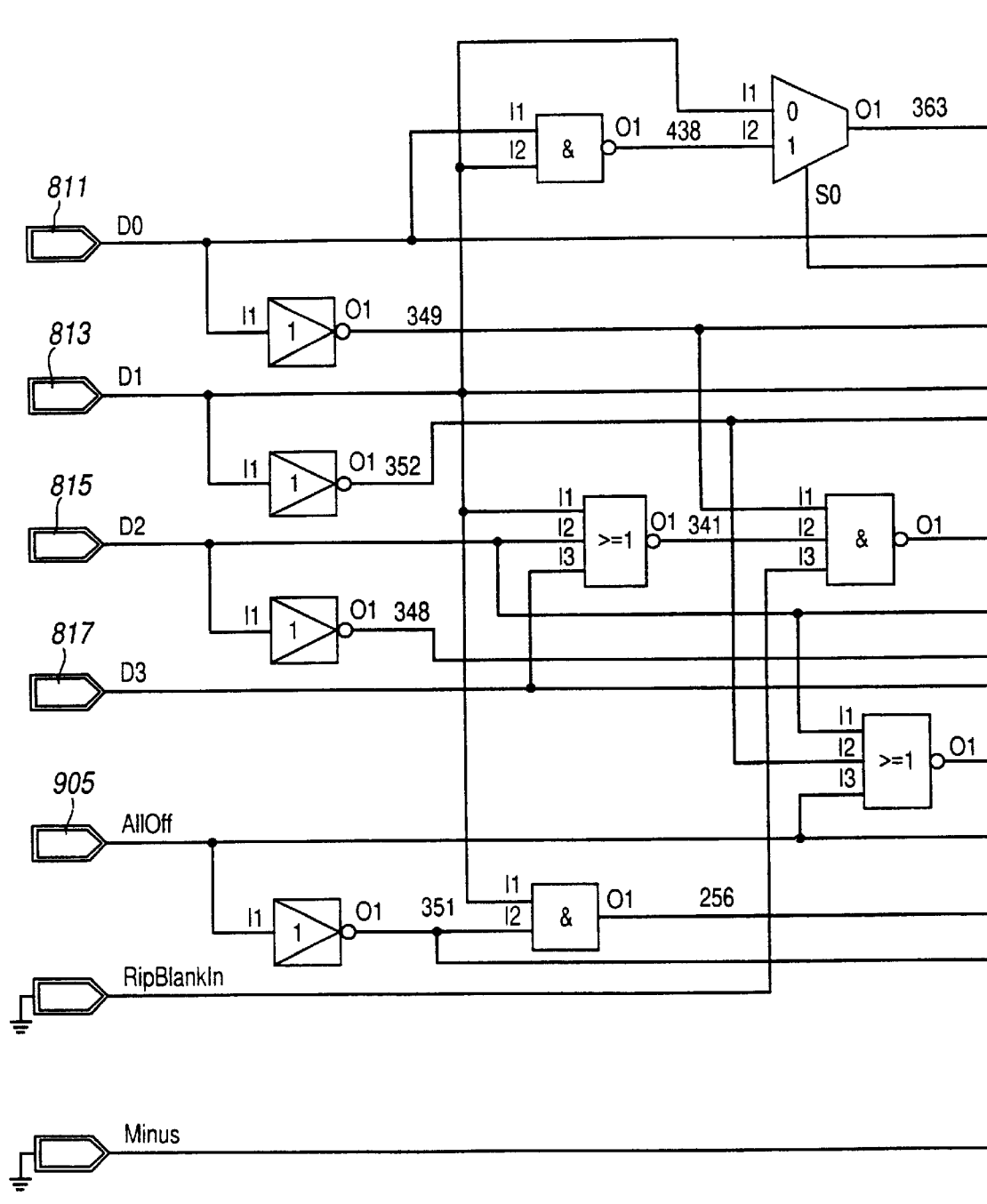
Fig.21 (Part I)

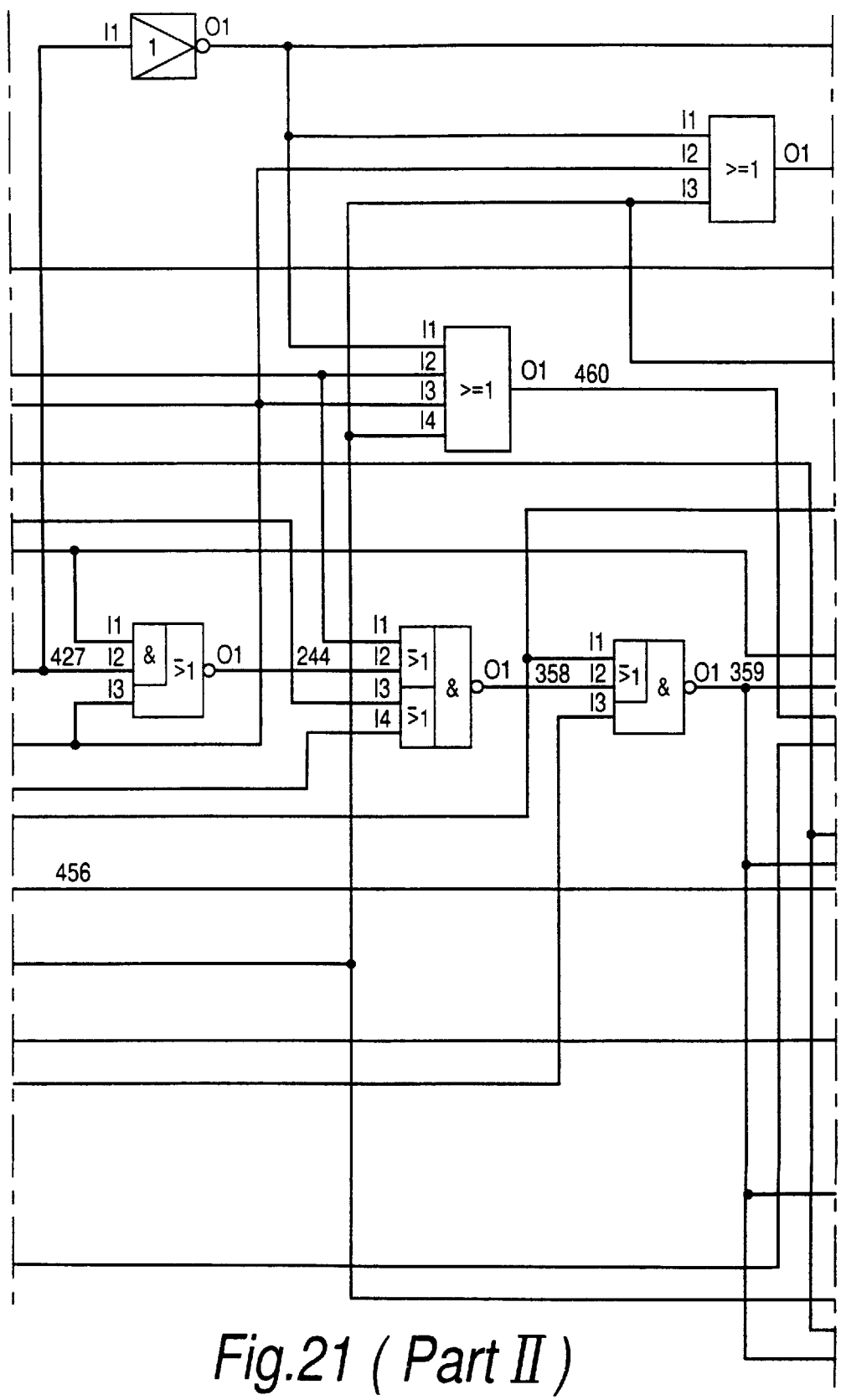
Fig.21 (Part II)

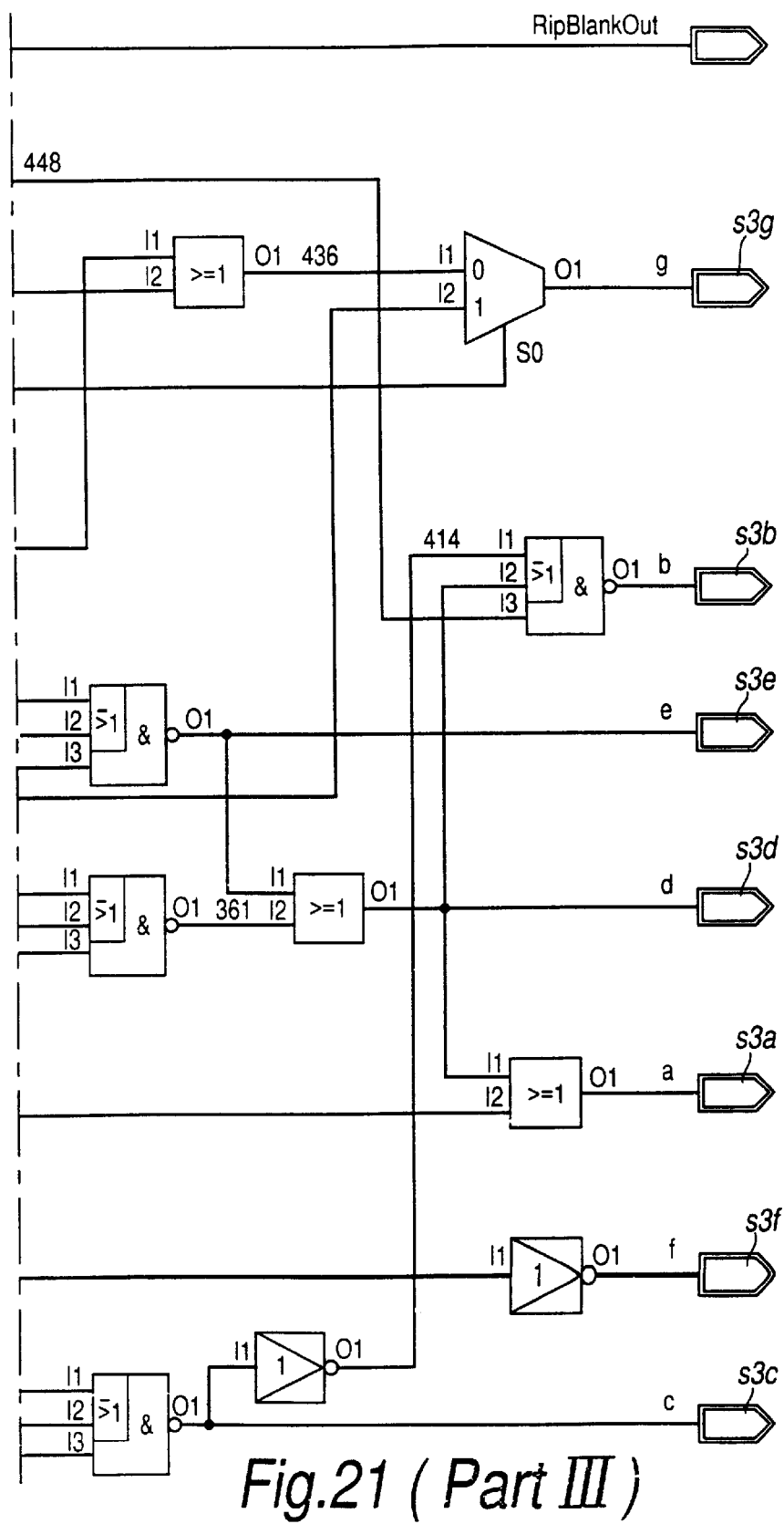
Fig.21 ( Part III )

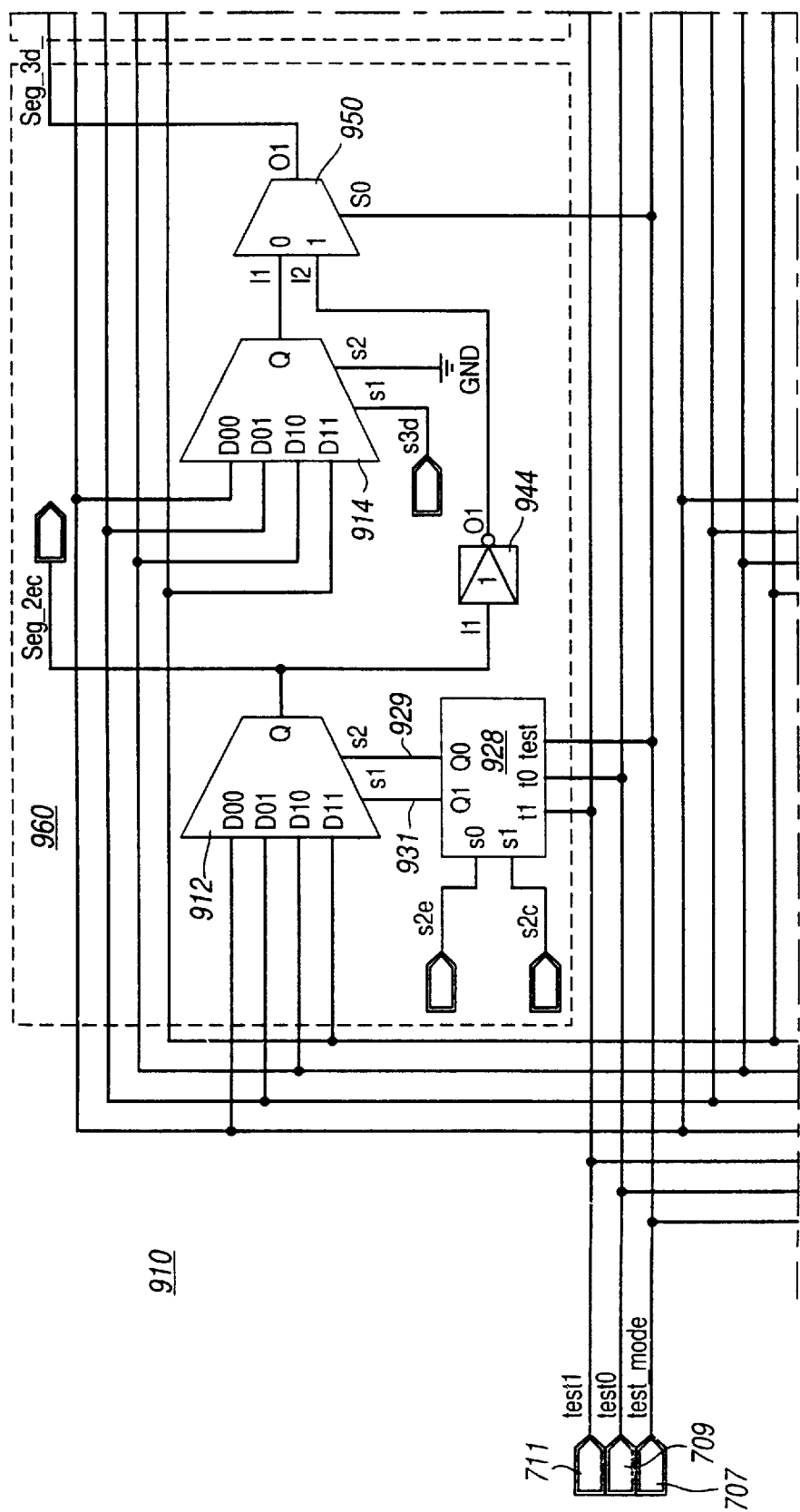
Fig. 23 (Part I)

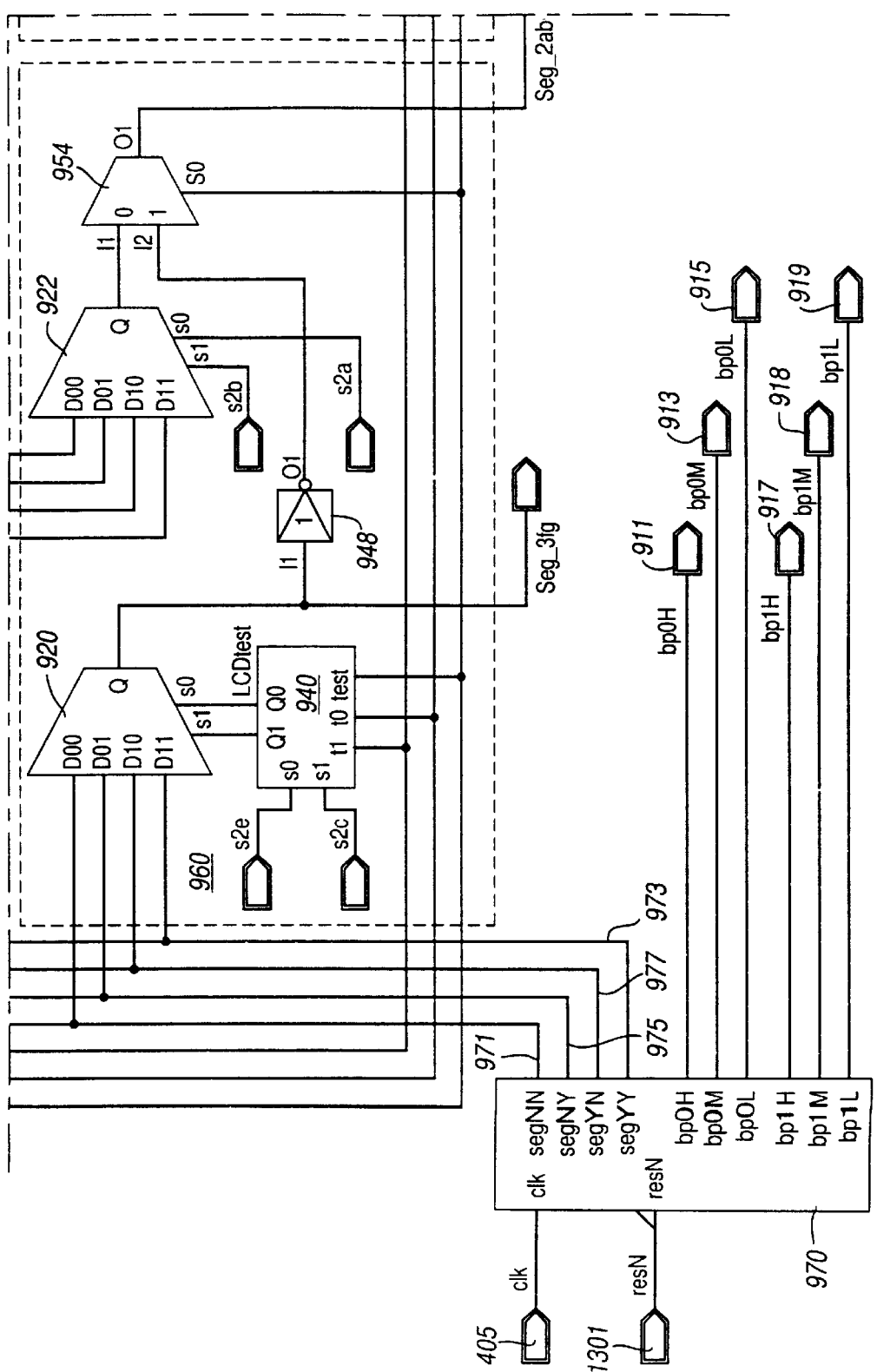
Fig.23 (Part II)

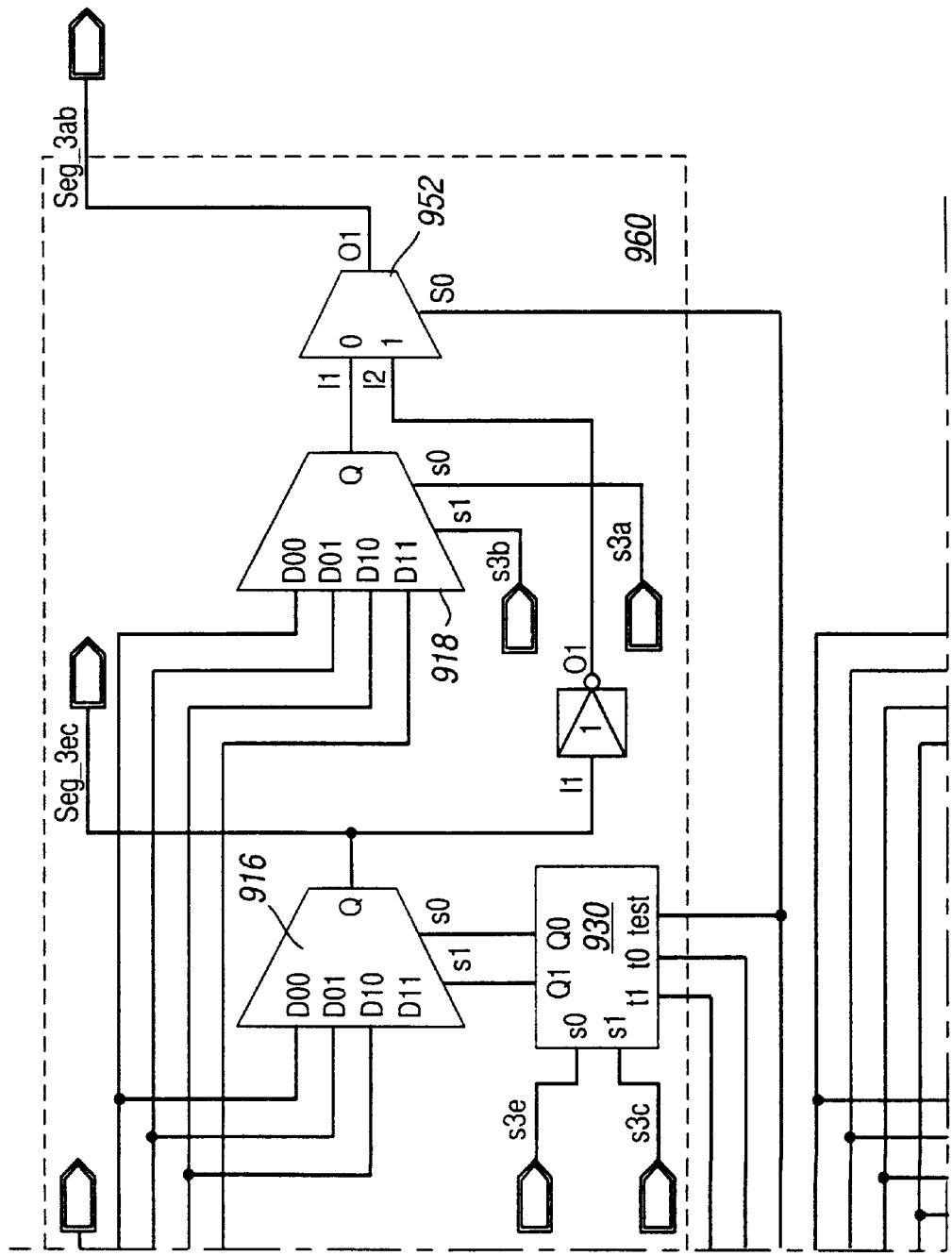
Fig. 23 (Part III)

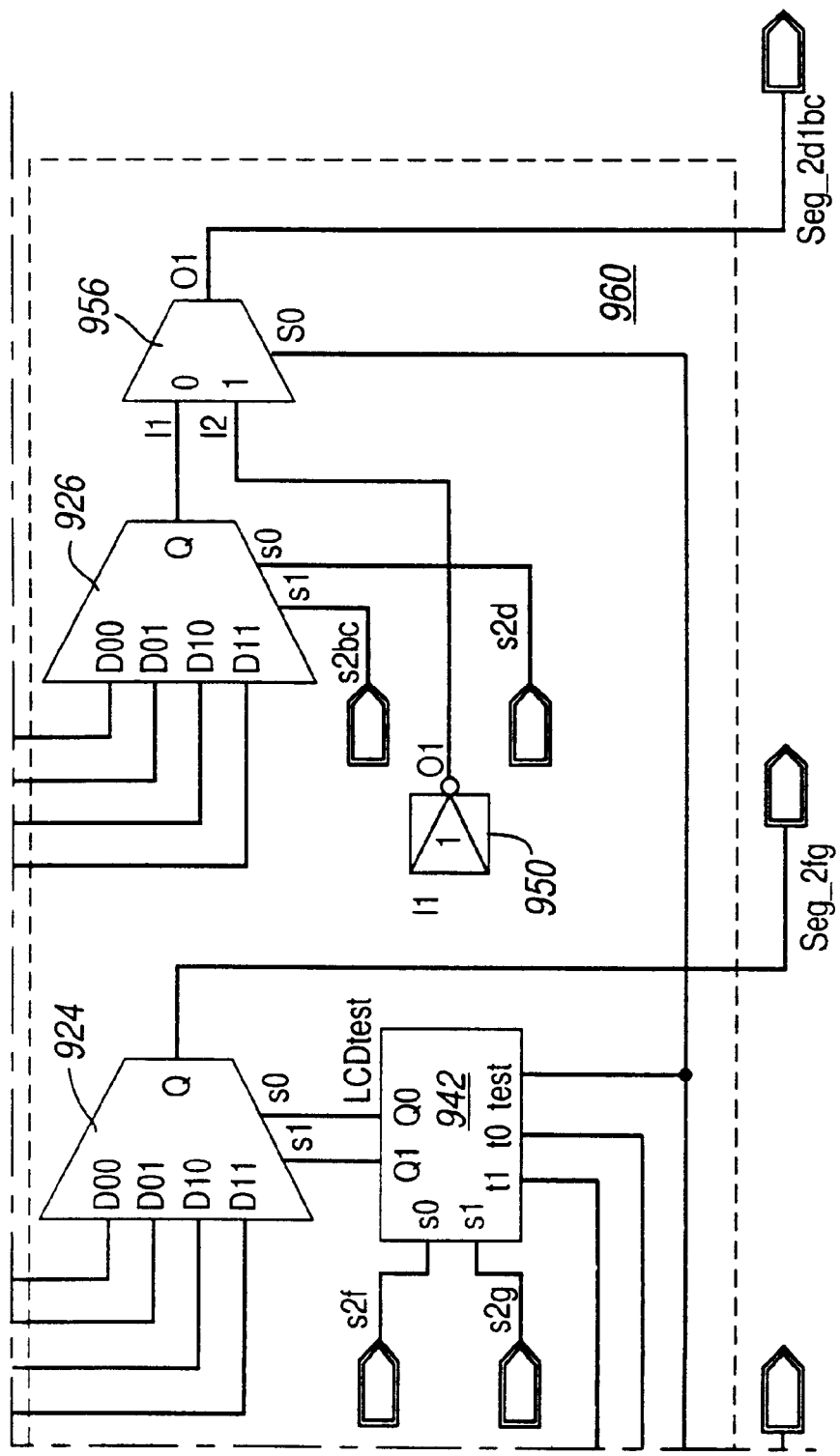
Fig.23 (Part IV)

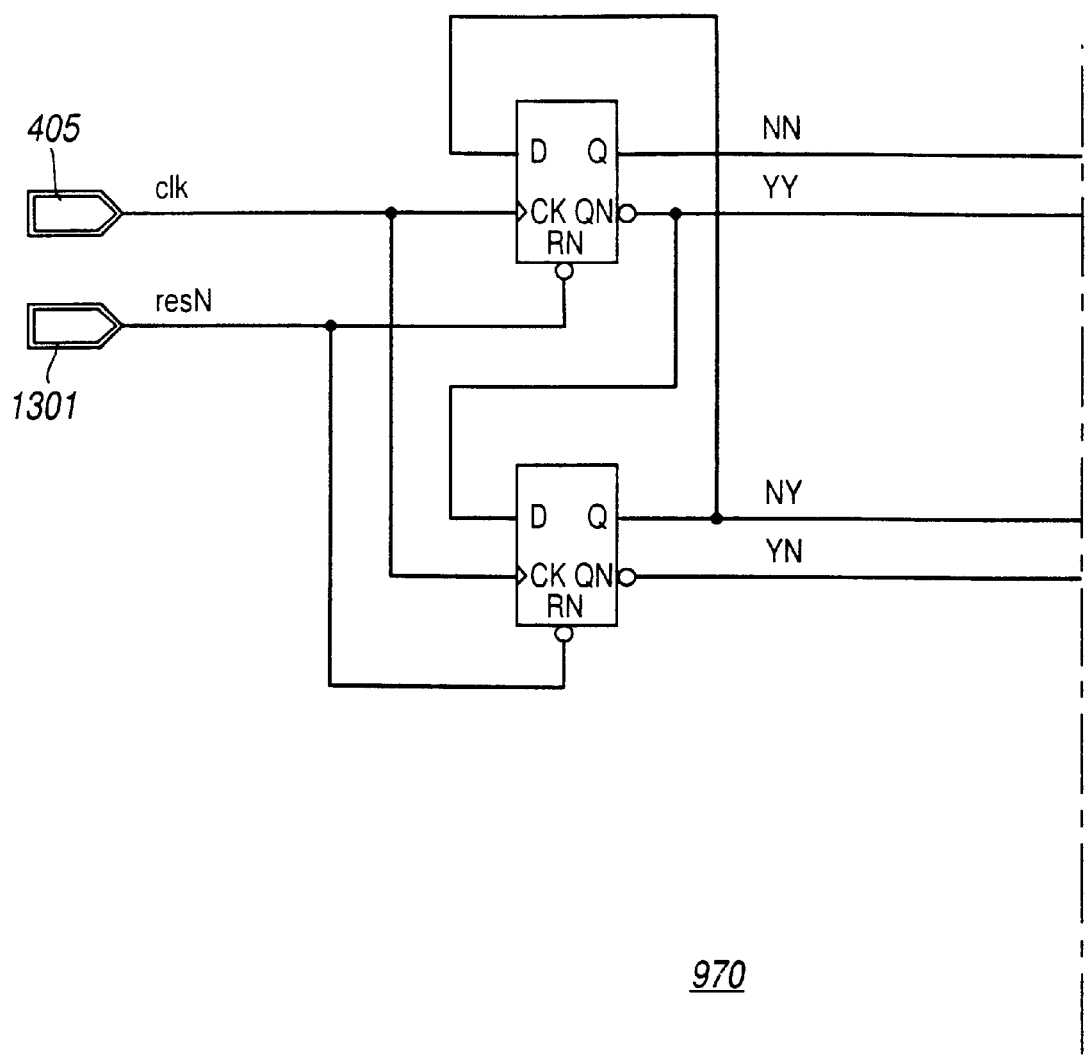
Fig.26 (Part I)

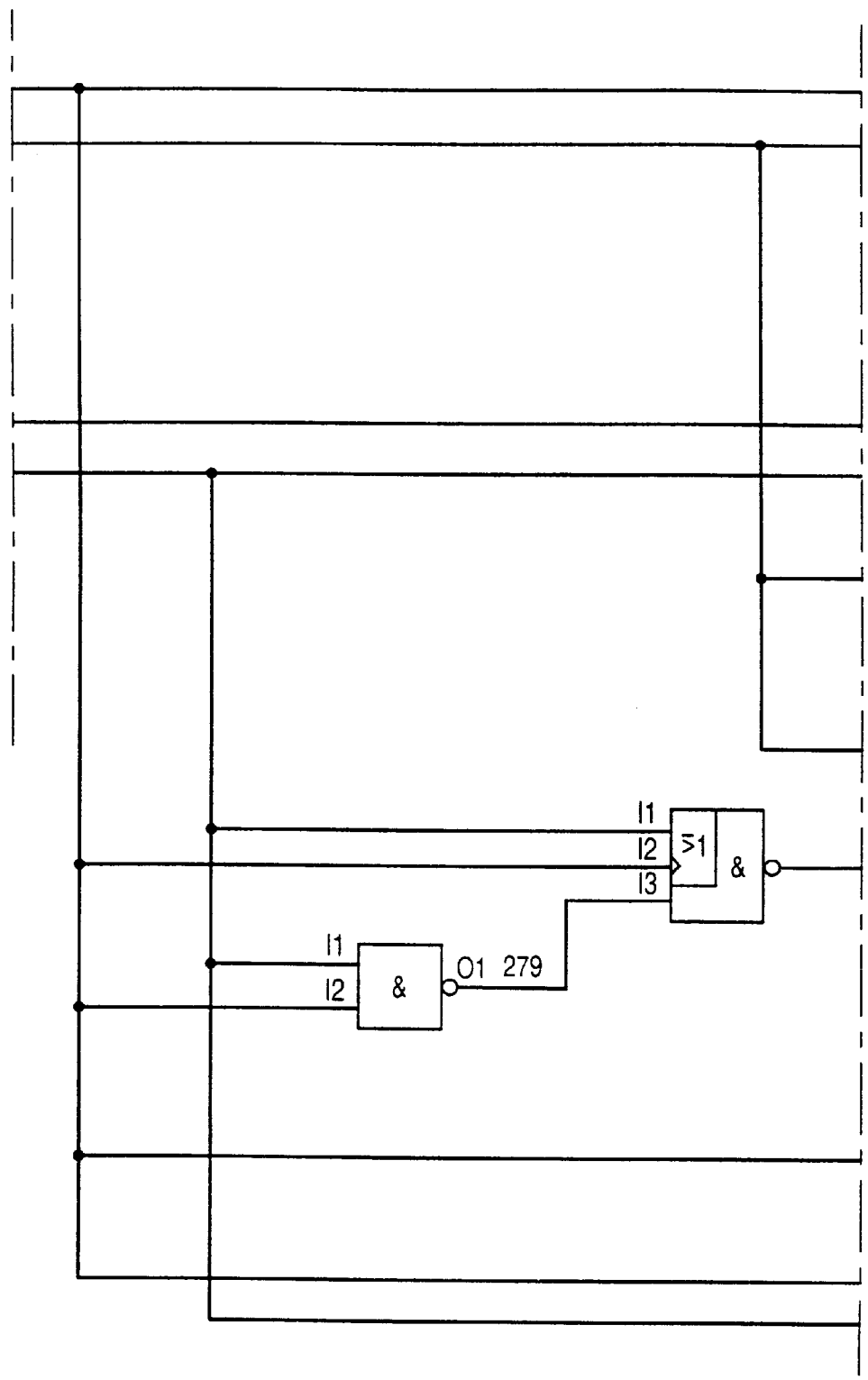
Fig.26 ( Part II )

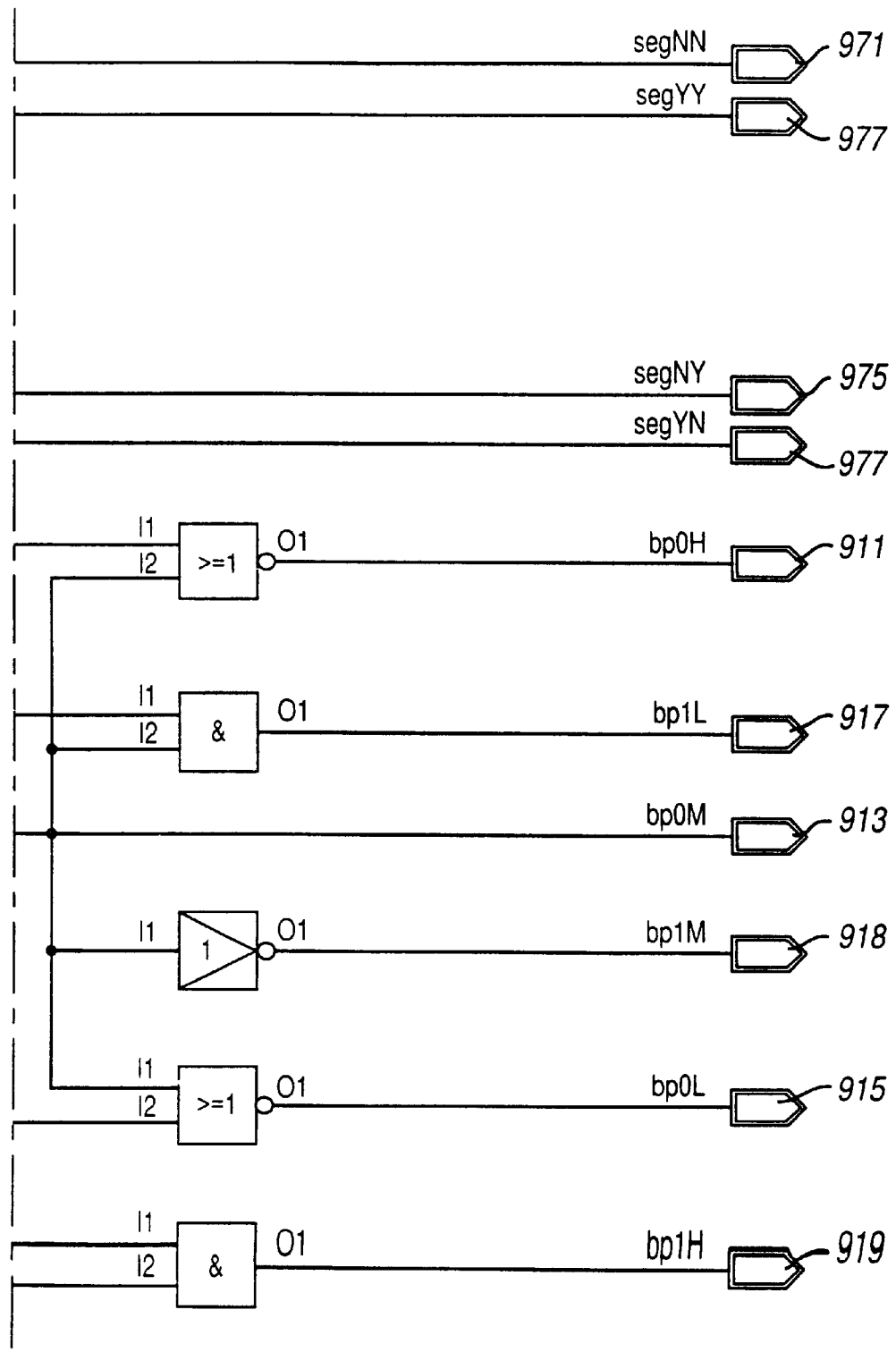
Fig.26 ( Part III )

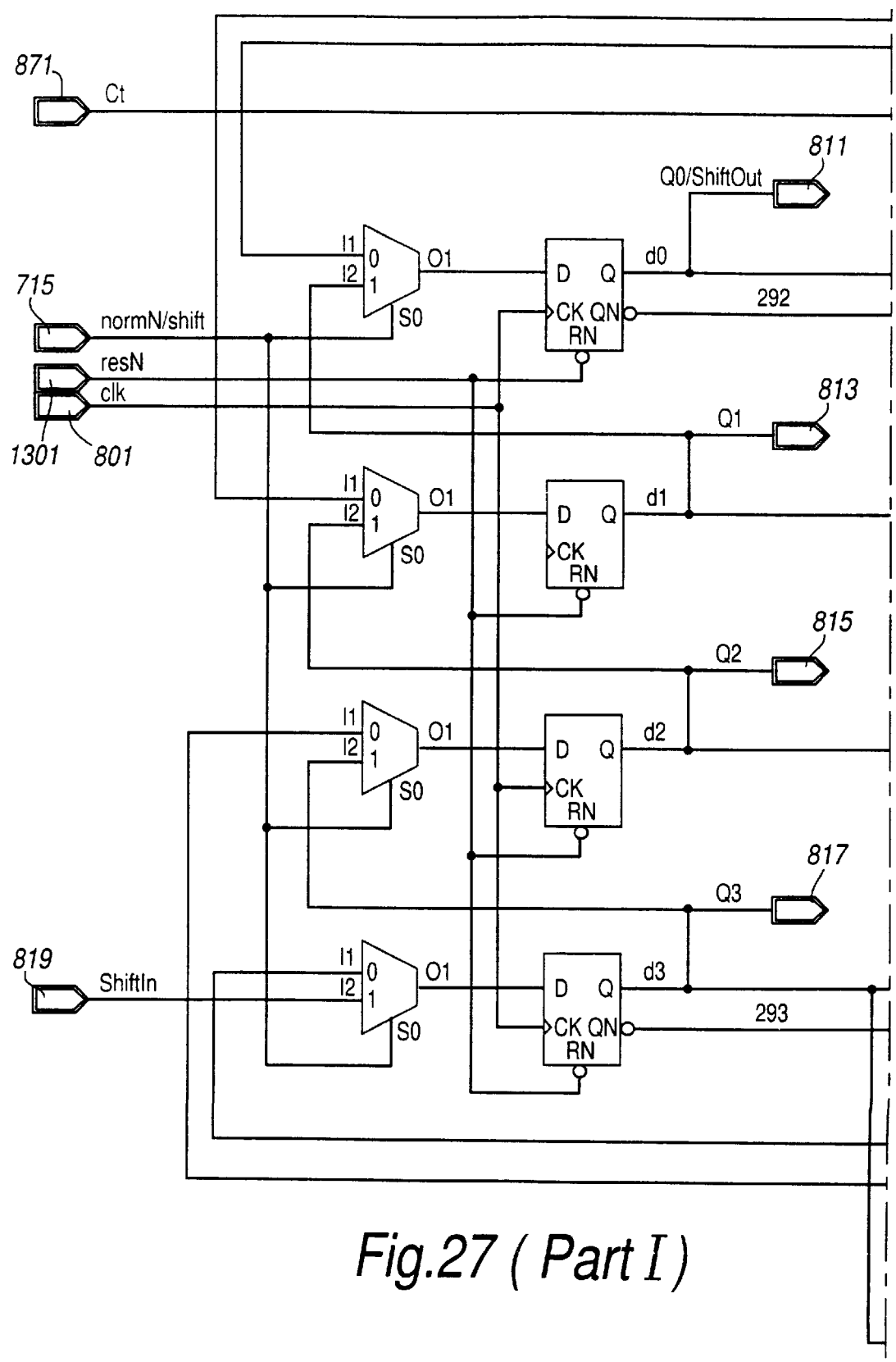
Fig.27 (Part I)

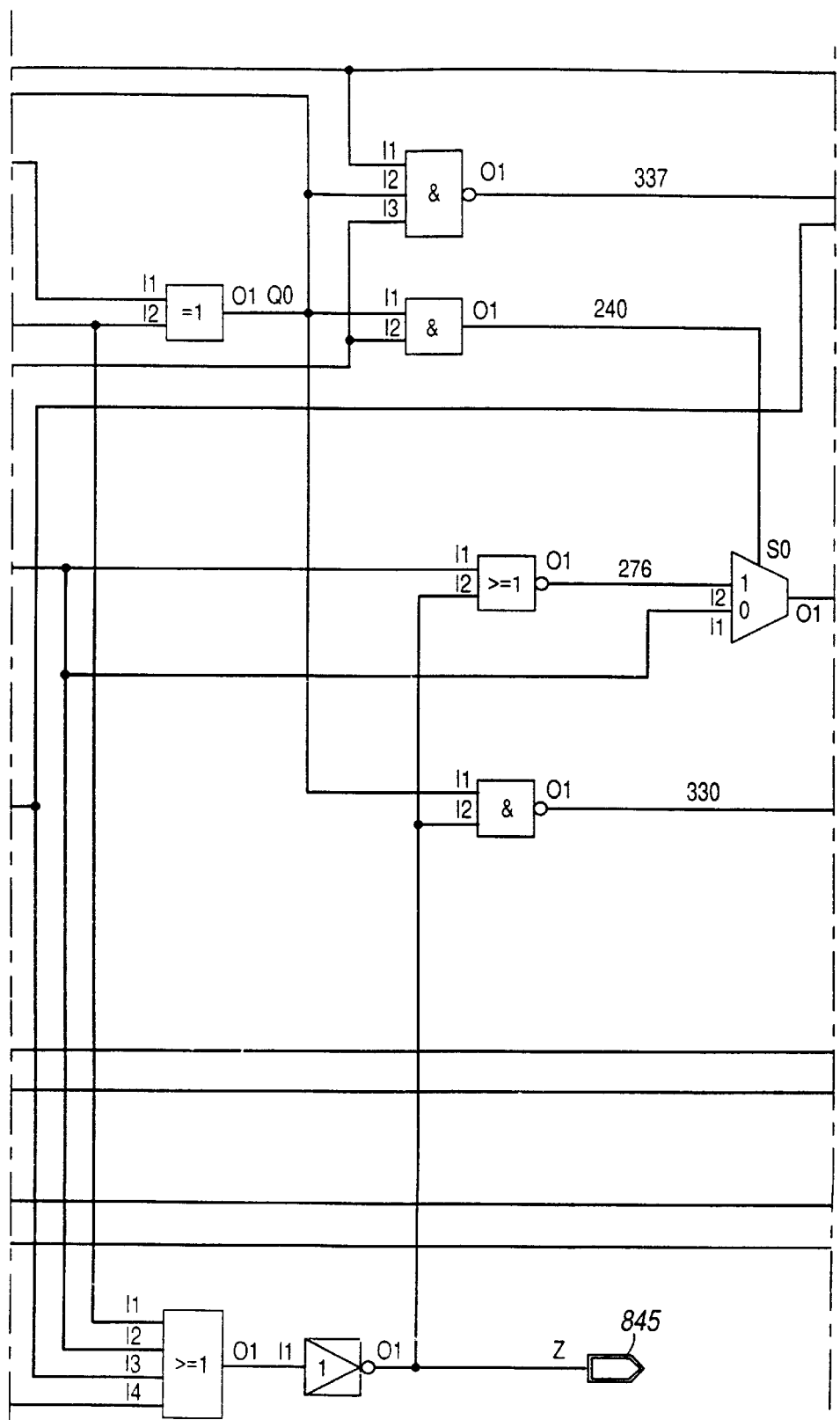
Fig.27 ( Part II )

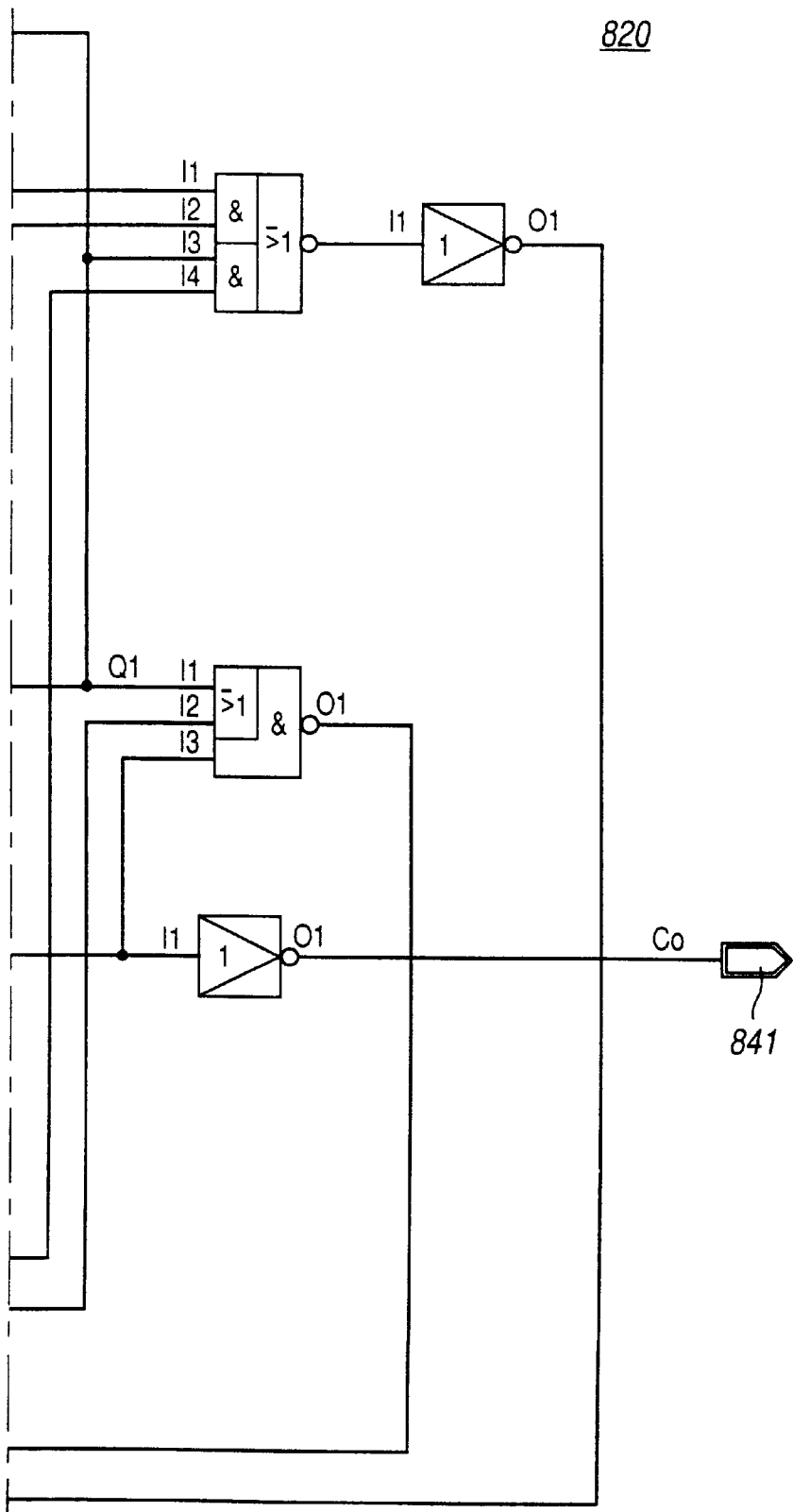
Fig.27 (Part III)

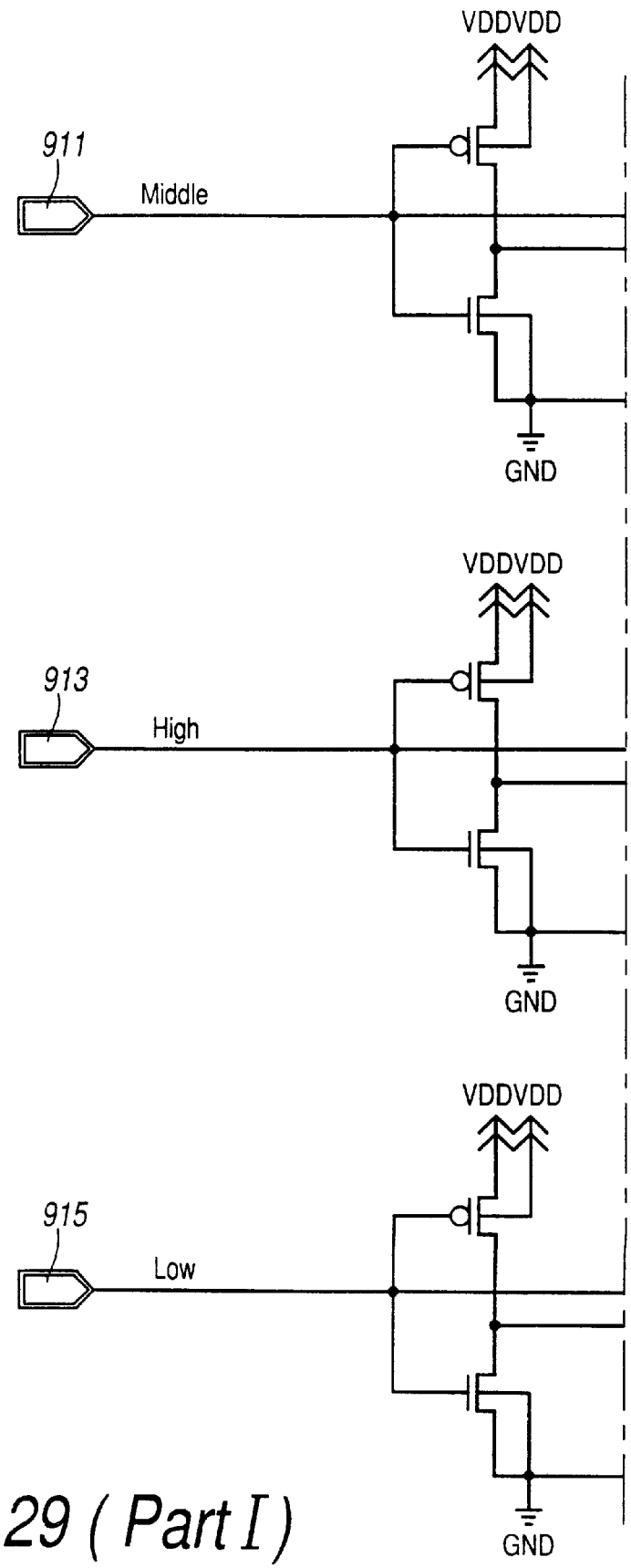
Fig.29 (Part I)

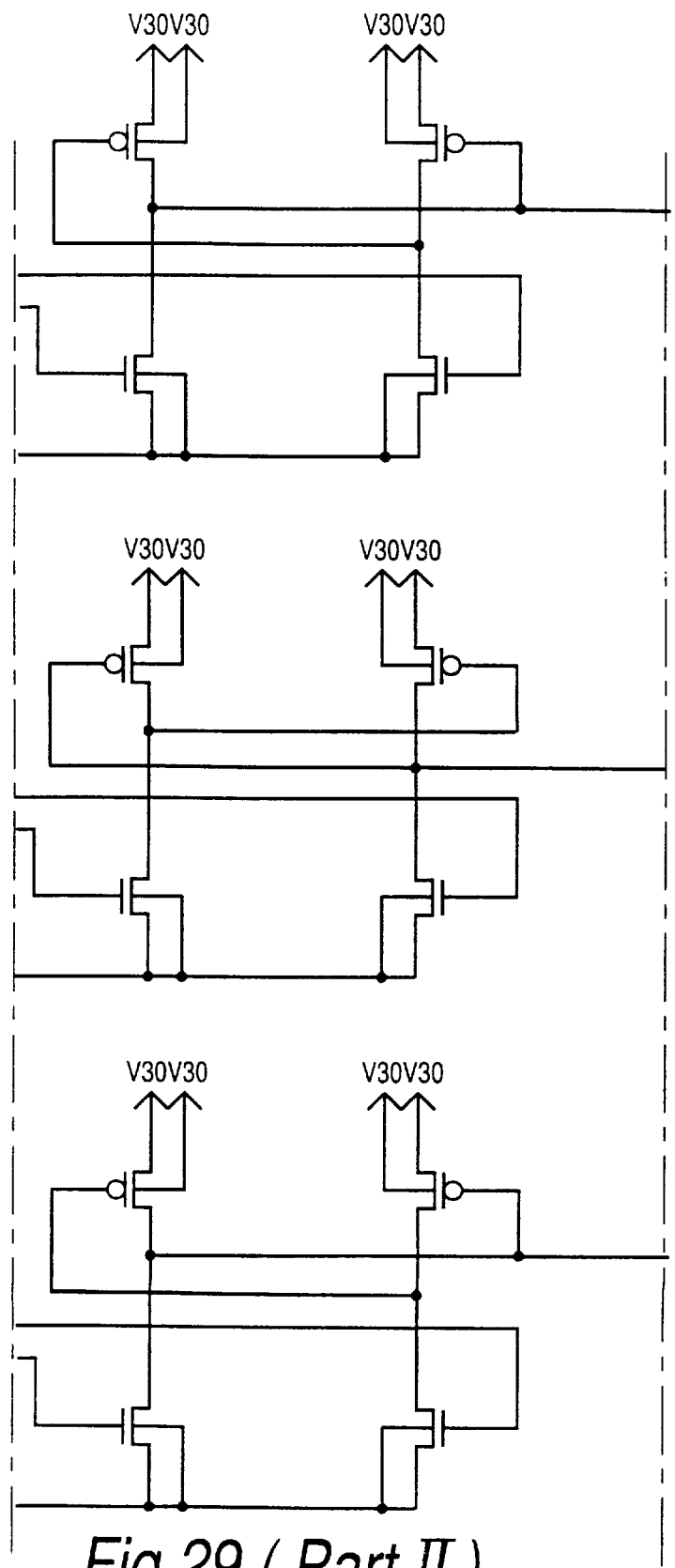
Fig.29 (Part II)

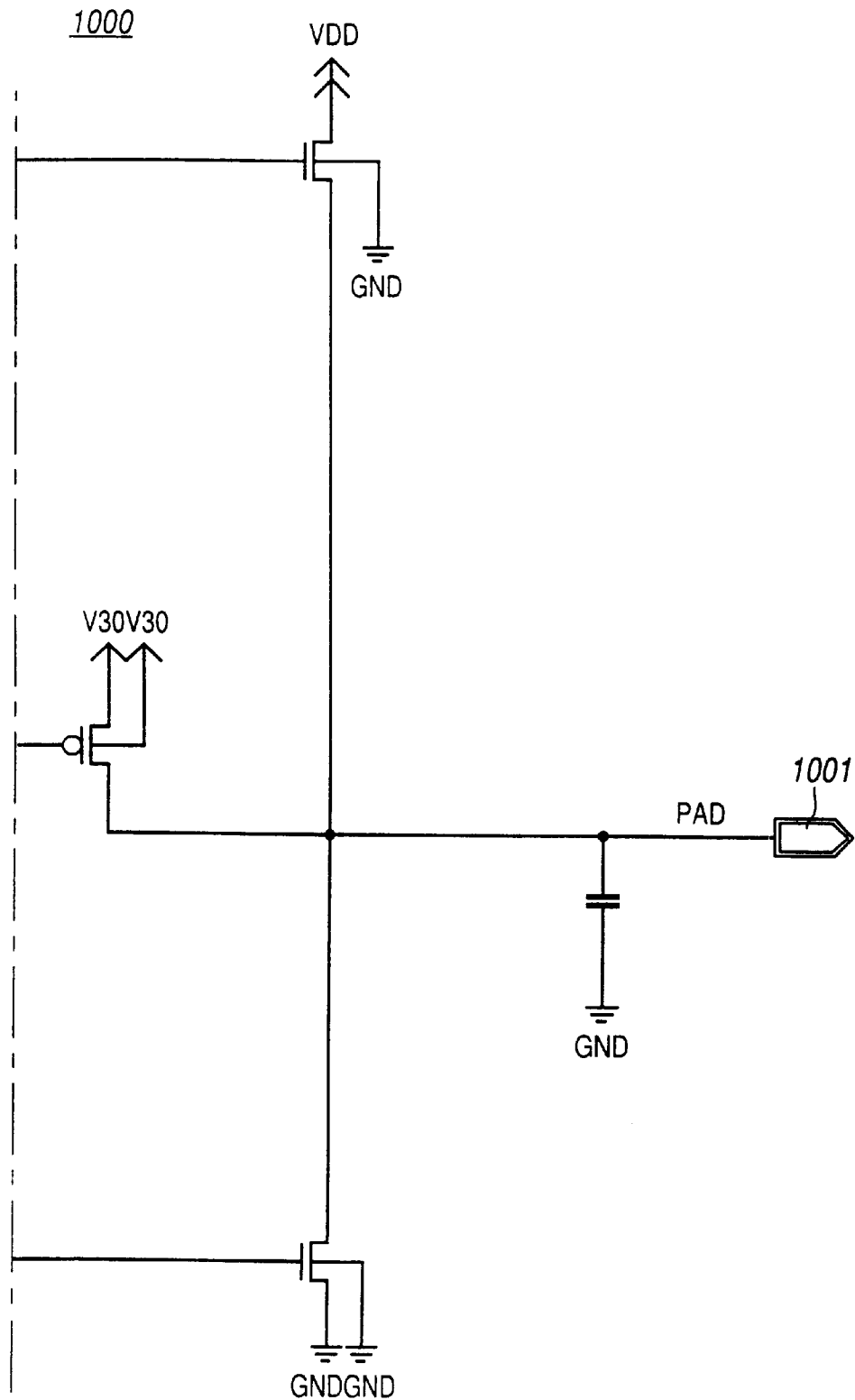
Fig.29 (Part III)

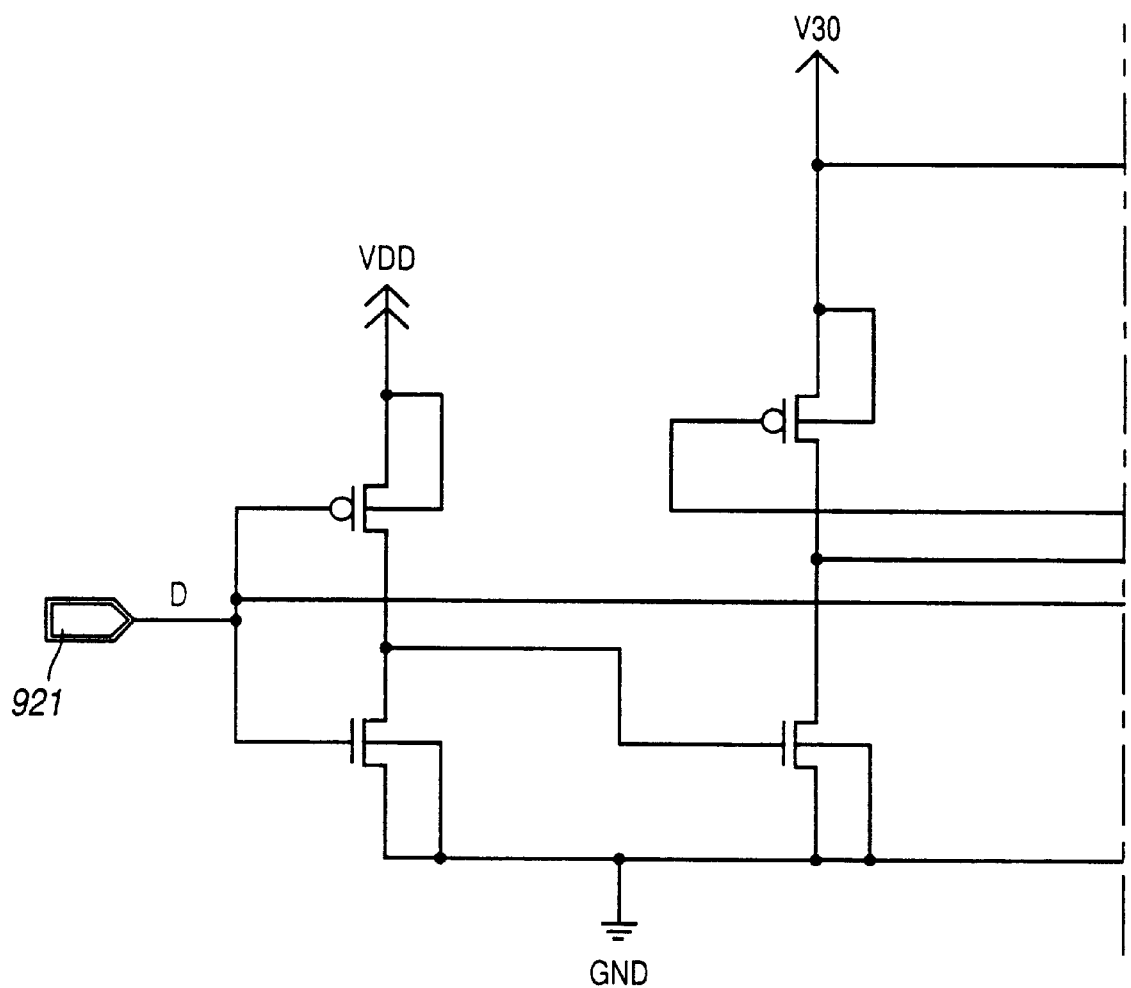
Fig.30 ( Part I )

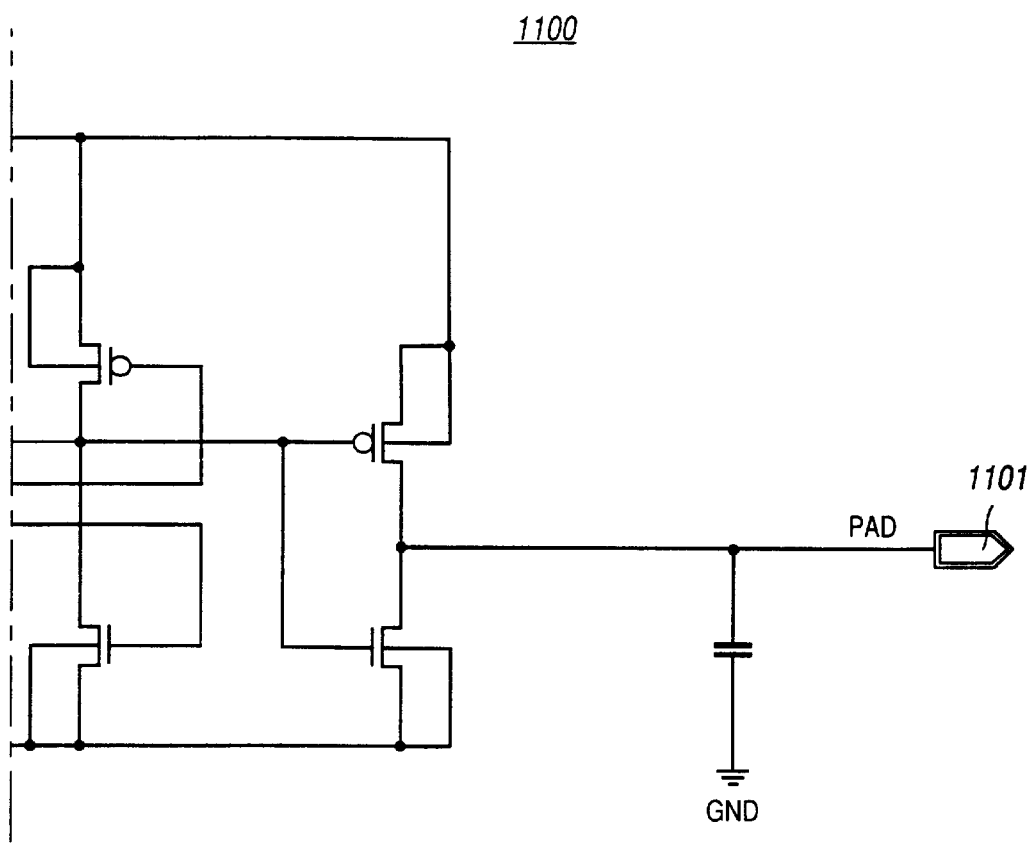
Fig.30 ( Part II )

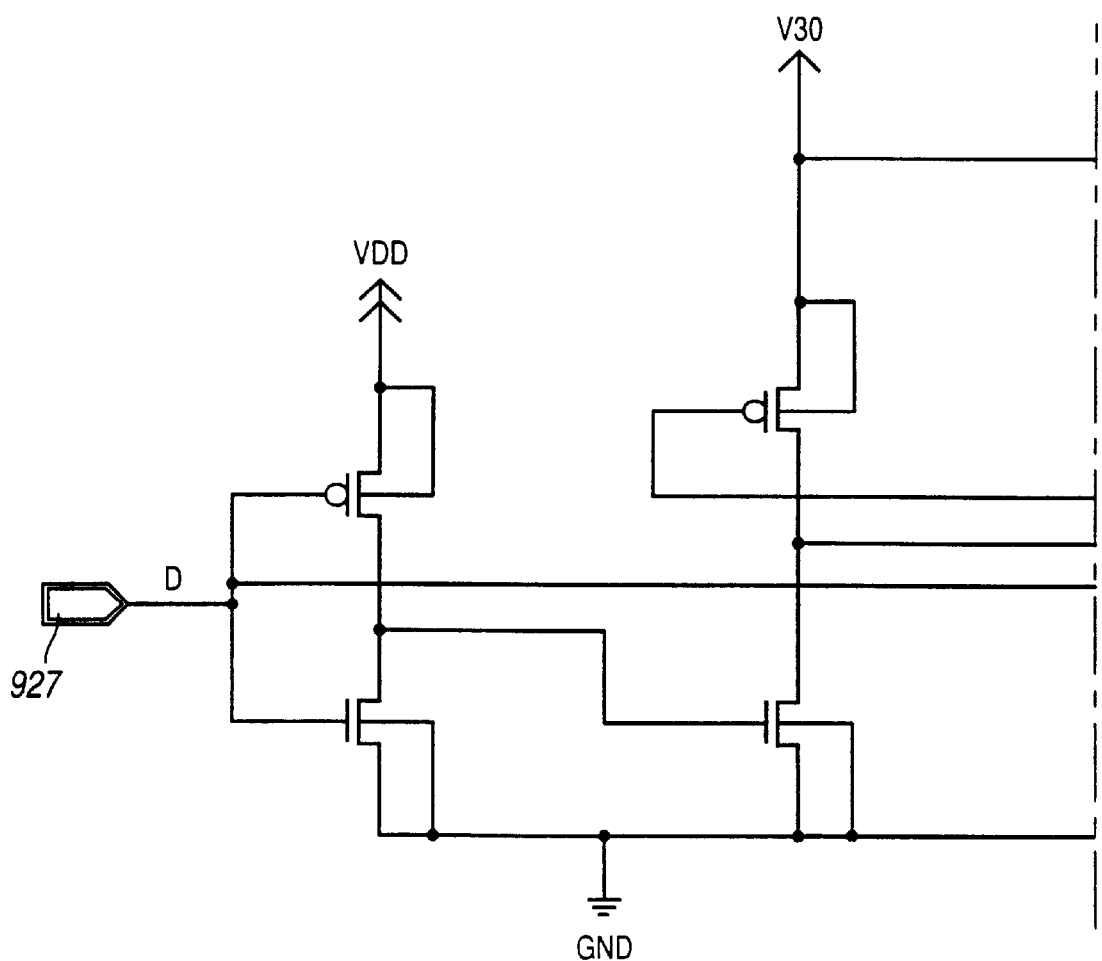
Fig.31 (Part I)

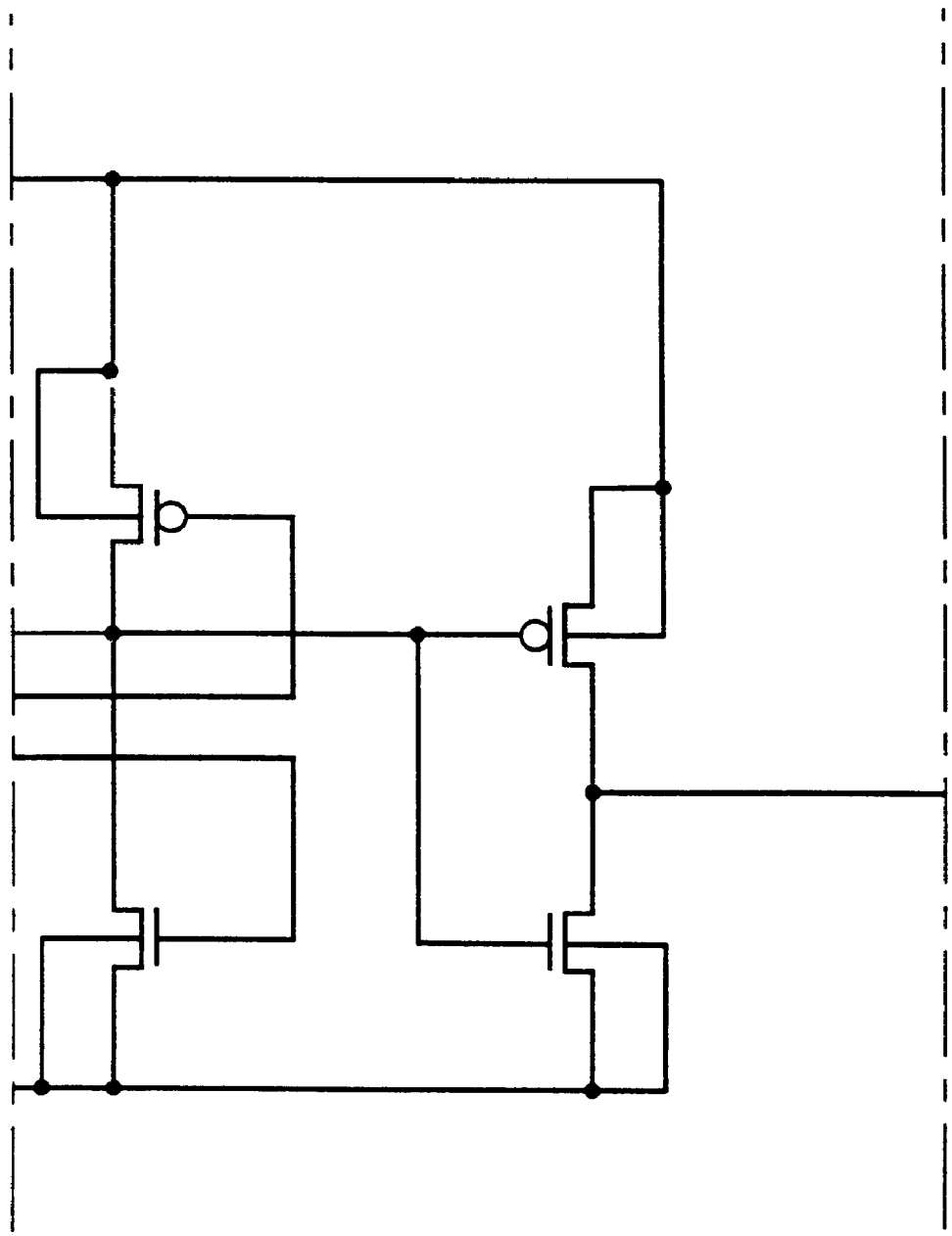
Fig.31 (Part II)

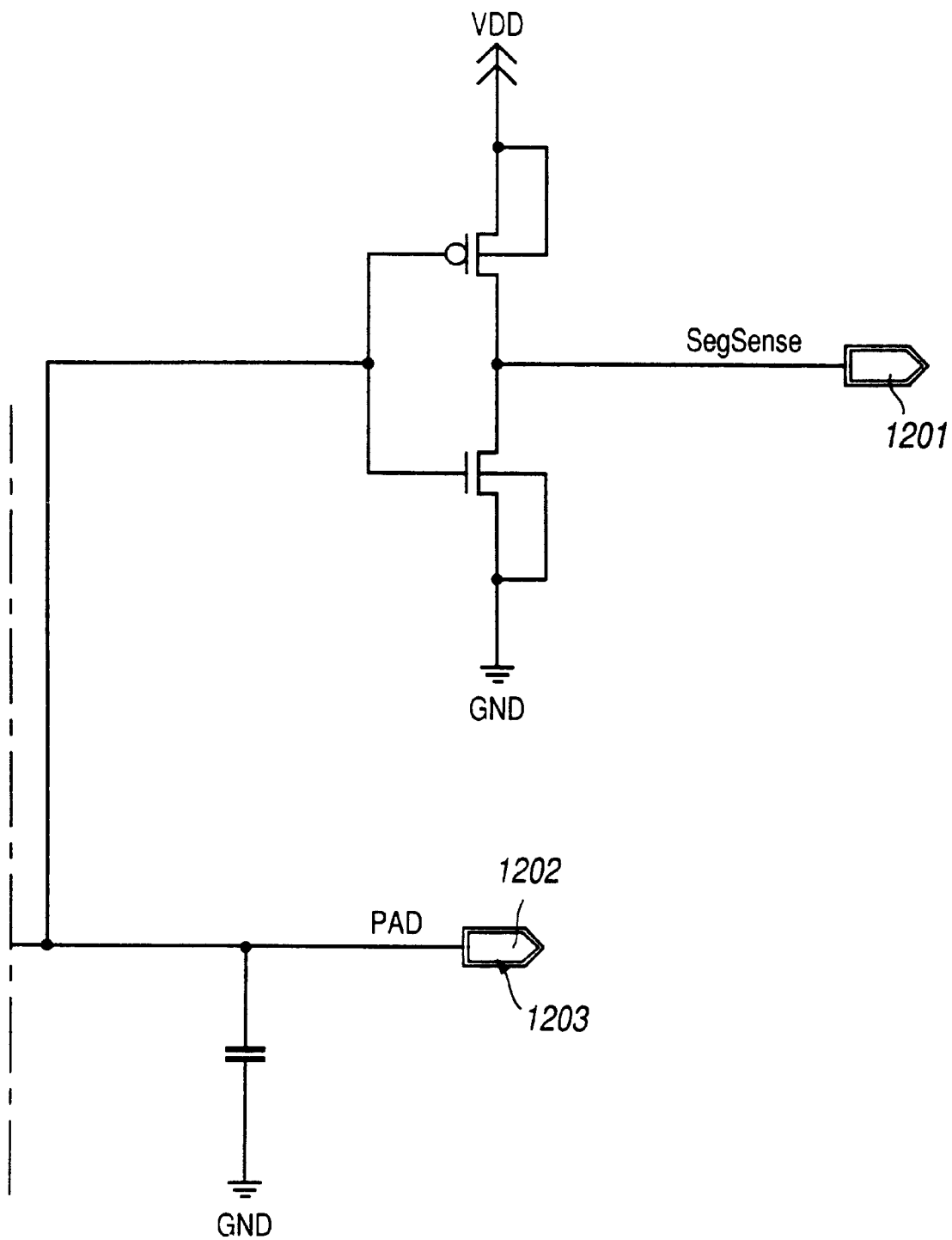
Fig.31 (Part III)

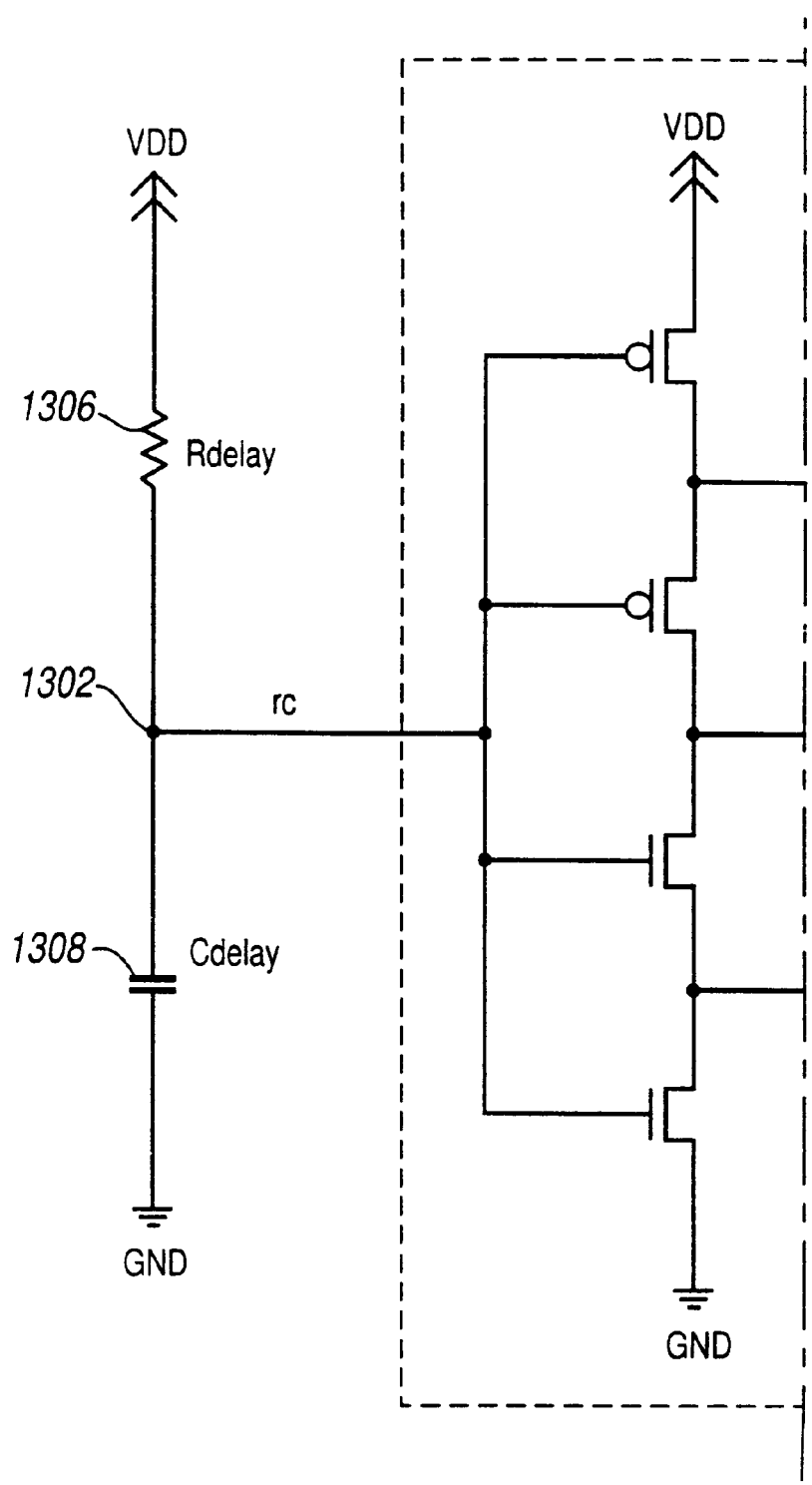
Fig.32 (Part I)

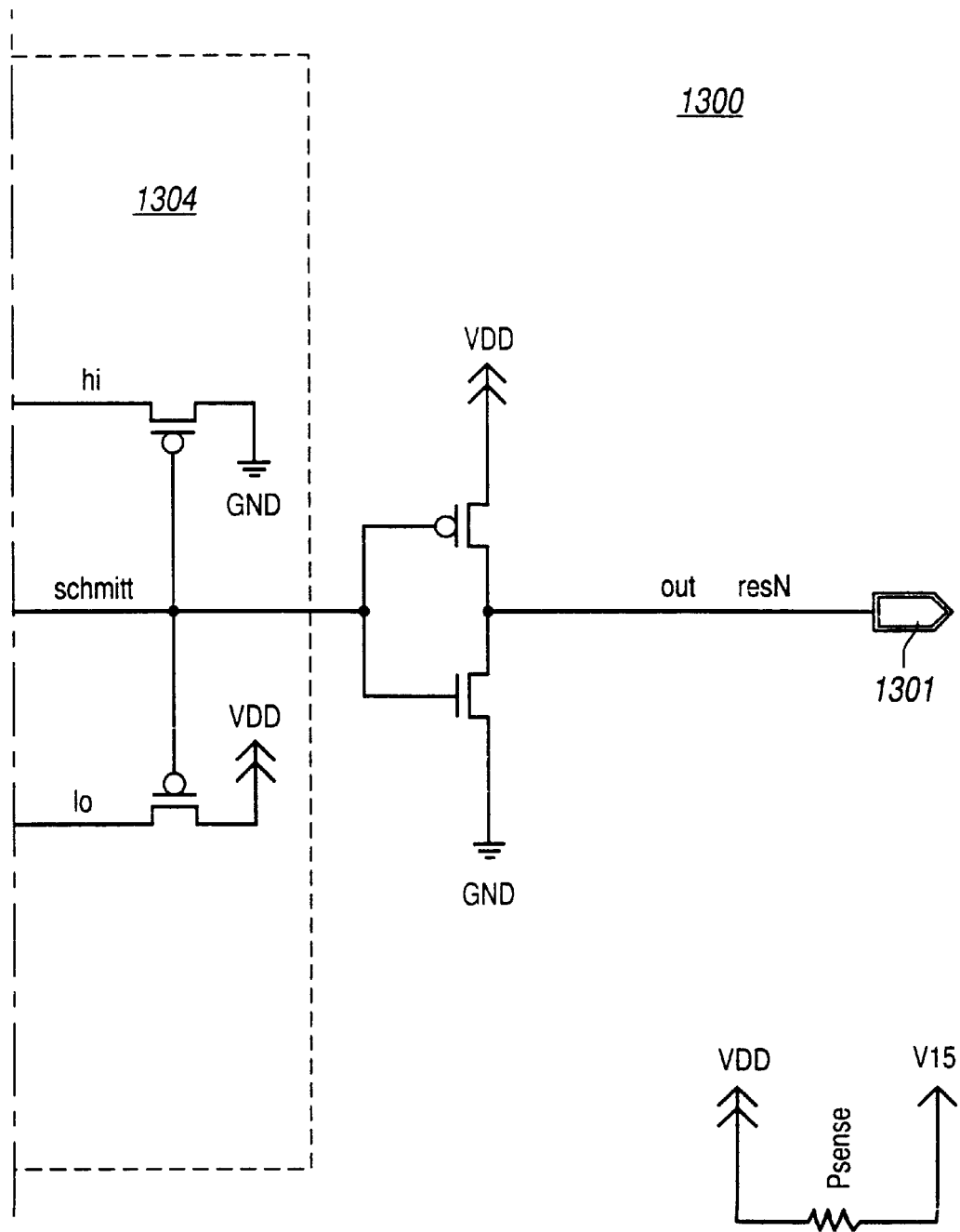
Fig.32 (Part II)

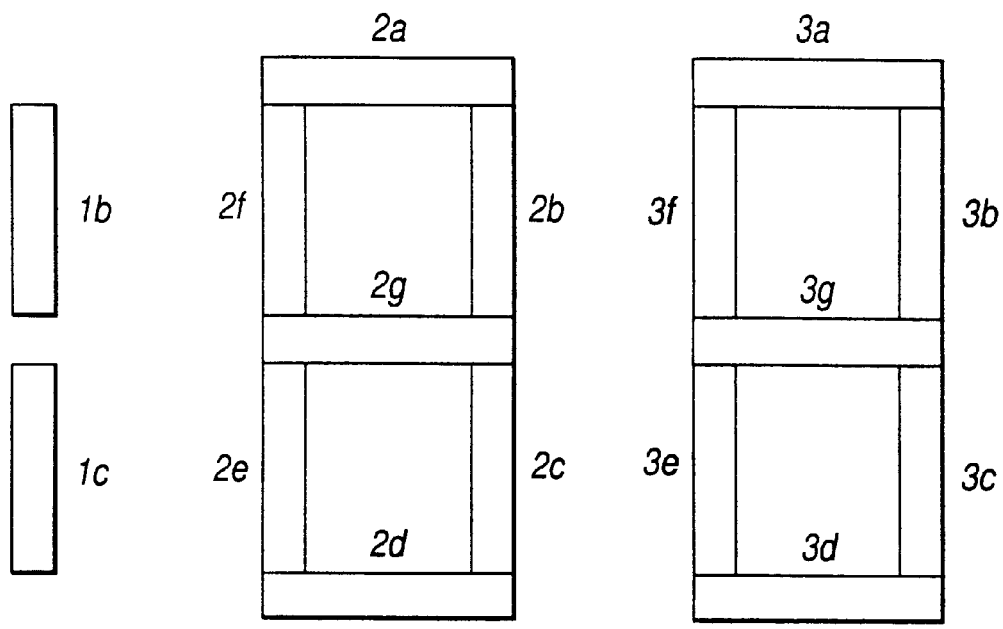

Fig.34

Phase test 1:

$3ab$  $3c\overline{e}$  $3\overline{d}$  $3f\overline{g}$  $2\overline{ab}$  $2c\overline{e}$  $2d, 1\overline{bc}$  $2fg$ Phase test 2:

$3\overline{a}b$  $3ce$  $3\overline{d}$  $3fg$  $2a\overline{b}$  $2ce$  $2\overline{d}, 1\overline{bc}$  $2\overline{f}g$ Phase test 3:

$3a\overline{b}$  $3\overline{ce}$  $3d$  $3\overline{fg}$  $2\overline{a}b$  $2\overline{ce}$  $2d, 1bc$  $2f\overline{g}$ Phase test 4:

$3\overline{ab}$  $3\overline{c}e$  $3\overline{d}$  $3\overline{fg}$  $2ab$  $2\overline{c}e$  $2\overline{d}, 1bc$  $2\overline{fg}$

Fig.35

COUNTING DEVICE AND INHALER INCLUDING A COUNTING DEVICE

The present invention relates to a counting device, and more particularly but not exclusively to a counting device for use in a dry powder inhaler.

Counting devices often store important information in the form of a count. In some applications, the corruption of such information may have adverse health or safety implications. It would therefore be desirable to reduce the likelihood of the information stored as a count being corrupted. One potential source of corruption is at the enablement of a counting device. Typically, the count in the counting device will be incremented or decremented by responding to a two-state input signal. Such an input signal is typically provided by a switch which has an on and an off state. When the switch is closed the signal is provided to the counting device which causes it to increment by one.

It would be desirable to prevent the erroneous creation of a signal which activates the counter. Such erroneous signals may arise for example by the switch bouncing so that the counting device is activated several times instead of a single time. Another possible source of an erroneous signal is if the switch is accidentally activated.

It would be desirable to provide a counting device which is less susceptible to errors caused by erroneous input.

Accordingly, the present invention provides a counting device, comprising: an input for receiving an input signal having at least three distinct input states; memory means for storing a count; and means responsive to a predetermined sequence of input states of said input signal to vary said count, wherein said predetermined sequence includes the at least three input states.

Preferably, the said means responsive to a predetermined sequence of input states comprises a state machine responsive to the predetermined sequence to vary the count by one.

Preferably, the memory means comprises a BCD counter.

A preferred embodiment of the present invention will now be described hereinbelow by way of example only with reference to the accompanying drawings, in which:

FIG. 1b illustrates an exploded perspective view of the component parts disposed within the inhaler body of the inhaler of FIG. 1a;

Figure 2A:
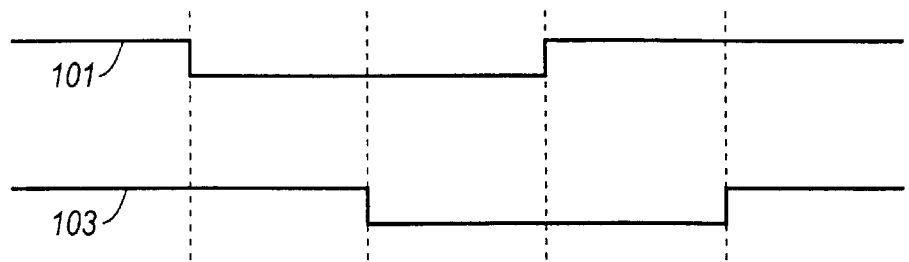
FIG. 2a illustrates a time variation in the signals 101 and 103 when a dose is administered.
Figure 2B:
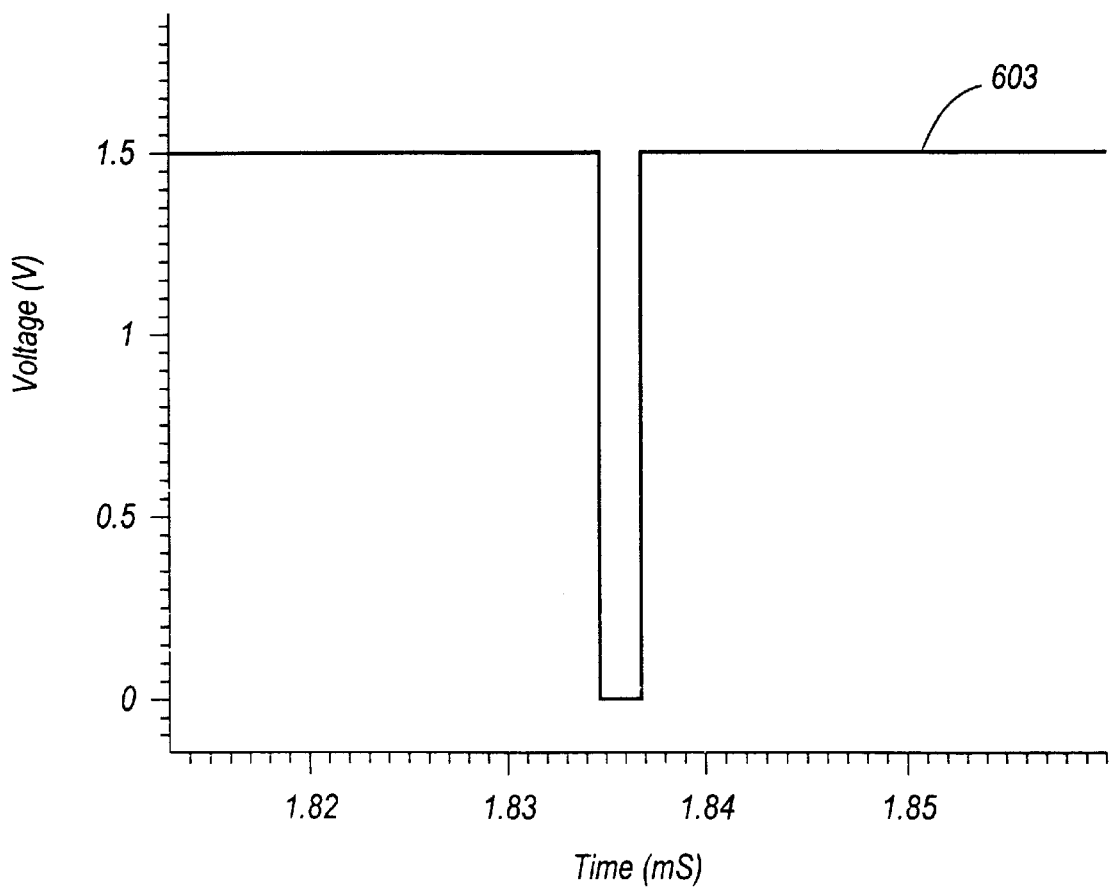
FIG. 2b illustrates the pulsed signal 603.
Figure 2C:
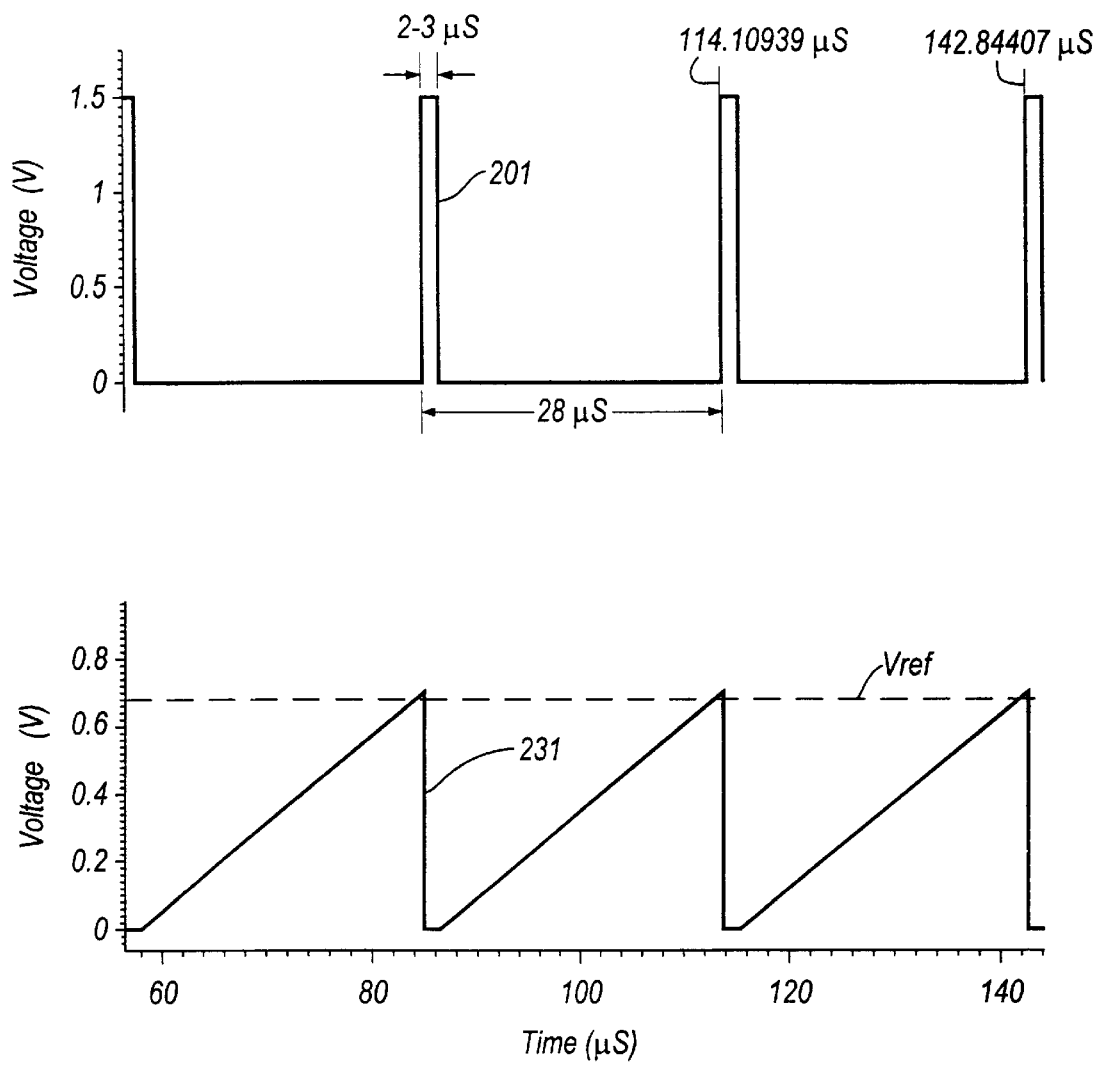
Figure 2D:
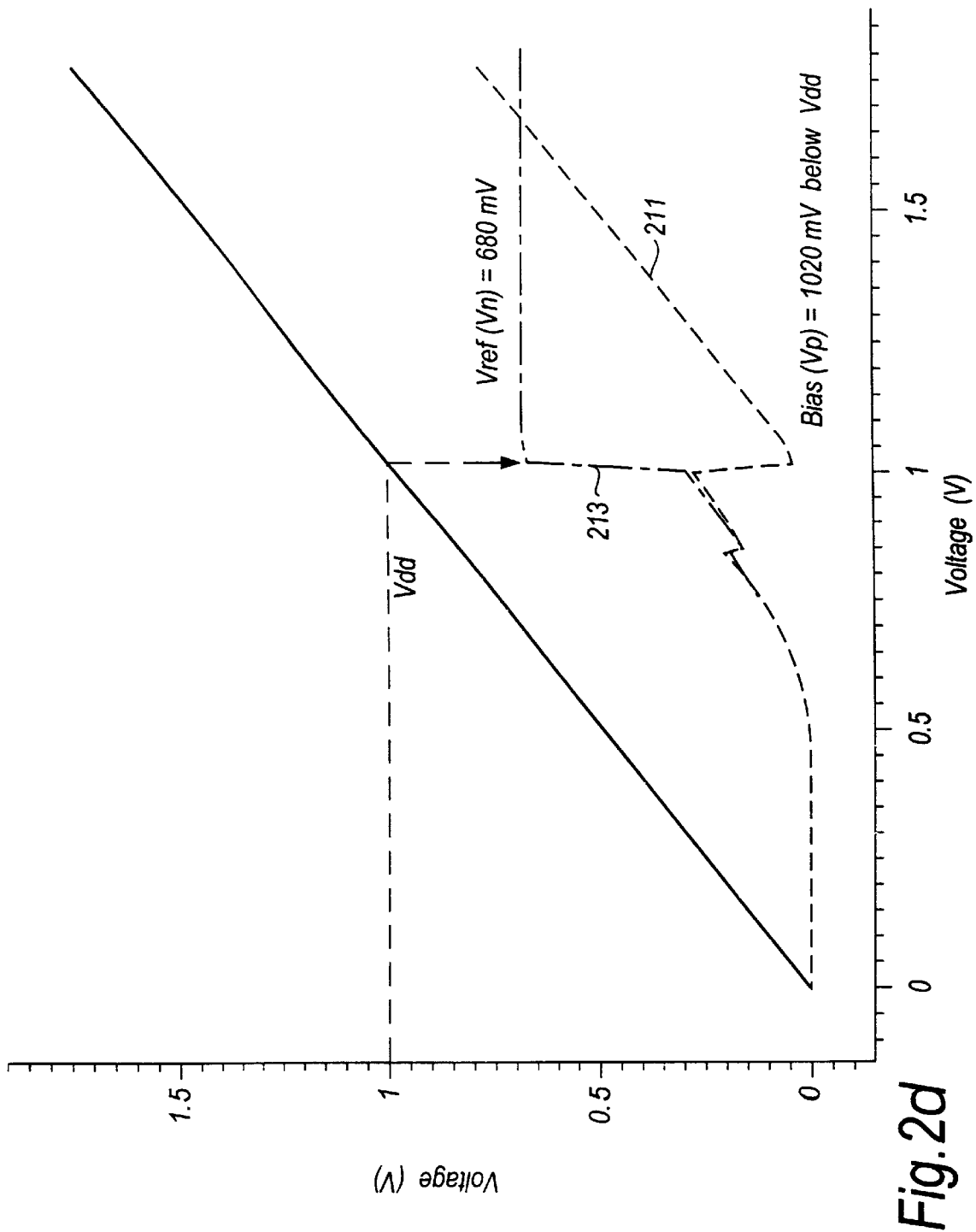
Figure 2E:
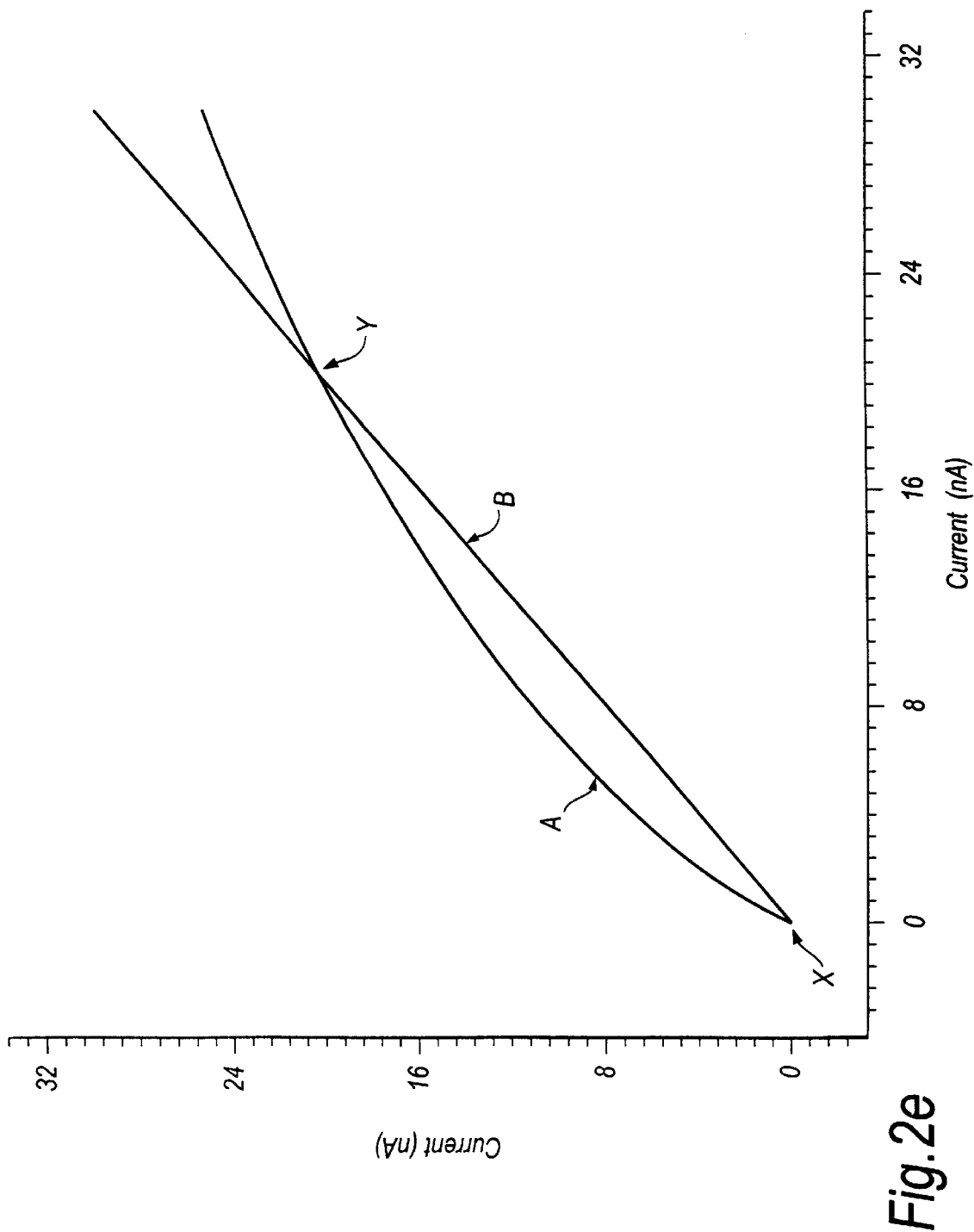
Figure 4:
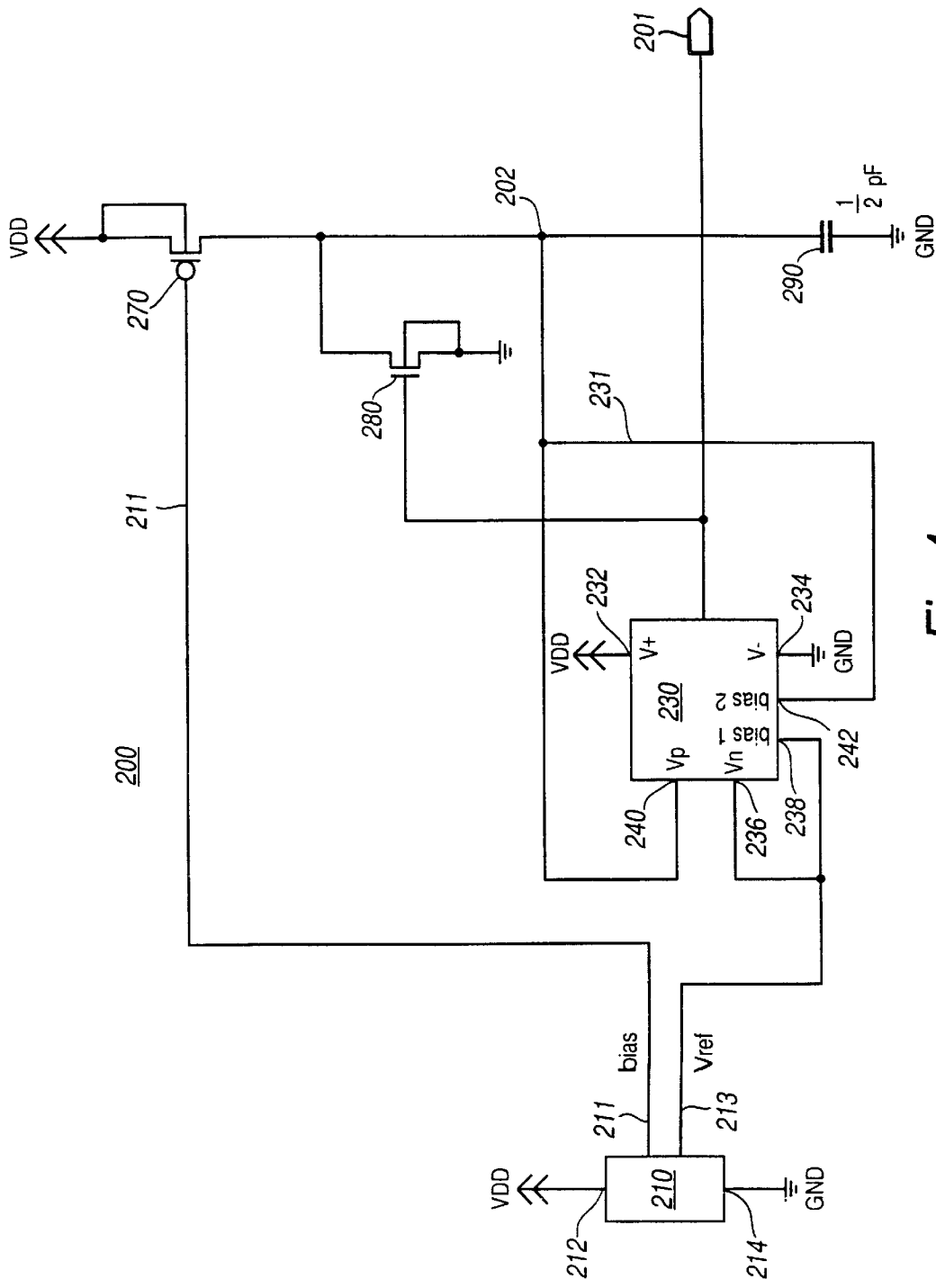
Figure 5:
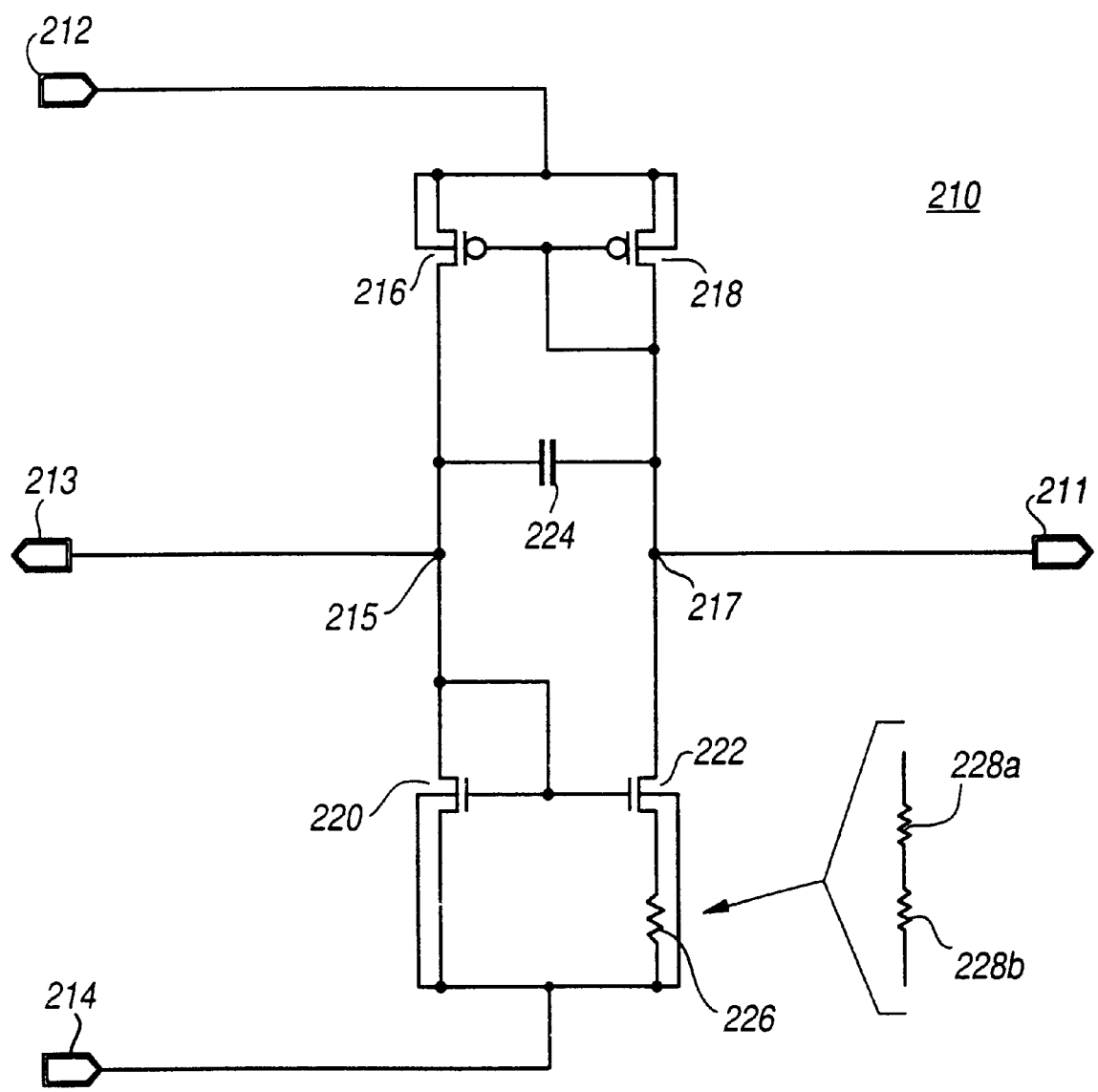
Figure 6:
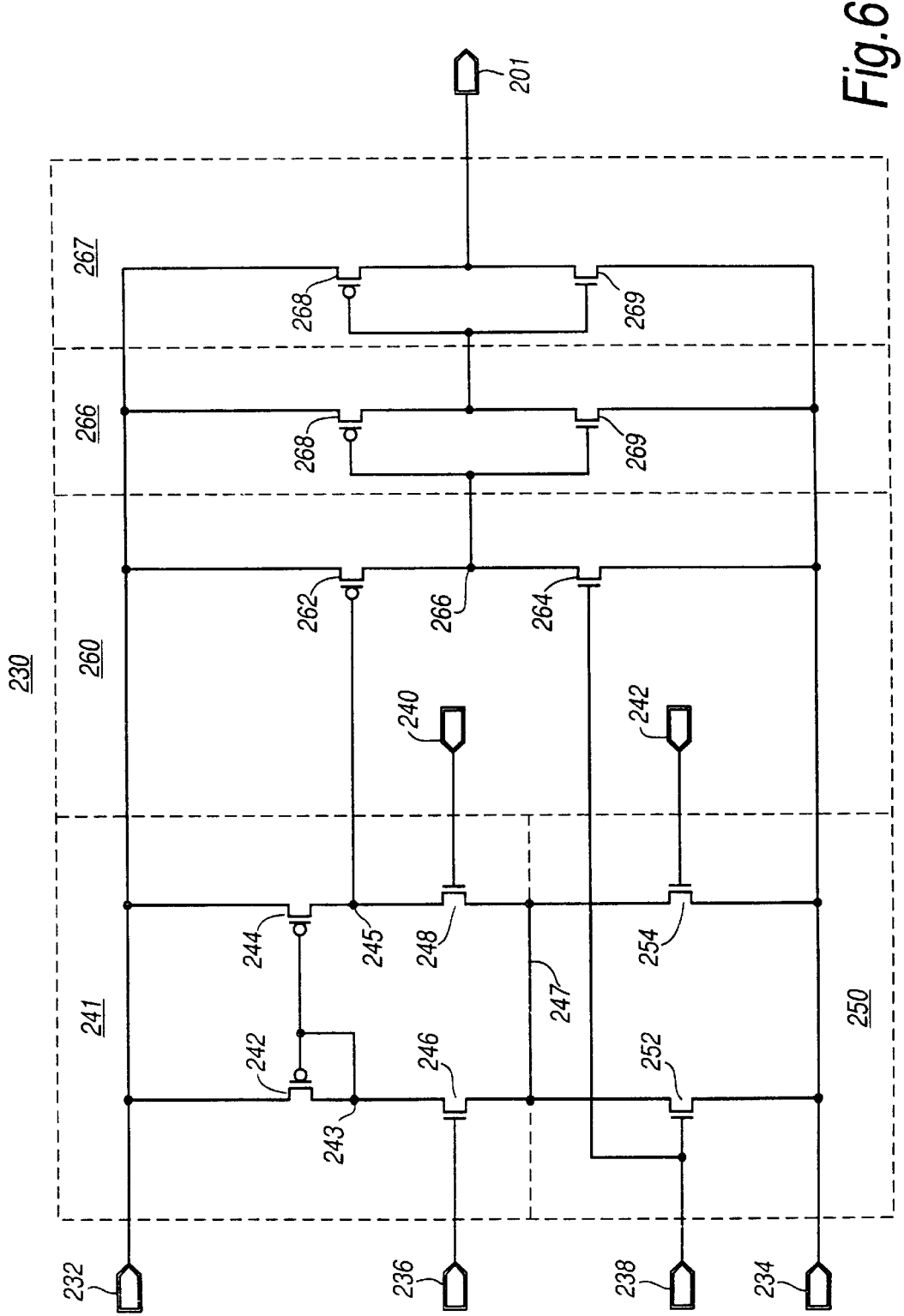
Figure 16:
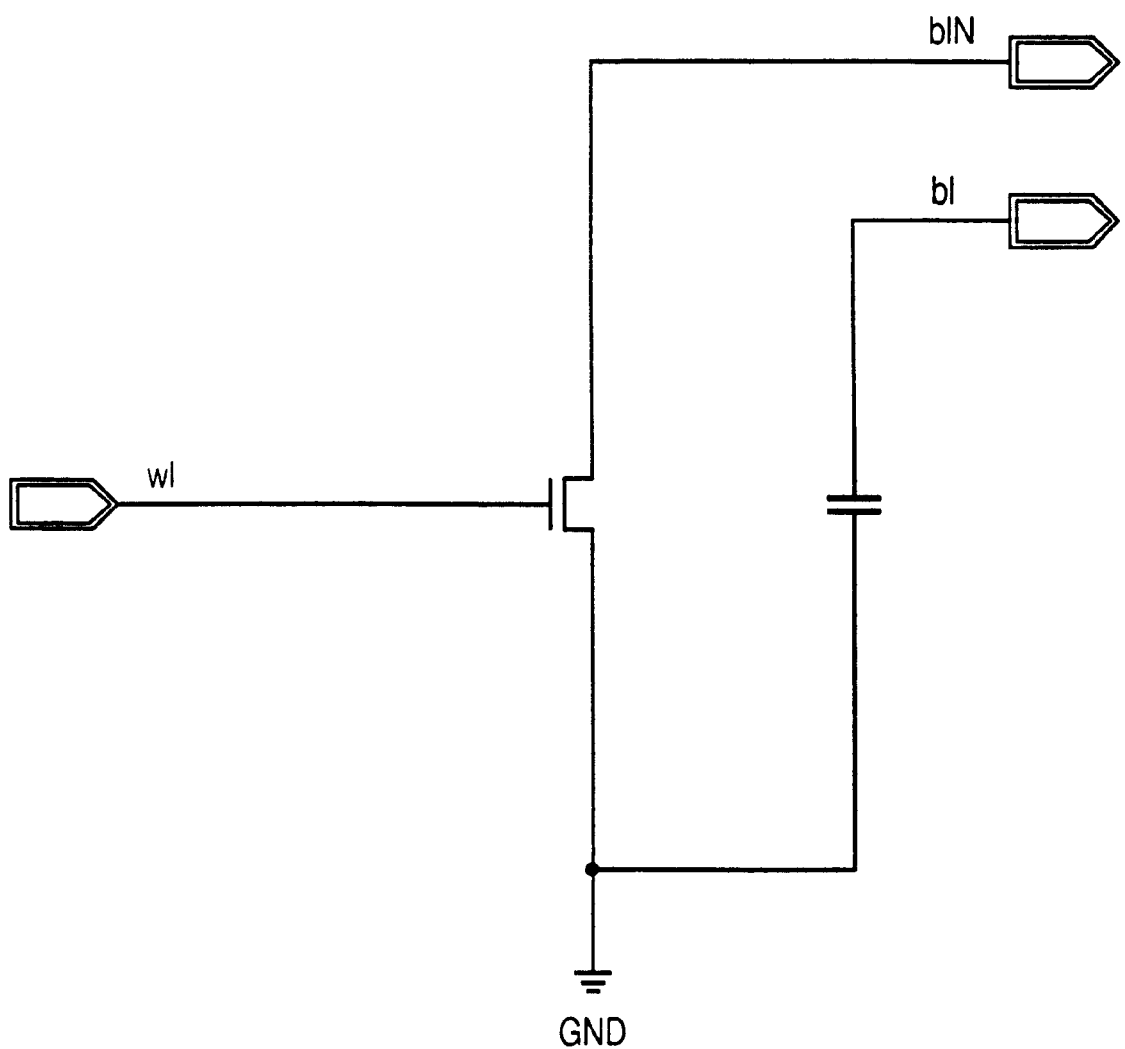
Figure 17:
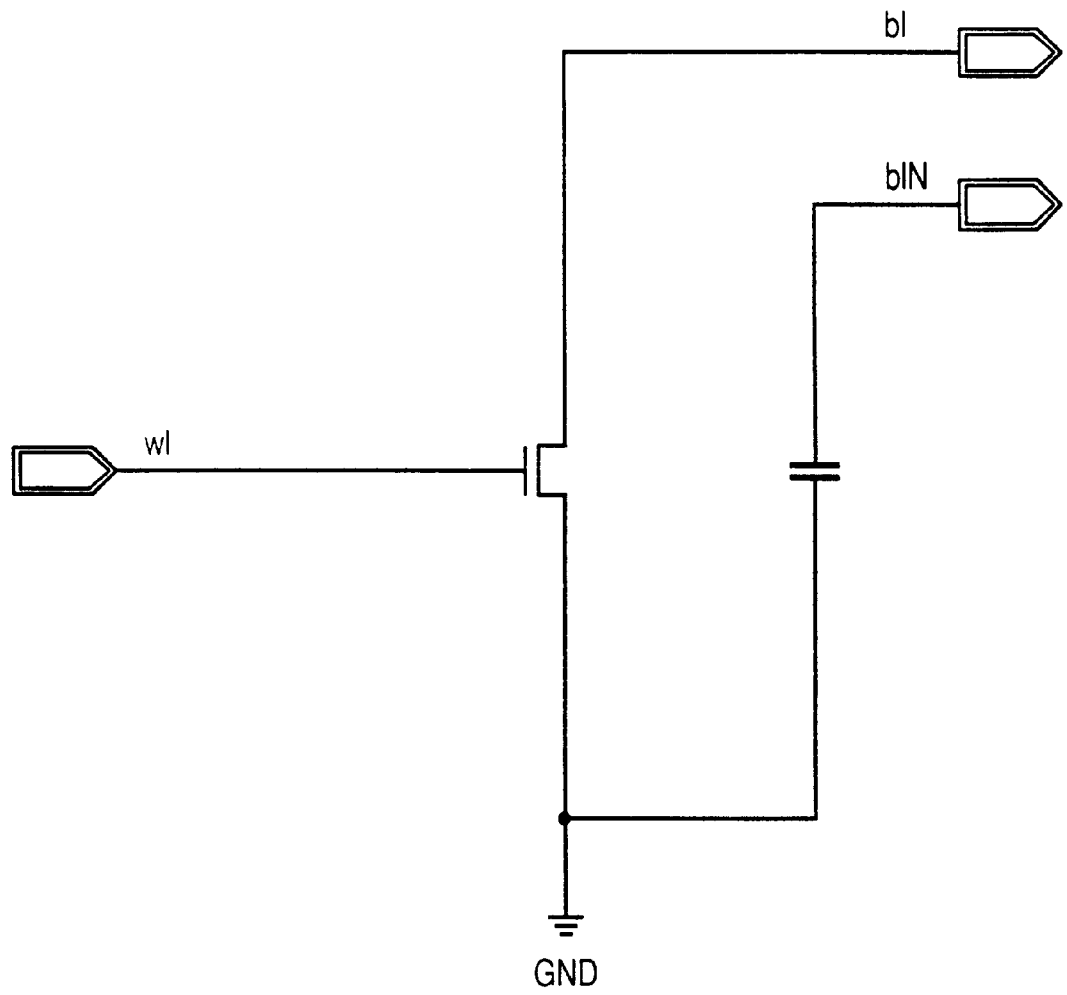
Figure 22:
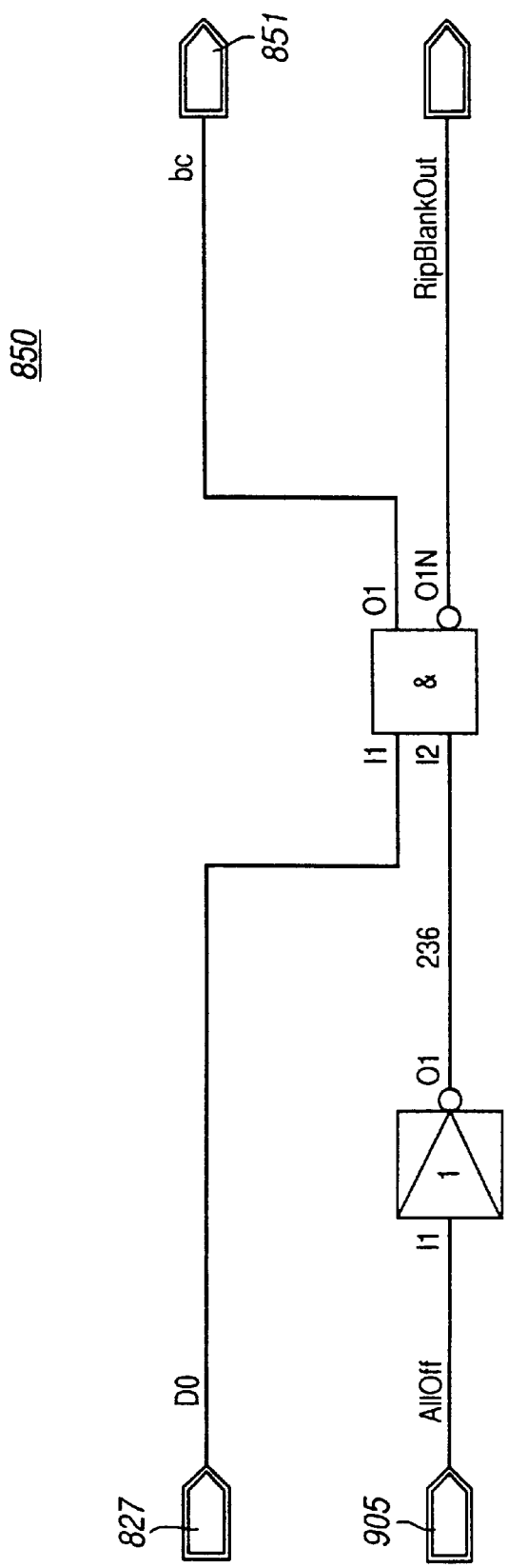
Figure 24:
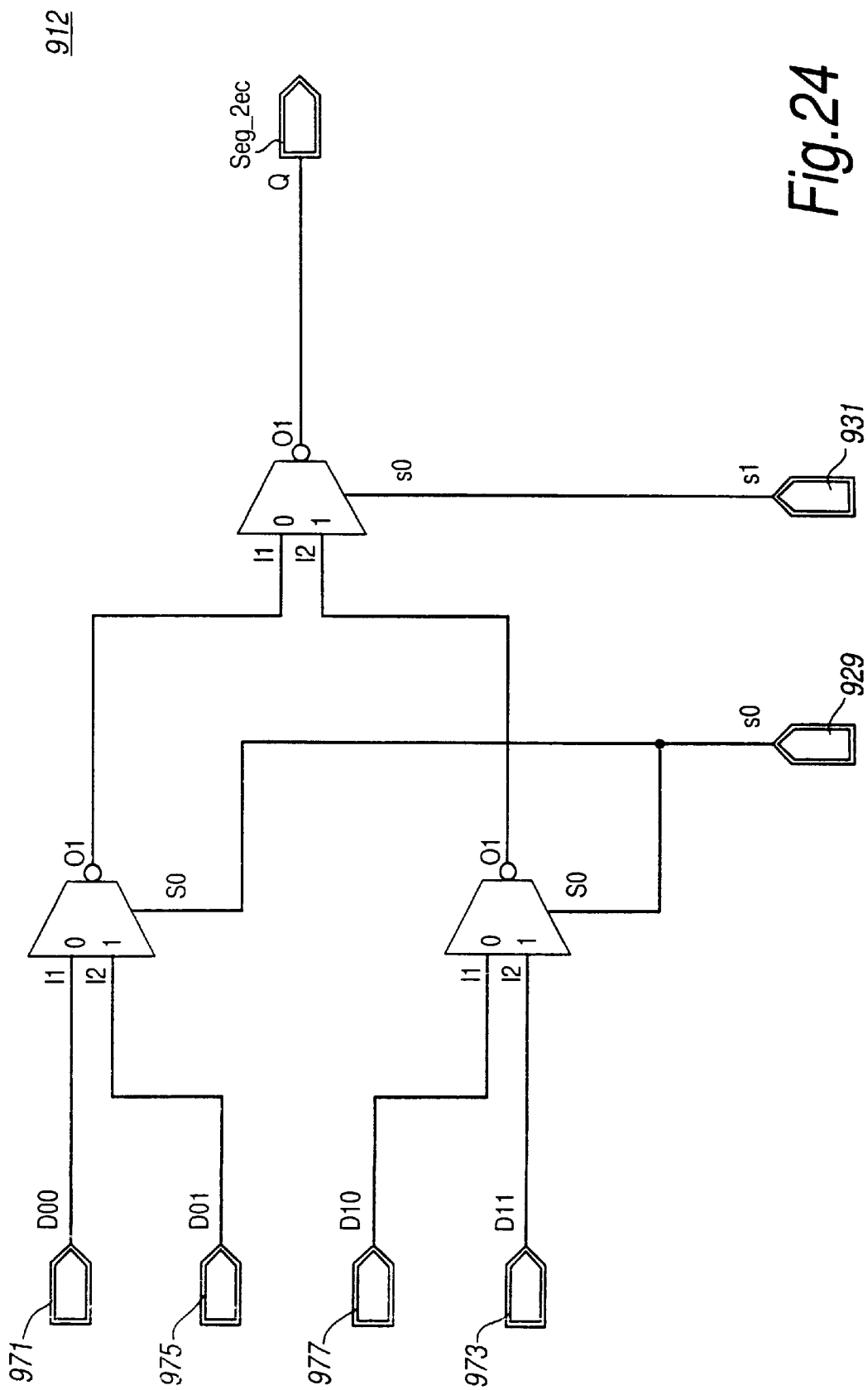
Figure 25:
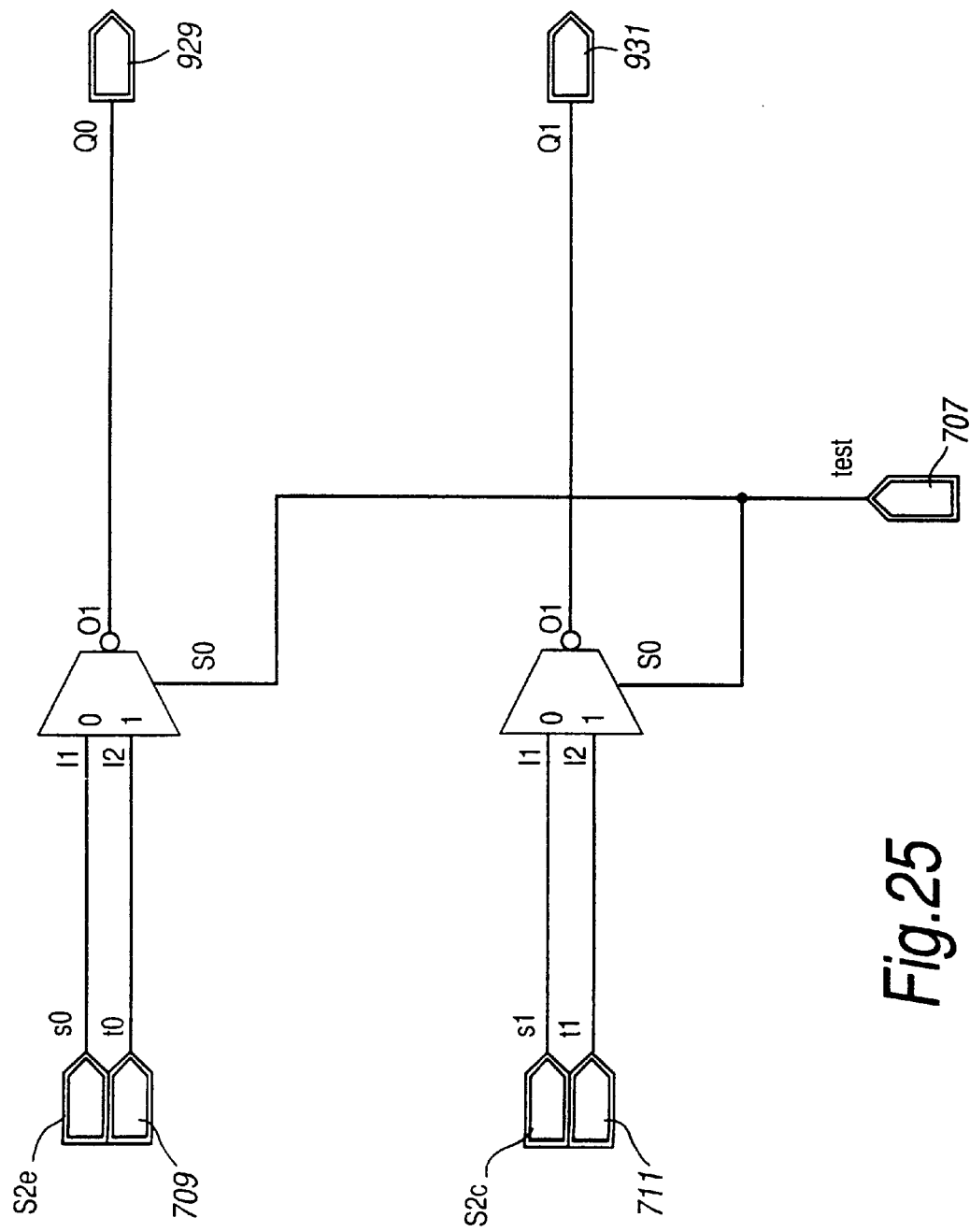
Figure 28:
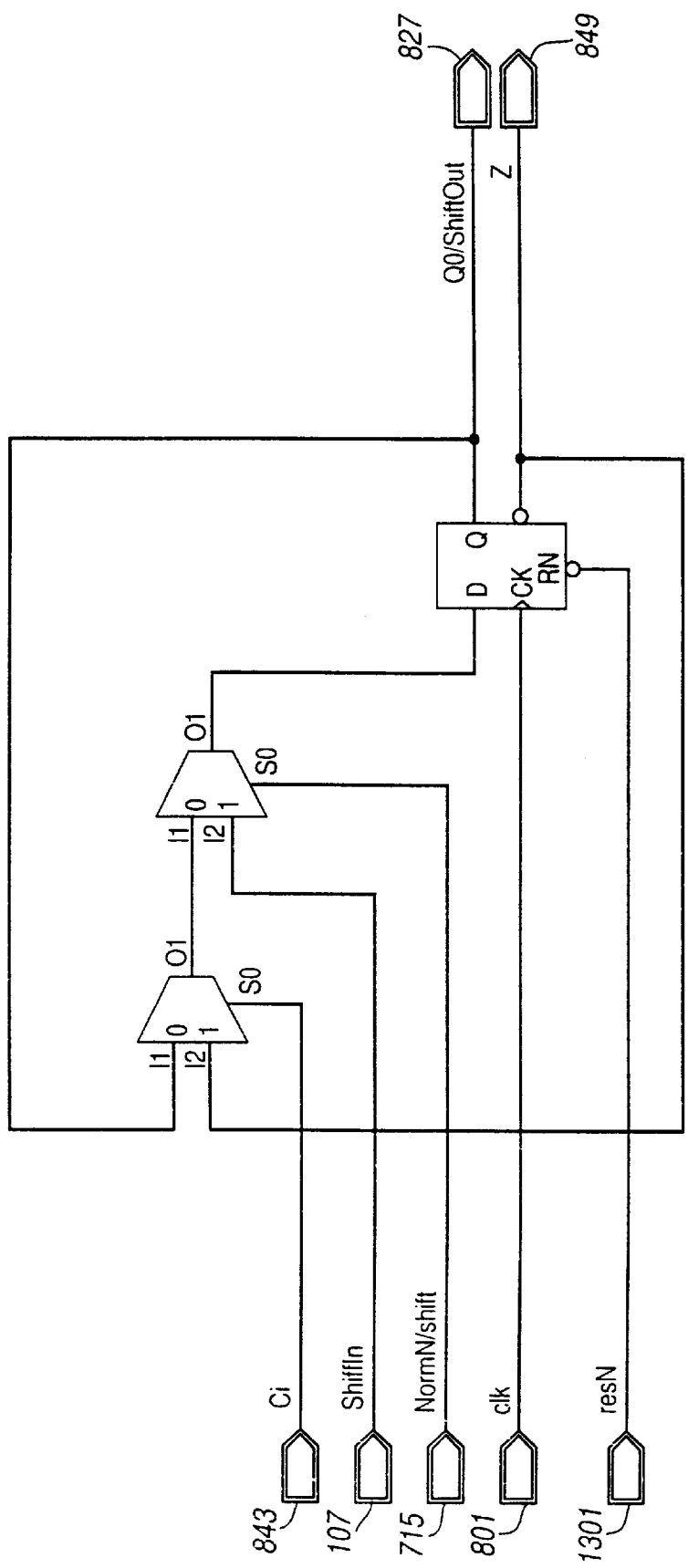
Figure 33A:
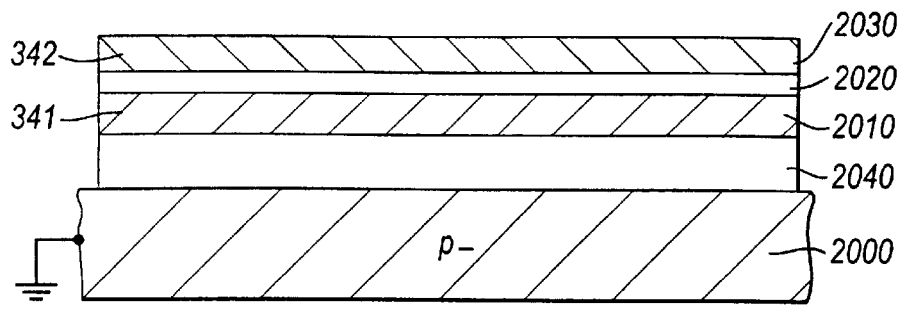
Figure 33B:
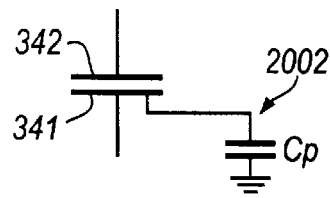
Figure 33C:
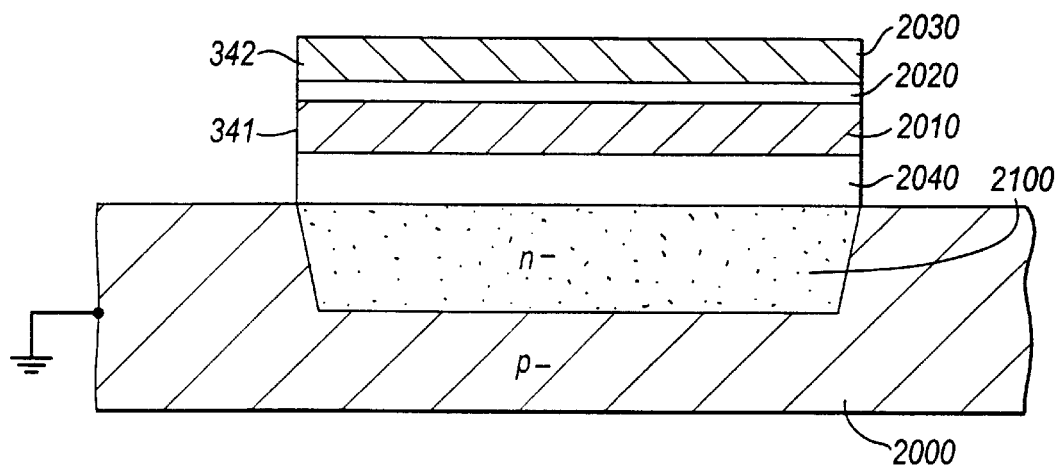
Figure 33D:
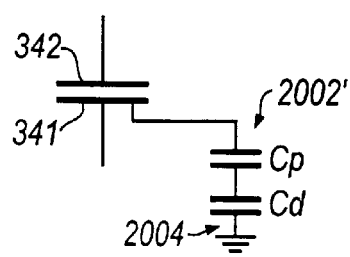

FIG. 2c illustrates the output signal 201 of an operational amplifier 230 and the signal 231 developed across the capacitor 290 in the oscillator 200;

FIG. 2d illustrates how the output reference signal 213 and the bias signal 211 the voltage reference source 210 vary with the applied voltage Vdd;

FIG. 2e illustrates the operating characteristics of the linear and non-linear current mirrors which form part of the reference voltage source 210;

FIG. 3 illustrates counting circuitry 102;

FIG. 4 illustrates an oscillator 200 which is a component of the counting circuitry 102 illustrated in FIG. 3;

FIG. 5 illustrates a reference voltage source 210 which is a component of the oscillator 200 illustrated in FIG. 4;

FIG. 6 illustrates an operational amplifier 230 which is a component of the oscillator 200 illustrated in FIG. 4;

FIG. 7 illustrates a voltage booster 300 which is a component of the counting circuitry 102 illustrated in FIG. 3;

FIG. 8 illustrates a clock generator 400 which is a component of the counting circuitry 102 illustrated in FIG. 3;

FIG. 9 illustrates an input driver 500 which is a component of the counting circuitry 102 illustrated in FIG. 3;

FIG. 10 illustrates a switch input detector 600 which is a component of the counting circuitry 102 illustrated in FIG. 3;

FIG. 11 illustrates debounce circuitry 602 which is a component of the switch input detector 600 illustrated in FIG. 10;

FIG. 12 illustrates a quadrature decoder 620 which is a component of the switch input detector 600 illustrated in FIG. 10;

FIG. 13 illustrates start-up circuitry 700 which is a component of the counting circuitry 102 illustrated in FIG. 3;

FIG. 14 illustrates a register 720 which is a component of the start-up circuitry 700 illustrated in FIG. 13;

FIG. 15 illustrates a ROM 731 which is a component of the start-up circuitry 700 illustrated in FIG. 13;

FIGS. 16 and 17 illustrate separate components of the ROM 731 illustrated in FIG. 15;

FIG. 18 illustrates count and display circuitry 900 which is a component of the counting circuitry 102 illustrated in FIG. 3;

FIG. 19 illustrates a counter 810 which is a component of the count and display circuitry 900 illustrated in FIG. 18;

FIG. 20 illustrates decision circuitry 860 which is part of the count and display circuitry 900 illustrated in FIG. 18;

FIG. 21 illustrates decoder 830 which is part of the count and display circuitry 900 illustrated in FIG. 18;

FIG. 22 illustrates decoder 850 which is a component of the count and display circuitry 900 illustrated in FIG. 21;

FIG. 23 illustrates an LCD driver 910 which is a component of the count and display circuitry 900;

FIG. 24 illustrates a multiplexer 912 which is a component of the LCD driver 910 illustrated in FIG. 23;

FIG. 25 illustrates test circuitry 928 which is a component of the LCD driver 910 illustrated in FIG. 23;

FIG. 26 illustrates wave generator 970 which is a component of the LCD driver 910 illustrated in FIG. 23;

FIGS. 27 illustrates a decrementor 820 which is a component of the counter 810 illustrated in FIG. 19;

FIG. 28 illustrates a decrementor 860 which is a component of the counter 810 illustrated in FIG. 19;

FIG. 29 illustrates a conventional LCD backplane driver 1000 which is a component of the counting circuitry 102 illustrated in FIG. 3;

FIG. 30 illustrates a conventional LCD segment driver 1100 which is a component of the counting circuitry 102 illustrated in FIG. 3;

FIG. 31 illustrates an adapted LCD segment driver 1200 which is a component of the counting circuitry illustrated in FIG. 3;

FIG. 32 illustrates reset circuitry 1300 which is a component of the counting circuitry illustrated in FIG. 3;

FIGS. 33a and 33b illustrate a first capacitor;

FIGS. 33c and 33d illustrate a second capacitor;

FIG. 34 illustrates the segments of the LCD; and

FIG. 35 is a table.

Figure 1A:
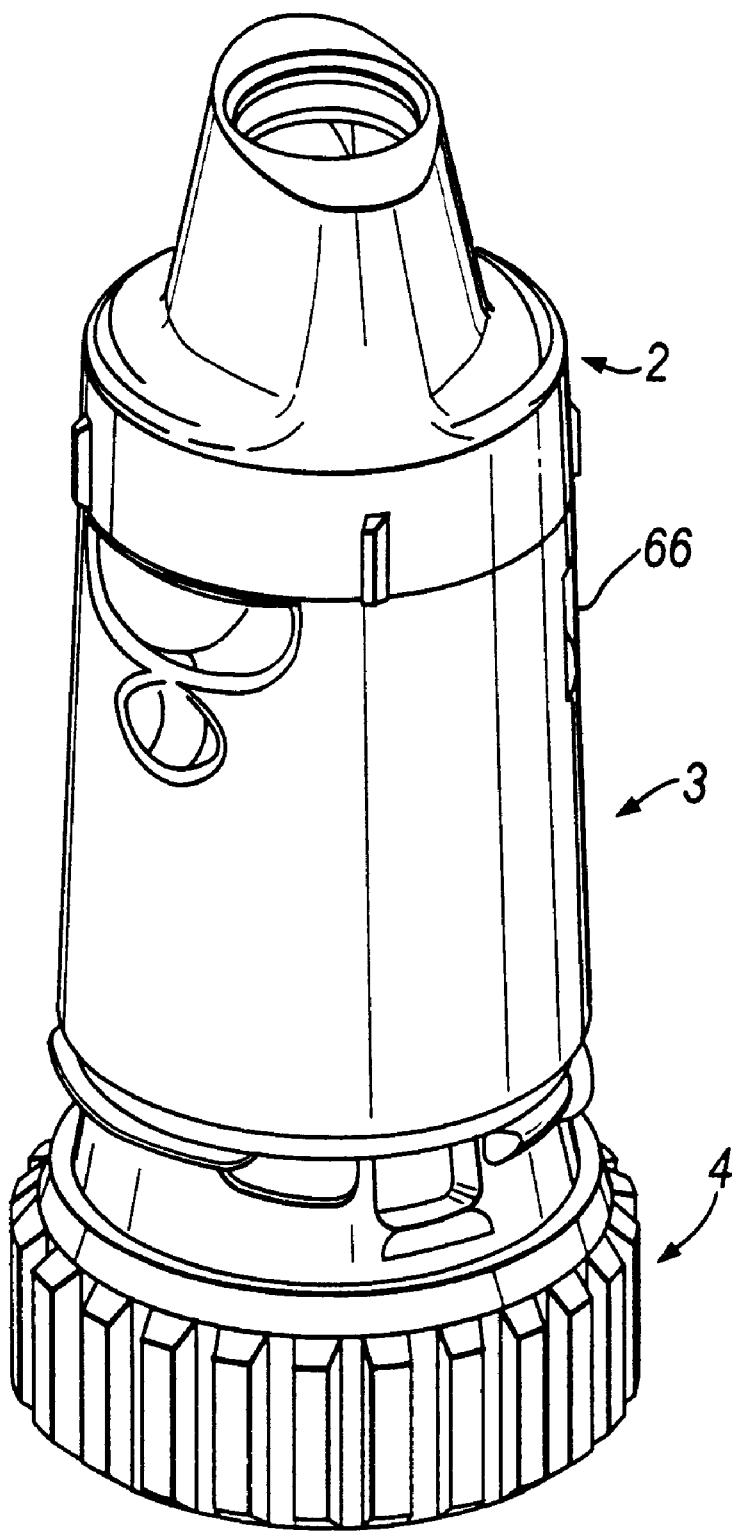
FIG. 1a illustrates a perspective view of a powder inhaler for administering powder by inhalation.
Figure 1B:
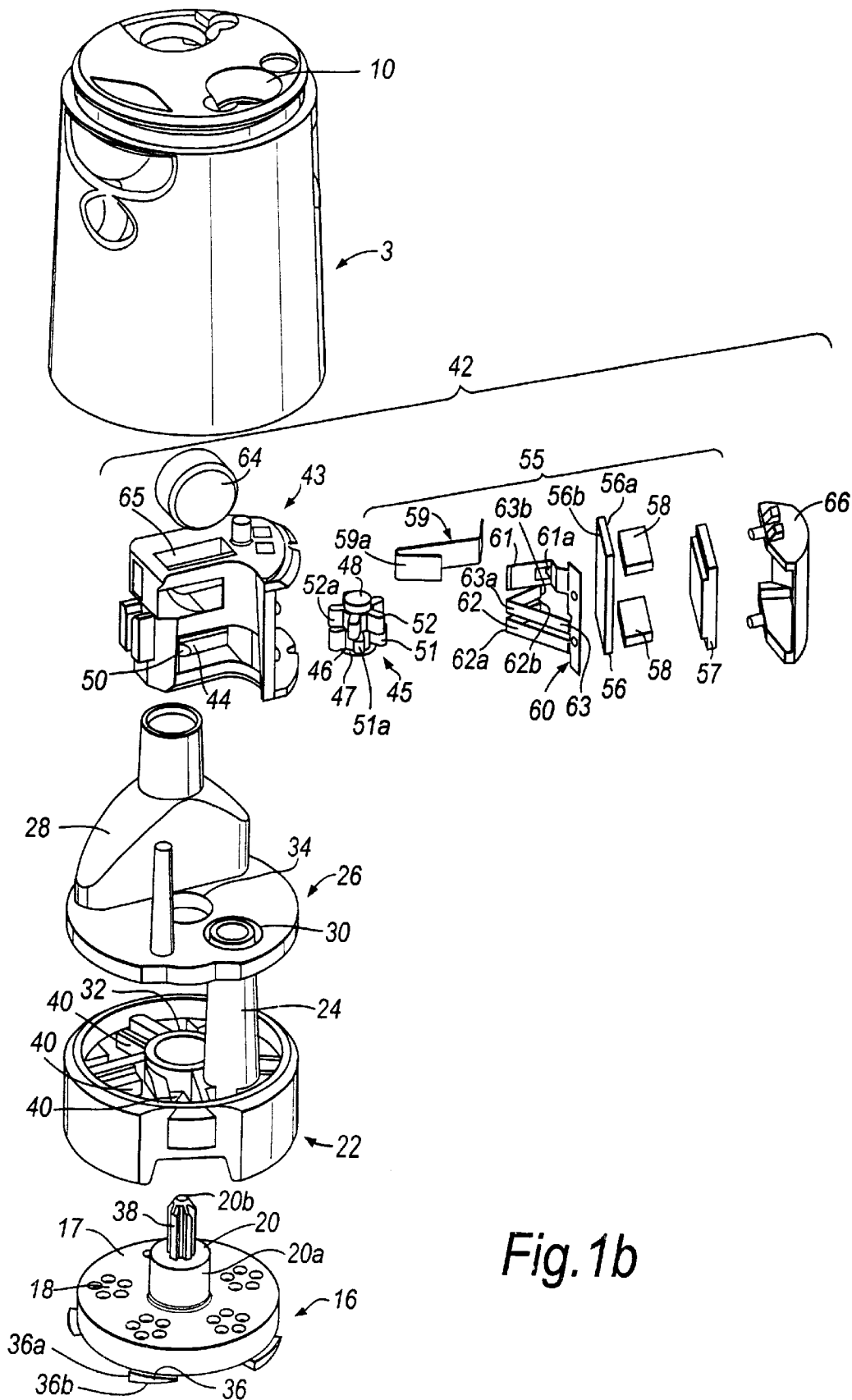

FIGS. 1a and 1b illustrate a powder inhaler for administering powder by inhalation. The inhaler comprises a mouthpiece 2, an inhaler body 3 and a rotatable grip portion 4 for operating a dosing mechanism for providing doses of powder for inhalation.

Within the inhaler body 3 are housed the component parts of the dosing mechanism. These component parts include a dosing unit 16 which comprises a member 17 having a planar upper surface in which a plurality of dosing elements 18 are provided and a shaft 20 which extends axially from the centre of the member 17, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. In this way, the inhalation unit 22 and the storage unit 26 are fixed in position in relation to one another and the dosing unit 16 can be rotated relative thereto.

The dosing unit 16 comprises a plurality of dosing elements 18, each in the form of a plurality of through holes, which are equi-spaced circularly about the central shaft 20. In this embodiment the dosing unit 16 includes five dosing elements 18 which are angularly spaced apart from one another by an angle of 72 degrees. The dosing unit 16 further comprises a plurality of wedge-shaped elements 36, in the same number and spacing as the dosing elements 18, disposed around the outer periphery of the member 17. Each wedge-shaped element 36 has a first, axially-directed surface 36a which faces in one sense, in this embodiment in the clockwise sense when viewed from above, and a second surface 36b which has a component which faces in the opposite, counter-clockwise sense. In use, the dosing unit 16 is rotated by rotating the grip portion 4 in the opposite sense, that is, the counter-clockwise sense when viewed from above, the grip portion 4 including a resilient member (not illustrated) which is configured to engage with the axially-directed surface 36a of a respective one of the wedge-shaped elements 36 so as to rotate the dosing unit 16 between first and second angularly-spaced positions, in this embodiment positions angularly spaced 72 degrees apart, by pushing the respective wedge-shaped element 36. On rotation of the grip portion 4 in the one, clockwise sense between the second and the first angularly-spaced positions, the dosing unit 16 remains stationary and the resilient member is located behind the axially-directed surface 36a of the adjacent wedge-shaped element 36; the resilient member riding over the second surface 36b of the adjacent wedge-shaped element 36. Further, in this embodiment, the central shaft 20 comprises a first, lower part 20a, the outer surface of which is generally cylindrical and acts as a bearing surface in the central openings 32, 34 in the inhalation unit 22 and the storage unit 26, and a second, upper part 20b which is of smaller radial dimension than the first part 20a and includes a plurality of external splines 38 on the outer surface thereof.

In this embodiment the storage unit 28 is open at the bottom such that in use powder is provided to the dosing unit 16 under the action of gravity and the inhalation unit 22 further comprises scrapers 40 which are resiliently biased against the upper surface of the member 17 in which the dosing elements 18 are provided. In this way, as the dosing unit 16 is rotated, the dosing elements 18 are filled with powder by the scrapers 40. Powder is prevented from passing through the dosing elements 18 by a plate (not illustrated) which is disposed beneath the dosing unit 16.

Within the inhaler body 3 is also housed a dose counting unit 42 for counting the number of operations of the grip portion 4 in providing doses of powder to the inhalation channel 24. The dose counting unit 42 is located on the storage unit 26 between the storage member 28 thereof and the inhalation channel 24.

The dose counting unit 42 comprises a body part 43 which includes a first cavity 44 and a rotor 45 which is disposed in the first cavity 44. The rotor 45 comprises a hollow shaft 46 which includes first and second bearing surfaces 47, 48 at opposed ends thereof, which first and second bearing surfaces 47, 48 are configured to fit respectively within lower and upper recesses in opposed surfaces of the first cavity 44. The first bearing surface 47 and the lower recess are of different, in this embodiment larger, dimension than the second bearing surface 48 and the upper recess so as to ensure that the rotor 45 is fitted in the first cavity 44 with the correct orientation. The outer surface of the shaft 46 includes first and second axially-spaced cam surfaces 51, 52, each including a plurality of cams 51a, 52a of the same number. The cams 51a, 52a on the first and second cam surfaces 51, 52 have rounded distal ends and are circumferentially equi-spaced. In this embodiment each cam surface 51, 52 includes five cams 51a, 52a which are angularly spaced apart from one another by an angle of 72 degrees, with the corresponding cams 51a, 52a on the first and second cam surfaces 51, 52 being angularly shifted by a predetermined angle, typically about 18 degrees, such that the cams 51a on the first cam surface 51 are forward of the corresponding cams 52a on the second cam surface 52 in the sense of rotation, in this embodiment in the counter-clockwise sense when viewed from above. The inner surface of the shaft 46 includes a plurality of internal splines 54 which are configured to receive the external splines 38 on the upper part 20b of the shaft 20 of the dosing unit 16 so as rotationally to fix the rotor 45 relative to the dosing unit 16, whereby the rotor 45 is rotated concomitantly with the dosing unit 16.

The dose counting unit 42 further comprises an electrical device 55 which comprises a printed circuit board 56 which is mounted to the body part 43, the printed circuit board 56 including an integrated circuit 102 for counting input pulses corresponding to the number of operations of the grip portion 4 in providing doses of powder to the inhalation channel 24 and driving an electronic display 57, an electronic display 57, in this embodiment a liquid crystal display, for displaying either the number of doses provided to the inhalation channel 24 or the number of doses remaining in the storage chamber 28 which is connected to one side 56a of the printed circuit board 56 by first and second elastomeric conducting elements 58 (so-called zebra strips) and a first conductive member 59 connected to the other side 56b of the printed circuit board 56. The first conductive member 59 is a gold-plated element and comprises a resilient arm 59a which is configured to contact one of the terminals, in this embodiment the anode terminal, of a battery cell 64. The electrical device 55 further comprises a second conductive member 60 which is mounted to the body part 43. The second conductive member 60 is a gold-plated element and comprises a first resilient arm 61 which is configured to contact the other of the terminals, in this embodiment the cathode terminal, of a battery cell 64 and includes a contact pad 61a which contacts the respective terminal on the printed circuit board 56, a second resilient arm 62 which acts as a first switch element 80a and a third resilient arm 63 which acts as a second switch element 80b. The second and third arms 62, 63 are identical in shape and include a bend 62a, 63a which encloses an acute angle, in this embodiment of about 72 degrees, with the bend 62a, 63a defining a knee which is acted upon by a respective one of the first and second cam surfaces 51, 52 of the rotor 45 as will be described in detail hereinbelow. The distal ends of the second and third arms 62, 63 each include contact pads 62b, 63b for contacting a respective contact on the printed circuit board 56 for making first and second switches 80a, 80b.

The dose counting unit 42 yet further comprises a battery cell 64 which is disposed in a second cavity 65 in the body part 43. The battery cell 64 is arranged such that the anode and cathode terminals thereof contact respectively the arm 59a of the first conductive member 59 and the first arm 61 of the second conductive member 60.

The dose counting unit 42 still further comprises a window 66, in this embodiment formed of a transparent plastics material, which is fixed to the body part 43, preferably by clipping, so as to protect the electronic display 57 there behind.

Referring to FIG. 3, counting circuitry 102 is illustrated. The circuitry 102 may be integrated on a silicon chip and mounted on the printed circuit board 56. The purpose of the circuitry 102 is to maintain a count of the number of powder doses remaining to be dispensed from the inhaler 3 and to display this count on the electronic LCD 57. The circuitry 102 is programmed to store an initial value which can range from 1 to 199, and decrements this value each time a dose is administered. In the normal state the switches 80a and 80b are open. When a dose is administered, the switch 80a closes while the switch 80b remains open, then the switch 80b closes while the switch 80a remains closed, then the switch 80a opens while the switch 80b remains closed and then the switch 80b opens while the switch 80a remains open. This switching sequence is transduced by the circuitry 102 into the decrement of the count displayed on the LCD 57.

The circuitry 102 has additional functionality. When the count decreases below a predetermined value the circuitry 102 causes the count displayed on the LCD 57 to blink on and off so as to draw the attention of a user to the fact that the inhaler may need to be replaced.

The circuitry 102 has two modes of operation. In the normal mode of operation the circuitry 102 operates as described hereinabove. The other mode of operation is the 'startup mode' which is initiated when the battery cell 64 is placed in the inhaler or when placed within the inhaler the battery cell 64 becomes disconnected and reconnected. In this mode of operation the circuitry 102 enters a 'disabled mode' thereby preventing an incorrect count value being displayed on the LCD 57, unless a control signal is supplied from outside the circuitry 102. If an external control signal is supplied the circuitry 102 initiates a 'test mode'. During the test mode the circuitry 102 supplies a sequence of test signals to the LCD 57 to ensure it is functioning correctly and that all necessary digits can be correctly displayed.

The circuitry 102 has two inputs, a first input signal 101 is supplied from the first switch 80a and a second input signal 103 is supplied from the second switch 80b. When the first switch 80a is closed it connects to ground and the first input signal goes low otherwise the first input signal is high. When the second switch 80b is closed it connects to ground and the second input signal goes low otherwise the second input signal 103 is high. Before a dose is administered the first input signal 101 and the second input signal 103 are high. When a dose is administered the first and second input signals cycle through the sequence of values high, high; low, high; low, low; high, low; and high, high. This sequence is illustrated in FIG. 2a.

The first input signal 101 is supplied to the input of a first input driver 500 and the output signal 105 from the first input driver 500 is supplied to an input SW_A of a switch input detector 600. The second input signal 103 is supplied to the input of a second input driver 500' and the output signal 107 from the second output driver 500' is supplied to the input SW_B of the switch input detector 600. Each of the first and second input drivers receives a pulsed signal 603 from the switch input detector 600. The pulsed signal 603 has a frequency of 1 kHz and each pulse restores and maintains the high values of the first and second input signals 101 and 103 when the first and second switches 80a, 80b are open or opened.

An input driver 500, which is suitable for use as the first or second input driver 500 in the counting circuitry 102, is illustrated in further detail in FIG. 9. The input driver 500 has an input node 502 which receives the first input signal 101. A capacitance 506 exists between the input node 502 and ground. This may be a stray capacitance between the input node and ground or a capacitor connected between node 502 and ground. A p-channel FET 508 has a source connected to a positive voltage Vdd and a drain connected to the input node 502. The input node is also connected to the input of a Schmitt trigger 510 and the output of the Schmitt trigger 510 produces the output signal 105. The gate of the p-channel FET 508 receives the pulsed signal 603 from the switch input detector 600. The form of the pulsed signal 603 is illustrated in FIG. 2b. Generally the pulsed signal 603 is high and is pulsed low at regular intervals with a frequency of 1 kHz. The duration of the pulse is 1.5 to 3 $\mu$s which equates to a duty cycle of approximately $\frac{1}{500}$. When the pulsed signal 603 is high the p-channel transistor 508 is switched off. When the pulsed signal 603 is pulsed low the transistor 508 switches on momentarily and charges the capacitor 506. When the first switch 80a is closed the input node 502 is connected to ground and the capacitor 506 is quickly discharged. The discharging of the capacitor 506 causes the output state of the Schmitt trigger 510 to change state causing the output signal 105 to be asserted high. When the first switch 80a is opened, the capacitor 506 is charged via the transistor 508 and the voltage at the input node 502 rises. The rising voltage when it passes a threshold value causes the output state of the Schmitt trigger 510 to return to a low value. The voltage at the input node 502 is dependent on the current supplied by the transistor 508 and the value of the capacitance 506. By selecting the capacitance 506 the latency between the opening of the switch 80a and the change in the output signal 105 can be controlled. The use of a pulsed signal to operate the p-channel transistor 508 reduces power consumption.

Referring back to FIG. 3, the switch input detector 600 receives two clock signals, the Fdebounce signal 403 and the PullUp signal 401, from a clock generator 400 and the signals 105 and 107. These inputs control the operation of the switch input detector 600 in the normal mode. The switch input detector 600 also receives a reset signal 1301 from reset circuitry 1300 and a pass signal 713 from the start-up circuitry 700. The Fdebounce signal 403 is a regular square wave clock signal with a frequency of around 1 kHz. The PullUp signal 401 is generally high but pulses low with a periodicity of about 1 kHz for a duration of 1.5 to 3 $\mu$s. These signals are effective in the start-up mode. The switch input detector 600 produces the pulsed signal 603 which is supplied to the first and second input drivers 500 and 500' and an output signal 601 which is supplied as an input to the start-up circuitry 700. The pulsed signal 603, in the normal mode, is the same as the PullUp signal 401 supplied by the clock generator 400. The output signal 601 is asserted high when the input signal 105 at the input SW_A and the input signal 107 at the input SW_B follow a predetermined sequence of logic states associated with the administration of a dose. Before a dose is administered both the input signals 105 and 107 are low. On administering a dose, the first input signal 105 pulses high first followed by the second input signal 107 pulsing high, where the high pulses overlap.

The switch input detector 600 is illustrated in further detail in FIG. 10. The PullUp signal 401 and the pass signal 713 are supplied to the two inputs of an AND gate 604, the output of which produces the pulsed signal 603. The PullUp signal 401 is generally high and pulses low. The pass signal 713 is high in the normal mode of operation and low otherwise. The input signal 105 is supplied to first debounce circuitry 602 which also receives as inputs the Fdebounce signal 403 as a clocking signal and the reset signal 1301 as a reset signal and which produces a first debounced signal 105'. The second input signal 107 is supplied to second debounce circuitry 602 which also receives the Fdebounce signal 403 and the reset signal 1301 and which produces a second debounced signal 107'. Each of the first and second debounce circuits 602 allow their output debounced signals 105', 107' to follow a change of state in their input signals 105, 107 only if the new state of the input signal has been maintained for a predetermined time. The first debounced signal 105' and the second debounced signal 107' are supplied as inputs to a quadrature decoder 620. The quadrature decoder 620 also receives the Fdebounce signal 403 as a clock signal and the reset signal 1301. The quadrature decoder 620 is a state machine which responds to first and second debounced signals 105' and 107' cycling through the predetermined sequence corresponding to the dispensing of a dose to assert the output signal 601 high. Otherwise the output signal 601 is low. The state machine responds to the input signals 105' and 107' starting in respective states low, low and cycling through the states high, low; high, high; low, high; and low, low to assert signal 601 high.

An example of a suitable state machine for use as the quadrature decoder 620 is illustrated in FIG. 12. The circuitry includes D flip-flop 622, D flip-flop 630, four-input OR-gate 626, two-input multiplexer 624, XOR gate 632, two-input multiplexer 628, two-input NOR gate 634, inverter 636, four-input NAND gate 638 and inverter 640.

The debounce circuitry is illustrated in further detail in FIG. 11. The signal to be debounced 105 is supplied to the input of a first D flip-flop 606. The non-inverted output of the first flip-flop 606 is supplied as an input to a second D flip-flop 608 and as a first input to a first three-input NAND gate 612. The inverted output of the first flip-flop 606 is supplied to a first input of a second three-input NAND gate 614. The non-inverted output of the second flip-flop 608 is supplied as an input to a third D flip-flop 610 and as a second input to the first three-input NAND gate 612. The inverted output of the second flip-flop 608 is supplied to a second input of the second three-input NAND gate 614. The non-inverted output of the third flip-flop 610 is supplied as a third input to the first three-input NAND gate 612. The inverted output of the third flip-flop 610 is supplied to a third input of the second three-input NAND gate 614. The outputs of the first and second NAND gates 612 and 614 are supplied as inputs to an SR flip-flop 616 the output of which is the debounced signal. Each of the flip-flops is reset by the reset signal 1301 if asserted. Each of the D flip-flops is clocked by the Fdebounce signal 403. Consequently if the input signal 105 has a transition from low to high, for example, and remains high for three clock cycles of the Fdebounce signal 403, then the debounced signal 105' also has a transition from low to high. If the input signal goes low the debounced signal 105' goes or remains low.

The start-up circuitry 700, which is illustrated in further detail in FIG. 13, in normal mode, passes the input signal 601 to the output 'next_dose' as output signal 701. In normal mode the output signal 701 passes through a multiplexer 800 to be received as input signal 801 at the 'count' input of the count and display circuitry 900. In start-up mode the output signal 701 is disabled and the multiplexer 800 provides the first output signal 105 from the first input driver 500 as input signal 801 to the input 'count' of the count and display circuitry 900.

The start-up circuitry 700 is illustrated in more detail in FIG. 13. The start-up circuitry 700 receives: (i) the input signal 601 from the switch input detector 600, (ii) the reset signal 1301 from the reset circuitry 1300, (iii) the Fblink signal 407 (clock signal) from the clock generator 400, (iv) the FextGO signal 409 (clock signal) from the clock generator 400, and (v) a control signal 1201 supplied from an adapted output driver 1200.

The control signal 1201 is produced when the previously mentioned external control signal adapted output driver 1200, as will later be described. When the battery is connected or disconnected and reconnected the circuitry 102 enters the start-up mode. The start-up mode can only be successfully completed and the normal mode entered if the external control signal is applied and the test mode completed. Otherwise, the circuitry enters the disabled mode.

The start-up circuitry 700 has outputs 'passedGON', 'passedGO', 'next-dose', 'AllOff', 'Minus', 'TestMode', 'test0', and 'test1', which produce the outputs signals 715, 713, 701, 705, 703, 707, 709, and 711 respectively.

The output signal 701 is high, during normal mode, when the input signal 601 is high, that is, when a dose has been administered. The output signal 701 is supplied as an input to multiplexer 800.

The output signals 713 and 715 are respectively high and low both during the normal mode and during the test mode. The output signals 713 and 715 are otherwise, that is, during the disabled mode, respectively low and high. The pass signal 713 is supplied as an input to the switch input detector 600 and as a control signal to the multiplexer 713. The multiplexer receives as inputs the signals 105 and 107 and produces a signal 801. When pass signal 713 is asserted high the signal 701 is provided as the signal 801 otherwise signal 105 is provided.

The output signal 705 turns off the LCD during the disabled mode. In this mode it is asserted high. This signal is supplied to count and display circuitry 900.

The output signals 703, 707, 709 and 711 are used during the test mode and will be described in relation to that mode hereinafter. These signals are supplied as inputs to the count and display circuitry 900.

Referring to FIG. 13, in the start-up circuitry 700 the reset signal 1301 and the control signal 1201 are supplied as inputs to a two-input AND gate 790, the output of which is supplied as a reset signal to first, second and third D flip-flops 792, 794 and 796. The FextGO signal 409 is supplied as the clock input to each of the D flip-flops 792, 794 and 796. The input of the first flip-flop 792 is connected to a high voltage, the output of the first flip-flop is connected to the input of the second flip-flop 794 the output of the second flip-flop 794 is connected to the input of the third flip-flop 796 and the inverted output of the third flip-flop 796 is connected to the Set(S) input of a SR flip-flop 798. The reset(R) input of the SR flip-flop 798 receives the reset signal 1301. The non-inverting output of the SR flip-flop 798 produces pass signal 713 and the inverting output produces signal 715. The reset signal 1301 is an active low signal. The control signal 1201 is a logic high, otherwise the node receives a 30 Hz clock signal. The FextGO signal 409 is a 4 Hz clock signal 409. Whenever the reset signal 1301 is active, that is, low, the output signal 713 becomes low and the output signal 715 becomes high. When the reset signal 1301 is high the SR flip-flop 798 is controlled by the flip-flop 796. In the presence of the control signal 1201 and the absence of the reset signal 1301, the S input to the SR flip-flop 798 goes low after two to three clock cycles of the FextGO signal 409 and latches the pass signal 713 high and signal 715 low. In the absence of the control signal 1201, that is, when the 30 Hz clock signal is present and when the reset signal 1301 is absent, that is, node 1301 is high, the flip-flops 792, 794 and 796 are reset every 1/30 th of a second by AND gate 790. In this case, the high input of the flip-flop 792 is not transferred via flip-flops 792, 794, 796 to SR flip-flop 798. Hence, pass signal 713 remains low and signal 715 remains high.

The input signal 601 is input to register 720. The register 720 also receives as an input the pass signal 713 and an address signal 751 comprising first, second, third, fourth and fifth bit signals 733, 735, 737, 739 and 741. The register 720 outputs first, second, third, fourth and fifth address bit signals 721, 723, 725, 727, 729 and their complements 721', 723', 725', 727' and 729'. The register 720 is illustrated in further detail in FIG. 14. Each of the first, second, third, fourth and fifth bit signals 733, 735, 737, 739 and 741 is supplied to a respective first 722, second 724, third 726, fourth 728 and fifth 730 D flip-flops to produce the first, second, third, fourth and fifth address bit signals 721, 723, 725, 727 and 729 from their respective non-inverting outputs and the inverted address bit signals 721 ', 723', 725', 727' and 729' from their inverting outputs. The flip-flops 722, 724, 726, 728 and 730 are each clocked by the input signal 601, that is, every time a dose is administered. The flip-flops 722, 724, 726, 728 and 730 are each reset by the inverse of the pass signal 713.

The address bit signals are used to access the ROM 731 which is illustrated in more detail in FIG. 15. A particular address defined by the address bit input signals 721, 723, 725, 727 and 729 and their inverse signals 721', 723', 725', 727' and 729' is used to simultaneously access and read from a row of ten memory cells. The signals 721, 723, 725, 727 and 729 and 721', 723', 725', 727' and 729' are supplied to a decoder 732 which controls the access of one row in the ROM 731 at a time. The ten bit output from the addressed row of memory cells is the ten output signals from the ROM 731. The ROM 731 is illustrated in more detail in FIG. 15 and the cells of the ROM 731 are illustrated in FIGS. 16 and 17. The ROM 731 and cells are conventional.

The first output signal 733 from the ROM 731 indicates whether the counting circuitry is in the disabled mode or not. If the disabled mode is active the signal 733 is low. If the normal mode is active the signal 733 is high.

The second output signal 753 from the ROM 731 is used to control the LCD by making a flashing minus sign appear. This signal is AND-ed in AND gate 704 with the Fblink signal 407 to produce the output signal 703. The second output signal 753 is also OR-ed with the inverted pass signal 715 in OR gate 706 to produce the signal 705. The inverted pass signal 715 is high in the disabled mode and low otherwise.

The third output signal 707 is used to define whether a test mode is in progress.

The fourth and fifth signals 709 and 711 control the operation of test modes.

The remaining output signals 733, 735, 727, 739 and 741 make up the address signal 751 supplied to register 720. The address signal 751 gives the address of the next row in the ROM 731 which should be read when the input signal 601 is asserted. Such assertion occurs in the test mode to allow the test procedure to be moved through, and in the normal mode, when a dose is administered.

Referring back to FIG. 3, the multiplexer 800 receives the first output signal 105 from the first input driver 500 as a first input and the output signal 701 from the 'next_dose' output of the start-up circuitry 700 as a second input. The output signal 801 from the multiplexer 800 is supplied to the 'count' input of the count and display circuitry 900. The multiplexer 800 receives the pass signal 713 as its control signal. When the pass signal 713 is low the first input of the multiplexer 800 is coupled to its output, whereas when the pass signal 713 is high the second input of the multiplexer is coupled to its output.

The count and display circuitry 900 is illustrated in more detail in FIGS. 18 to 28. Referring to FIG. 18, the count and display circuitry has a counter 810 (illustrated in more detail in FIG. 19 and FIGS. 27 and 28), decision circuitry 860 (illustrated in more detail in FIG. 20), least significant decimal figure decoder 830 (illustrated in more detail in FIG. 21), second least significant decimal figure decoder 840 (structurally the same as decoder 830), most significant decimal figure decoder 850 (illustrated in more detail in FIG. 22) and LCD driver 910 (illustrated in more detail in FIGS. 23, 24, 25 and 26).

The count and display circuitry 900 receives the input signals 801 from multiplexer 800, signal 107 from the second input driver 500, the reset signal 1301 from reset circuitry 1300, the negated pass signal 715 from the start-up circuitry 700, the Fblink signal 407 from the clock generator 400, the Flcd signal 405 from the clock generator 400, the signal 705 (asserted in the disable mode for deactivating the screen),and the signals 703, 707, 709 and 711 (associated with the test mode).

The count and display circuitry 900 produces: first LCD backplane control signals 911, 913 and 915 which are input into a first LCD backplane driver 1000 to produce signal 1001 for switching a first LCD backplane on or off; second LCD backplane control signals 917, 919 and 921 which are input into a second LCD backplane driver 1000 to produce signal 1003 for switching a second backplane of the LCD on or off; and segment control signals Seg_2ec, Seg_3d_, Seg_3ec, Seg_3ab, Seg_3fg, Seg_2ab, Seg_2fg and Seg_2d 1bc which are input to output drivers to produce respective signals for controlling the figures displayed on the LCD. A segment control signal Seg_Nxy can cause the activation of both, none or either one of the LCD segments Nx and Ny depending upon whether the signals 1001 and 1003 are both high, both low or either one high with the other being low. Consequently the signals 1001 and 1003 and the segment control signals can selectively activate anyone of the segments illustrated in FIG. 34. Referring to FIG. 34, the most significant figure of the displayed count is a 1 displayed when the elements 1a and 1b are activated. The least significant figure of the displayed count can be 0, 1, 2, 3, 4, 5, 6, 7, 8 or 9 and is displayed when combinations of the elements 3a, 3b, 3c, 3d, 3e, 3f and 3g are activated. The second least significant figure of the displayed count can be 0, 1, 2, 3, 4, 5, 6, 7, 8 or 9 and is displayed when combinations of the elements 2a, 2b, 2c, 2d, 2e, 2f and 2g are activated.

The counter 810 receives the input signal 801 at its 'clock' input, the input signal 107 at its 'ShiftIn' input, the inverse pass signal 715 at its 'NornN/shift' input and the reset signal at its reset input. In this particular implementation each time the signal 801 is asserted in the normal mode, the counter decrements the count stored within it by one. In the normal mode this occurs each time a dose is dispensed. The counter can decrement from 199 to zero and the count will be displayed on the LCD.

The binary outputs 811, 813, 815 and 817 of the counter 810 define the value of the least significant decimal figure of the count displayed. The binary outputs 819, 821, 823 and 825 of the counter 810 define the value of second least significant decimal figure of the count displayed. The binary output 827 from the counter 810 defines the value of the most significant decimal figure of the count displayed.

The signals 811, 813, 815 and 817 are supplied as inputs to a least significant figure decoder 830. This decoder decodes the value of the least significant decimal figure represented by the signals 811, 813, 815 and 817 and produces output signal 831 comprising binary signals s3a, s3b, s3c, s3d, s3e, s3f, s3e, s3f and s3g which define which of the respective elements 3a, 3b, 3c, 3d, 3e, 3f, and 3g of the LCD should be activated to display the value of the least significant decimal figure of the count. An example of a suitable decoder is illustrated in FIG. 21.

The signals 819, 821, 823 and 825 are supplied as inputs to a second least significant figure decoder 840. This decoder decodes the value of the second least significant decimal figure represented by the signals 819, 821, 823 and 825 and produces output signal 841 comprising binary signals s2a, s2b, s2c, s2d, s2e, s2f, s2e, s2f and s2g which define which of the respective elements 2a, 2b, 2c, 2d, 2e, 2f, and 2g of the LCD should be activated to display the value of the least significant decimal figure of the count. An example of a suitable decoder is illustrated in FIG. 21.

The signal 827 is supplied as an input to the most significant figure decoder 850 which produces an output signal s1bc which causes either both elements 1b and 1c to be activated or both elements 1b and 1c to be deactivated. An example of a suitable decoder is illustrated in FIG. 22.

FIG. 19 illustrates the counter 810 in more detail. The counter has a first shift register/decrementor 820, a second shift register/decrementor 840, a third shift register/decrementor 860 and a NAND gate 870. In the normal mode when signal 715 is low the first shift register/decrementor 820, the second shift register/decrementor 840 and the third incrementor/decrementor function as decrementors. In the start up mode they are controlled by the signal 715 to function as shift registers. The first decrementor 820 stores the value of the least significant decimal figure of the count. It decrements this value in response to the signal 801 indicating a dose has been dispensed and produces signals 811, 813, 815 and 817. The second decrementor 840 stores the value of the second least significant decimal figure of the count. It decrements this value in response to the signal 801 indicating a dose has been dispensed and a signal 841 from the first decrementor and produces signals 819, 821, 823 and 825. The third decrementor stores a value of the most significant decimal figure of the count. It decrements this value in response to the signal 801 indicating a dose has been dispensed and a signal 843 from the second decrementor. The NAND gate 870 receives high signals 845, 847 and 849 from the first, second and third decrementors 820, 840 and 860 when the respective decrementors reach zero. The output of the NAND gate is supplied to the first decrementor 820 and disables the first decrementor when the count reaches 000. In the test mode the shift register/decrementors act as shift registers and the signal 107 and signal 801 (105) are used to set the initial value of the count to be decremented. A suitable shift register/decrementor for use as the first decrementor 820 or second decrementor 840 is illustrated in FIG. 27. A suitable shift register/decrementor for use as the third decrementor 860 is illustrated in FIG. 28.

Referring back to FIG. 18, the outputs from the counter 810 are also input to decision circuitry 860 which determines when the count is less than or equal to 20. When this occurs the signal output from the decision circuitry is asserted high. This signal is supplied to gate 902 where it NAND-ed with the Fblink signal 407, inverted by the inverter 904 and is then supplied as input signal 905 to each of the decoders 830, 840 and 850 to intermittently disable them causing the value displayed on the LCD to blink. Suitable decision circuitry 860 is illustrated in FIG. 20.

The signal 705 when asserted for example in the disable mode is supplied as signal 905 to the decoders 830, 840 and 850. This signal disables the decoders and prevents the LCD being driven.

Each of the respective output signals 831, 841 and 851 from the decoders 830, 840 and 850 are supplied to the LCD driver 910. The LCD driver converts the inputs 831, 841 and 851 into output signals 911, 913, 915 and 917, 918, 919 and Seg_2ec, Seg_3d, Seg_3ec, Seg_3ab, Seg 3fg, Seg_2ab, S_2fg and S_2d 1bc. These output signals are suitable for driving an LCD display in a multiplexed fashion to display any number between 0 and 199. As previously explained by varying the configuration of the output levels of the signals 911, 913, and 915; 917, 918 and 919; and S_2ec, Seg_3d, Seg_3ec, Seg_3ab, Seg_3fg, Seg_2ab, Seg_2fg and S_2d 1bc an LCD can be driven to display any one of the numbers between 0 and 199, and will be driven in the normal mode to display the value of count.

The LCD driver 910 is illustrated in more detail in FIG. 23. The LCD is made up of four similar circuit block 960 and a wave generator 970. The wave generator 970 generates the actual voltage wave forms which are modulated by the signals: s2e and s2c, s3d in a first circuit block 960; s3e and s3c, s3a and s3b in a second circuit block 960; s3f and s3g, s2a and s2b in a third circuit block 960; and s2f and s2g and s1bc and s2d in a fourth circuit block 960; to produce the respective output signals Seg_2ec, Seg_3d from the first circuit block 960; Seg_3ec, Seg_3ab from the second circuit block 960; Seg_3fg, Seg_2ab from the third circuit block 960; and Seg_2fg and S_2d 1bc from the fourth circuit block 960. Circuitry suitable for use as the LCD wave generator is illustrated in FIG. 26. Referring to FIG. 23, each circuit block 960 receives as inputs the signals 707, 709 and 711 and the signals 971, 973, 975 and 977 from the wave generator 970. Referring to the particular circuit block 960' labelled in FIG. 23 the signals s2e and s2c are passed through the switch 928 and input as controls to a multiplexer 912 which receives the signals 971, 973, 975 and 977. The signal output from the multiplexer 912 is the output signal Seg_2ec. The signals 709 and 711 and 707 are also input to the switch 928. The signal 707 controls the operation of the switch 928. In the test mode the input signals 709 and 711 replace respectively the signals s2e and s2c as control signals for the multiplexer 928. The switch 928 is illustrated in more detail in FIG. 25. The output from the multiplexer 912 is inverted in an inverter 944 and input into a multiplexer 950 which receives as a control signal the input signal 707. In the test mode the multiplexer 950 passes this inverted signal as the output signal Seg_3d The multiplexer 950 receives as its other input an output signal from a multiplexer 914. The multiplexer 914 receives the signals 971, 973, 975 and 977 as inputs and the signal s3d as a control input. The multiplexers 912 and 914 are identical and illustrated in more detail in FIG. 24.

It should be appreciated that in the normal mode each of the four circuit block 960 in the LCD driver 910 is generally controlled by two pairs of input signals. The first pair relating to two LCD elements, for example, w and x and the second pair relating to two different elements, for example, y and z. In the normal mode each circuitry block 960 selects one of the signals 971, 973, 975 and 977 in response to which one of the four possible combinations of the values of the first pair of input signals is received to activate both, none or either one of the elements w and x and selects one of the input signals 971, 973, 975 and 977 in response which one of the four possible combinations of the values of the second pair of input signals is received, to activate both, none or either one of the elements y and z. In the test mode each of the four circuit blocks is controlled by the pair of test signals 707 and 709 and the two output signals from each block are the inverse of each other. In the test mode the circuitry selects one of the signals 971, 973, 975 and 977 in response to the four possible combinations of the values of the input signals 709 and 707 to activate the elements w and x while not activating the elements y and z, to activate the element w but not the element x while not activating the y and activating the element z, to not activate the element w but to activate the element x while activating the element y and not activating the element z, or to activate neither element x and w while activating both elements y and z. The four groups of elements in the LCD driver are: 2e and 2c, 3d for the first circuit block 960; 3e and 3c, 3b and 3a for the second circuit block; 3f and 3g, 2b and 2a for the third circuit block; and 2f and 2g, 1bc and 2d for the fourth circuit block. Each group is associated with one of the circuit blocks 960. In the test mode, the ROM 731 controls the test procedure. FIG. 35 illustrates the four phases of the test procedure. Each of the phases corresponds to one of the four possible combinations of the values of the input signals 709 and 711. In FIG. 35 a segment is defined as activated unless there is a bar above it. The procedure tests all four combinations of each segment pair (one combination in each phase) and tests all of the segment pairs in each phase. A camera and computer could be used to monitor the LCD during the test procedure to ensure that the expected activation sequence of segments was followed. If it was not the LCD is defective. The output signals 911 to 915 from the count and display circuitry 900 are supplied to an LCD back plane driver 1000 to produce a signal for driving the first back plane. Signals 917 to 921 output from the count and display circuitry 900 are also supplied to an LCD back plane driver 1000 to produce an output signal 1003 for driving a second LCD back plane. A suitable backplane driver 1000 is illustrated in FIG. 29.

Each of the segment control signals (excluding signal Seg_3ab) output from the count and display circuitry 900 is supplied to an output driver 1100 to produce signals for driving the LCD display. The signal Seg_3ab is provided to an output driver 1200. A circuit suitable for use as an output driver 1100 is illustrated in FIG. 30. A circuit suitable for use as the output driver 1200 is illustrated in FIG. 31. The output driver 1200 operates in the same manner as the output driver 1000 but has additional functionality which is used during start-up of the device. During start-up unless a control signal 1203 is applied to the node 1202 of the output driver 1200 the counting circuitry will enter a disabled mode. The application of a control signal to the node 1202 brings it to ground, causing the control signal 1201 to go high and the counting circuitry to enter a test mode. On completion of the test mode the counting circuitry enters the normal mode. The control signal 1203 is applied externally to the PCB 56 in FIG. 1 and cannot accidentally be supplied by an unskilled user.

Referring to FIG. 3, an oscillator 200 provides an output signal 201 having a form illustrated in FIG. 2c. The oscillator 200 is illustrated in more detail in FIG. 4. The oscillator 200 has a reference voltage source 210 connected between a first input 212 at a positive voltage Vdd and a second input 214 which is grounded. The voltage source 210 produces a bias output signal 211 and a reference output signal 213. The bias output signal 211 is connected to the gate of a p-channel field effect transistor 270 which has its source connected to a positive voltage Vdd and its drain connected to a node 202. The reference output signal 213 is supplied as an input to both a non-inverting input 236 and a first bias input 238 of an operational amplifier 230. The operational amplifier 230 is connected between a positive voltage Vdd and ground by respective terminals 232 and 234. The output signal 201 of the operational amplifier 230 is provided to the gate of an n-channel field effect transistor 280 and as the output of the oscillator. The field effect transistor 280 has its drain connected to the node 202 and has its source connected to ground. The node 202 is connected to an inverting input 240 and a second bias input 242 of the operational amplifier 230 and supplies signal 231 thereto. The node 202 is connected via a capacitor 290 to ground.

The operational amplifier 230 in combination with the capacitor 290 operates as a oscillator producing an output signal 201 as illustrated in FIG. 2c. The period of the oscillating signal 201 is determined by the value of the capacitor 290.

The bias output signal 211 (Vp) has a determined relationship to the reference output signal 213 (Vref) for a particular supply voltage (Vdd) applied across the first and second inputs 212, 214 of the reference voltage source 210 as illustrated in FIG. 2d. This FIG. illustrates how the outputs from the reference voltage source 210 varies with applied battery voltage Vdd. The value of Vdd in use is ~1V. At this value reference signal 213 (Vref) is constant at 680 mV. Referring to FIG. 2d it can be seen that above an applied voltage Vdd of approximately 1 V the voltage at terminal 212 (Vdd) minus the bias voltage signal 211 (Vp) is a constant, that is Vdd–Vp=1020 mV, and that the reference voltage signal 213 (Vref) minus the voltage at terminal 214 (earth) is a constant, that is, Vref is a 1020 mV value above ground. Consequently the bias voltage signal 211 supplies a constant voltage with respect to Vdd and the reference voltage signal supplies a constant voltage with respect to ground. The transistor 270 is controlled by bias signal 211 and acts as a constant low current (~10 nA) source. This low current charges the capacitor 290. The voltage developed across the capacitor, the signal 231, is illustrated in FIG. 2c. When the voltage across the capacitor increases above the value Vref of the reference signal 213, output signal 201 of the operational amplifier 230 increases very quickly. This signal switches on transistor 280 which rapidly discharges the capacitor, rapidly decreasing the voltage across the capacitor 290 and causing the output signal 201 of the oscillator to return to zero, and switching off the transistor 280. The current source 270 continues to charge the capacitor 290 and the voltage at node 202 rises again. The constant current source transistor 270 is smaller than, that is, has a smaller channel width to channel length ratio than, the transistor 280.

Referring to FIG. 5, the voltage reference source 210 is illustrated in further detail. The circuit has: a p-channel field effect transistor 216 whose source is connected to a positive voltage Vdd at the input node 212 and whose drain is connected to a first output node 215 which produces the output reference signal 213; an n-channel field effect transistor 220 whose drain is connected to the first output node 215 and whose source is connected to ground at the input node 214; another p-channel field effect transistor 218 whose source is connected to a positive voltage at the input node 212 and whose drain is connected to a second output node 217 which supplies the bias signal 211; and another n-channel field effect transistor 222 whose drain is connected to the second output node 217 and whose source is connected in series with a resistor 226 to ground at the input node 214. The gates of the p-channel transistors 216 and 218 are interconnected and in addition are connected to the second output node 217. The gates of the n-channel transistors 220 and 222 are interconnected and in addition are connected to the first output node 215. The output node 215 and output node 217 are interconnected via a capacitor 224.

The p-channel transistors 216 and 218 are identical and form part of a symmetric current mirror. The transistors 216 and 218 have channel widths of 10 μm and channel lengths of 50 μm. The n-channel transistors 220 and 222 are not identical and with the resistor 226 form part of an asymmetric non-linear current mirror. The transistor 222 is larger than the transistor 220, that is, it has a larger channel width to channel length radio. The transistor 222 in this embodiment has a width of 50 μm and a length of 5 μm whereas the transistor 220 has a width of 50 μm and a width of 10 μm. The operating characteristics of the current mirrors are illustrated in FIG. 2e. Curve A is associated with the non-linear current mirror. Curve B is associated with the linear current mirror. There are two stable operating points X and Y. The capacitor 224 is used to ensure that the point Y is the actual operating point as opposed to the point X. The output signals 213 and 211 are illustrated in FIG. 2d. It will be appreciated that for an applied voltage Vdd of greater than about 1 V the output voltage signals 213 is independent of fluctuations in the voltage supply. The value of the resistance 226 and the characteristics of the transistors 220 and 222 determine the shape of curve A in FIG. 2e. The value of the resistance 226 is chosen so that the operating point X is correctly located. Thermal characteristics of the resistor are chosen such that they compensate for the change in the operating characteristics of the transistors 220 and 222 with a change in temperature. This allows the characteristics of the non-linear current mirror to remain stable with temperature and for the operating point X in FIG. 2d to remain stable with temperature. Consequently, the resistor 226 allows the voltage reference 210 to produce reference voltages which are substantially independent of the applied voltage Vdd and substantially independent of the ambient temperature. The resistor 226 is composed of a resistor 228a connected in series with a resistor 228b. The resistor 228a has a positive temperature coefficient and the resistor 228b has a negative temperature coefficient. The combination of positive and negative temperature coefficients of the resistors 228a and 228b results in the combined resistance 226 having a chosen temperature coefficient and chosen resistance. According to one example, the resistor 228a may be formed from n-doped silicon having a resistance of 821 kOhms and a temperature coefficient of 6.7 mV/K, the resistor 228b is formed from polysilicon and has a temperature coefficient of −1.7 mV/K and a value of 179 kOhms. This results in the resistance 226 having a value of 1 MOhm with a temperature coefficient of 5.2 mV/K. The resistor 226 has a temperature coefficient which is intermediate of the two resistors 228a and 228b. The characteristics of the resistor 226 is varied by adding different component resistors in series. In this manner a desired temperature coefficient can be obtained. Alternatively, the resistor 226 can have a designed temperature coefficient which compensates for variations in the operation of the transistor 270 (FIG. 4) and/or the operational amplifier 230 (FIG. 4) and/or the transistors 216, 218, 220 and 226 of the reference voltage source 210 (FIG. 5) with temperature. Consequently, the oscillator 200 may have operational characteristics substantially independent of temperature variations.

The output node 215 produces the reference signal 213 and the output node 217 produces the bias signal 211 illustrated in FIG. 2e. The combination of the resistors 228a and 228b allows the resistance 226 to be engineered to have a temperature coefficient which compensates for any variation in operation, caused by a change in temperature.

Referring to FIG. 6, the operational amplifier 230 is described in further detail. A differential amplifier 241 is connected between a positive voltage Vdd at terminal 232, through an active bias 250 to earth at terminal 234. The differential amplifier 241 has a first input 236 and a second input 240. The first input 236 receives the reference signal 213 illustrated in FIG. 2d. The second input receives the signal 231 developed across capacitor 290, illustrated in FIG. 2c. The differential amplifier has an output node 245. The active bias 250 has a first bias input 238 and a second bias input 242. The first bias input 238 receives the reference signal 213 and the second bias input 242 receives the signal 231. The output of the differential amplifier 241 is passed through an amplifier 260 having a p-channel transistor 262 with a gate connected to the output node connected in series via an output node 266 with an n-channel transistor 264 whose gate is connected to the first bias input 238. The output of the amplifier 260 passes through inverting amplifier 266 and inverting amplifier 268 to produce the output signal 201 of the operational amplifier 230. Each of the inverting amplifiers 266, 267 comprises a p-channel transistor 268 and an n-channel transistor 269.

The differential amplifier 241 has: a first p-channel transistor 242 with its source connected to the positive voltage Vdd at the terminal 232 and its drain connected to an intermediate node 243, a first n-channel field effect transistor 246 with its source connected to the intermediate node 243 and its drain connected to a node 247, a second p-channel field effect transistor 244 with its source connected to the positive voltage Vdd at the terminal 232 and its drain connected to an output node 245, and a second n-channel field effect transistor 248 with its drain connected to the output node 245 and its source connected to the node 247. The gates of the p-channel transistors 242 and 244 are interconnected and in addition connected to the intermediate node 243. The gate of the first n-channel transistor 246 is connected to the first input 236 of the operational amplifier 230 and receives the reference signal 213. The gate of the second n-channel field effect transistor 248 is connected to the second input 240 of the operational amplifier 230 and receives the signal 231 developed across capacitor 290. The node 247 is connected to the active load 250.

The p-channel transistors 242 and 244 have channel widths of 1 μm and channel lengths of 1 μm. The n-channel transistors 246 and 248 have channel widths of 10 μm and channel lengths of 1 μm. The first p-channel transistor 242 and the second p-channel transistor 244 form a current mirror. The first n-channel transistor 246 and the second n-channel transistor 248 from the input stage of the differential amplifier 241. The first p-channel transistor 242 loads the first n-channel transistor. The second p-channel transistor 244 loads the second n-channel transistor.

The active bias 250 has: a first n-channel transistor 252 connected between the node 247 and the earth 234 and a second n-channel transistor 254 connected between the node 247 and the earth 234. The gate of the first n-channel transistor 252 is connected to the first bias input 238 and receives the reference signal 213. The gate of the n-channel transistor 254 is connected to the second bias input 242 and receives the signal 231 developed across the capacitor 290. The signal 231 is illustrated in FIG. 2c. The signal 213 is illustrated in FIG. 2d and is a constant reference level of 680 mV. The transistor 252 acts as a constant current source and is always on. The transistor 254 is normally not fully switched on. However, when the signal 231 reaches a value greater than the reference signal 213, that is, 680 mV, the transistor 254 turns fully on allowing node 245 to be quickly pulled to a low voltage and allowing the output signal 201 to go high. The increase in the output signal 201 causes the signal 231, via transistor 280, to decrease. The operational amplifier 230 acts as a comparator. The operational amplifier 230 only draws appreciable current while the output signal 201 pulses high for a few microseconds. The amplifier therefore uses little power while providing a fast switching speed. The n-channel transistor 252 has a channel length of 2 μm and a channel length of 5 μm. The n-channel transistor 254 has a channel length of 0.6 μm and a channel width of 10 μm.

Referring back to FIG. 3, a voltage booster 300 is connected to the output of the oscillator 201 and produces at its output 301 a boosted voltage V30 of approximately 3.0 V. The voltage booster 300 is illustrated in more detail in FIG. 7. Referring to FIG. 7 the voltage booster 300 has logic circuitry 310 for converting the input clock signal 201 into output signals 311, 313, 315 and 317. Signals 311 and 313 are synchronous clock signals. Signals 315 and 317 are synchronous clock signals in anti-phase to the signals 311 and 313. The frequency of the clock signals 311 to 317 is the same as the input clock signal 201. The circuitry 310 ensures that the signals 315 and 317 do not overlap the signals 311 and 313. A p-channel field effect transistor 322 is connected as a switch between a positive voltage supply and a first plate 341 of a capacitor 340. The gate of the p-channel transistor 322 receives the output signal 313. The first plate 341 of the capacitor 340 is also connected to ground via an n-channel transistor 330 which operates as a switch. The gate of the n-channel transistor 330 is connected to the signal 317. A second plate 342 of the capacitor 340 is connected to a positive voltage Vdd via a p-channel transistor 332 which operates as a switch. The gate of the p-channel transistor 332 is connected to the signal 315. The second plate of the capacitor 342 is also connected to an output node 360 of the voltage booster 300 via a p-channel transistor 320 which acts as a switch. The gate of the p-channel transistor 320 is connected to the signal 311. The output node 360 of the booster circuit 300 is connected via a capacitor 350 to ground. The output node 360 provides the output signal 301. In the first phase of operation, the transistors 332 and 330 are switched on via the synchronous signals 315 and 317. The transistors 322 and 320 are simultaneously switched off by the synchronous signals 311 and 313. During this phase of operation the second plate 342 of the capacitor 340 is charged to a positive potential relative to the first plate 341. During a second phase of operation, the transistors 332 and 330 are switched off by the synchronous signals 315 and 317 and the transistors 322 and 320 are simultaneously switched on by the synchronous signals 311 and 313. In this phase of operation the first plate 341 of the capacitor 340 is raised to approximately the voltage Vdd which raises the voltage at the second plate 342 of the capacitor 340 to approximately twice the voltage Vdd. The transistor 320 allows the thus boosted voltage at the second plate of the capacitor 340 to be presented at the output node 360 as the output signal 301 from the booster circuit 300. The output signal 301 simultaneously charges the capacitor 350. When this phase of operation finishes and the first phase again begins the transistor 320 is switched off isolating the capacitor 350 which has been charged to the boosted voltage value. The boosted voltage value V30 is therefore continuously presented at the output node 360.

The capacitor 340 is illustrated in more detail in FIGS. 33a, 33b, 33c and 33d. A conventional capacitor is illustrated in FIG. 33a and its equivalent circuit diagram in FIG. 33b. The capacitor is formed over a p-doped silicon substrate 2000. A dielectric layer 2040 separates the first plate of the capacitor 341, formed from a layer of polysilicon 2010, from the substrate 2000. A thin dielectric layer 2020 separates the second capacitor plate 342, formed from a second polysilicon layer 2030, from the first polysilicon layer 2010. As illustrated in FIG. 33b a parasitic capacitor 2002 having a value Cp is formed between the first plate of the capacitor and the grounded silicon substrate 2000. During the operation of the booster circuit 300 this parasitic capacitance may result in power loss.

The capacitor illustrated in FIG. 33c is devised to reduce power loss and finds particular application in the booster circuit 300 as capacitor 340. Referring to FIG. 33c, the capacitor structure differs from FIG. 33a in that an n-type well 2100 is formed in the p-substrate 2000. The layers 2040, 2010, 2020 and 2030 are formed over the well 2100. These layers do not extend beyond the dimensions of the well in this example. The n-type well forms a reverse biased pn junction diode with the p-type substrate. Such a diode has a low capacitance. FIG. 33d illustrates a schematic equivalent circuit of the structure illustrated in FIG. 33c. The diode forms a small capacitor 2004 with small capacitance Cd in series with the parasitic capacitor 2002' having a capacitance Cp, formed between the first plate 341 and the n-type well 2100. The combined capacitance of the capacitors 2002' and 2004 is less than Cd and less than Cp.

Referring to FIG. 3, the output signal 201 from the oscillator 200 is supplied as an input to the clock generator 400 which is illustrated in more detail in FIG. 8. The clock generator 400 produces PullUp signal 401, Fdebounce signal 403, Flcd signal 405, Fblink signal 407 and FextGO signal 409. The input signal 201 is illustrated in FIG. 2c. The PullUp signal 401 and the Fdebounce signal 403 have a frequency of approximately 1 kHz.

However, the pull-up signal 401 is a pulsed signal being generally high but pulsed low for a few microseconds in each period whereas the FDEBOUNCE signal 403 is a regular symmetric signal being high 50% of the time and low 50% of the time. The Flcd signal 405 has a frequency of 138 Hz and is a regular symmetric square wave clock signal. The output signal FextGO 409 has a frequency of 4 Hz and is a regular symmetric square wave clock signal. The output signal Fblink 407 has a frequency of 0.5 Hz and is a regular symmetric square wave clock signal.

The pulsed PullUp signal 401 is supplied to the switch input detector 600 and is used to control the pulsed signal 603 output from the switch input detector 600 and supplied to the first and second input drivers 500. The Fdebounce signal 403 is also supplied to the switch input detector 600 and is used to control the sampling of the signals provided at the inputs SW_A and SW_B of the switch input detector 600. The Flcd signal 405 is supplied to the LCD driver 910 within the count and display circuitry 900 and is used to control the multiplexing of the signals which control the output on the LCD. The FextGO signal 409 is used to control a mode of operation when the counting device is initially switched on. The Fblink signal 407 is supplied to the start-up circuitry 700 and the count and display circuitry 900 and is used to cause the image display on the LCD screen to flash with the frequency 0.5 Hz.

Referring to FIG. 8, the clock generator 400 has an inverter 410 for inverting the input signal 201 to produce the inverted signal 411. The inverted signal 411 is then supplied to the first one of a linear series of sixteen frequency dividers 420. The output of each frequency divider toggles on a rising edge at its input. Each frequency divider receives a clock signal and produces a regular square wave clock signal, with half the frequency of the input signal which is supplied as an input to the next frequency divider in the linear series. The Fblink signal 407 is taken from the output of the sixteenth frequency divider 420. The FextGO signal 409 is taken from the output of the thirteenth frequency divider 420. The Flcd signal 405 is taken from the output of the eighth frequency divider 420. The Fdebounce signal 403 is taken from the output of the fifth frequency divider. The inverted signal 411, the output of the first frequency divider 420 and the output of the second frequency divider are combined in a NOR gate 430 to produce the signal 413. The output from the third, fourth and fifth frequency dividers 420 are each supplied to the input of a NOR gate 430 to produce the signal 415. The signals 413 and 415 are input to a NAND gate 432 to produce the PullUp signal 401.

Referring back to FIG. 3, the reset circuit 1300 is illustrated in more detail in FIG. 32. The battery is connected to two terminals. The positive terminal connects to a resistor 1306, the negative terminal connects to a capacitor 1308. The capacitor 1308 and resistor 1306 are connected in series through a node 1302. When the battery is connected the voltage at the node 1302 increases. The voltage at the node 1302 is supplied as an input to a Schmitt trigger latch 1304. The output of the Schmitt trigger latch is supplied to an inverter which produces the reset signal 1301. As the voltage at the node 1302 increases the reset signal 1301 rises from zero and is latched high. The capacitor 1300 has a value of 10 pF.

Finally, it will be understood that that the present invention has been described in its preferred embodiment and can be modified in many different ways within the scope of the appended claims.

What is claimed is:

1. A counting device, comprising:
   an input for receiving an input signal having at least three distinct input states;
   a memory for storing a count; and
   circuitry connected to receive said input signal and responsive to a predetermined sequence of input states of said input signal to increment or decrement said count, wherein said predetermined sequence includes the at least three input states.

2. A counting device as claimed in claim 1, wherein said input signal comprises first and second component signals, wherein each signal has first and second distinct states.

3. A counting device as claimed in claim 2, wherein said predetermined sequence of input states comprises: the first and second component signals in the first state; the first component signal in the second state with the second component signal in the first states; the first and second component signals in the second state; and the first component signal in the first state with the second component signal in the second state.

4. A counting device as claimed in claim 1, wherein said circuitry comprises a state machine responsive to the predetermined sequence.

5. A counting device as claimed in claim 1, wherein said memory comprises a BCD counter.

6. A counting device as claimed in claim 1, further comprising display drive means for displaying the value of the count.

7. A counting device as claimed in claim 5, in combination with a display driven by a drive means.

8. A counting device as claimed in claim 6, wherein said display is an LCD display and the device further comprises display control means for controlling the display drive means to activate each of the elements of the LCD display.

9. An integrated circuit comprising a device as claimed in claim 1.

10. An inhaler including a device as claimed in claim 1.

11. A powder inhaler for administering powder by inhalation including a device as claimed in claim 1.

12. A counting device, comprising:
    an input for receiving an input signal having at least three distinct input states;
    a memory for storing a count; and
    circuitry connected to receive said input signal and responsive to a predetermined sequence of input states of said input signal to vary said count, wherein said predetermined sequence includes the at least three input states, wherein said input signal comprises first and second component signals, wherein each signal has first and second distinct states, further comprising a first switch having first and second positions and a second switch having first and second positions, wherein the first switch when the first position provides the first state of the first component signal and when in the second position provides the second state of the first component signal and wherein the second switch when in the first position provides the first state of the second component signal and when in the second position provides the second state of the second component signal.

13. A counting device, comprising:
    an input for receiving an input signal having at least three distinct input states;
    a memory for storing a count; and
    circuitry connected to receive said input signal and responsive to a predetermined sequence of input states of said input signal to vary said count, wherein said predetermined sequence includes the at least three input states, wherein said input signal comprises first and second component signals, wherein each signal has first and second distinct states, wherein the first state of the first component signal is provided by the voltage stored on a charged capacitor and the second state first component signal is provided by discharging said capacitor.

14. A counting device as claimed in claim 13, further comprising means for recharging said capacitor.

15. A counting device as claimed in claim 14, wherein said recharging means comprises a switch responsive to a control signal for connecting the capacitor to a voltage source.

16. A counting device as claimed in claim 15, wherein said control signal is a regular pulsed signal.

17. A counting device, comprising:
    an input for receiving an input signal having at least three distinct input states;
    a memory for storing a count; and
    circuitry connected to receive said input signal and responsive to a predetermined sequence of input states of said input signal to vary said count, wherein said predetermined sequence includes the at least three input states, wherein said memory comprises a BCD counter, further comprising a display driven by a drive means, further comprising means, for displaying the value of the count intermittently on the display in response to the count reaching a predetermined value.

18. A counting device, comprising:

an input for receiving an input signal having at least three distinct input states;

a memory for storing a count; and circuitry connected to receive said input signal and responsive to a predetermined sequence of input states of said input signal to vary said count, wherein said predetermined sequence includes the at least three input states, further comprising display drive means for displaying the value of the count, further comprising a power supply for powering the device and display control means responsive to the interruption of said power supply to disable said display drive means or to control said display drive means to display an error message.

19. A counting device, comprising:

an input for receiving an input signal having at least three distinct input states;

a memory for storing a count; and circuitry connected to receive said input signal and responsive to a predetermined sequence of input states of said input signal to vary said count, wherein said predetermined sequence includes the at least three input states, further comprising display drive means for displaying the value of the count, further comprising display control means responsive, in the absence of a control signal, to the connection of said power supply to disable said display drive means or to control said display drive means to display an error message.

20. A counting device as claimed in claim 19, wherein said control signal is an externally applied signal.

21. A counting device, comprising:

an input for receiving an input signal having at least three distinct input states;

a memory for storing a count; and circuitry connected to receive said input signal and responsive to a predetermined sequence of input states of said input signal to vary said count, wherein said predetermined sequence includes the at least three input states, further comprising a voltage augmentation means having a capacitor and arranged to operate in separate modes, wherein in a first mode of operation a first plate of the capacitor is connected to a first voltage and the second plate of the capacitor is connected to a second voltage and in the second mode the first plate of the capacitor is connected to the second voltage and the second plate of the capacitor is connected to a node of the voltage augmentation means.

* * * * *